US012692310B2

(12) United States Patent
Yang et al.

(10) Patent No.: US 12,692,310 B2
(45) Date of Patent: Jul. 28, 2026

(54) ASIC1 CHANNEL ANTAGONIST ANTIBODY

(71) Applicant: ShanghaiTech University, Pudong Distict (CN)

(72) Inventors: Guang Yang, Shanghai (CN); Min Qiang, Shanghai (CN)

(73) Assignee: Shanghaitech University, Shanghai (CN)

( * ) Notice: Subject to any disclaimer, the term of this patent is extended or adjusted under 35 U.S.C. 154(b) by 1136 days.

(21) Appl. No.: 17/628,869

(22) PCT Filed: Jul. 23, 2019

(86) PCT No.: PCT/CN2019/097246
§ 371 (c)(1),
(2) Date: Jan. 20, 2022

(87) PCT Pub. No.: WO2021/012176
PCT Pub. Date: Jan. 28, 2021

(65) Prior Publication Data
US 2023/0287107 A1 Sep. 14, 2023

(51) Int. Cl.
*C07K 16/28* (2006.01)
*A61P 9/10* (2006.01)

(52) U.S. Cl.
CPC ............... *C07K 16/28* (2013.01); *A61P 9/10* (2018.01); *C07K 2317/52* (2013.01); *C07K 2317/565* (2013.01)

(58) Field of Classification Search
CPC ............... C07K 16/28; C07K 2317/52; C07K 2317/565; C07K 2317/21; C07K 2317/622; C07K 2317/74; C07K 2317/76; C07K 2317/92; A61P 9/10; A61P 25/00; G01N 33/6893; G01N 2800/2871; A61K 2039/505
See application file for complete search history.

(56) References Cited

FOREIGN PATENT DOCUMENTS

| CN | 105713089 A | 6/2016 |
|---|---|---|
| EP | 2 298 345 A2 | 1/2006 |
| WO | WO-2011/051349 A1 | 5/2011 |
| WO | WO-2013/116296 A1 | 8/2013 |
| WO | WO-2020/243912 A1 | 12/2020 |

OTHER PUBLICATIONS

Janeway, C. A. Jr. et al., Immunobiology: The Immune System in Health and Disease. Chapter 3: Structure of the Antibody Molecule and Immunoglobulin Genes. 3rd Edition, 1997 Garland Publishing Inc., pp. 3:1-3:11 (Year: 1997).*
Edwards, B. M. et al. The Remarkable Flexibility of the Human Antibody Repertoire; Isolation of Over One Thousand Different Antibodies to a Single Protein, BLyS. J Mol Biol 2003; 334:103-118. (Year: 2003).*

Almagro, J.C. & Fransson, J. "Humanization of antibodies" Frontiers in Bioscience. 2008; 13:1619-33 (Year: 2008).*
Nakakido et al. "Development of novel humanized VHH synthetic libraries based on physicochemical analyses." Scientific Report 2023, 14:19533:1-13 (Year: 2023).*
Feng-Lai Yuan et al: "Acid-sensing ion channel la mediates acid-induced increases in intracellular calcium in rat articular chondrocytes", Molecular and Cellular Biochemistry, vol. 340, No. 1-2, Feb. 24, 2010, pp. 153-159.
Peterson Andrew et al: "Commentary: Potential Therapeutic Consequences of an Acid-Sensing Ion Channel 1a-Blocking Antibody", Frontiers in Pharmacology, vol. 10, Aug. 30, 2019.
Song Xing-Lei et al: "Postsynaptic Targeting and Mobility of Membrane Surface-Localized hASIC1Ia", Neuroscience Bulletin, vol. 37, No. 2, Sep. 30, 2020, pp. 145-165.
Extended European Search Report on EP Appln. 19931715.7 dated Dec. 19, 2022.
Leng Tiandong et al: "Proton-sensitive cation channels and ion exchangers in ischemic brain injury: New therapeutic targets for stroke?", Progress in Neurobiology, vol. 115, Jan. 24, 2014 (Jan. 24, 2014), pp. 189-209.
Ouchi, A. et al. (2019), "The role of Acid-sensing ion channel 1a in a mouse model of ischemic retinopathy."; Investigative Ophthalmology & Visual Science, vol. 60, No. 9, 5739, & Annual Meeting of the Association for Research in Vision and Ophthalmology (ARVO); Vancouver, Canada, Apr. 28-May 2, 2019.
Qiang, M. et al. (2018), "Selection of an ASIC1a-blocking combinatorial antibody that protects cells from ischemic death"; PNAS, vol. 115, No. 32, E7469-E7477.
International Search Report & Written Opinion of the International Searching Authority issued in International Application No. PCT/CN2019/097246, mailed Oct. 18, 2019 (ISA/CN).
International Search Report & Written Opinion of the International Searching Authority issued in International Application No. PCT/CN2019/097246, uploaded Oct. 10, 2019 (ISA/KR).
International Search Report & Written Opinion of the International Searching Authority issued in International Application No. PCT/CN2019/097246, uploaded Sep. 11, 2019 (ISA/JP).
International Search Report & Written Opinion of the International Searching Authority issued in International Application No. PCT/CN2019/097246, uploaded Sep. 19, 2019 (ISA/US).
International Search Report & Written Opinion of the International Searching Authority issued in International Application No. PCT/CN2019/097246, uploaded Sep. 30, 2019 (ISA/EP).
International Search Report and Written Opinion of the International Searching Authority issued in International Application No. PCT/CN2019/090041, mailed Mar. 6, 2020.

(Continued)

*Primary Examiner* — Misook Yu
*Assistant Examiner* — Grace H Lunde
(74) *Attorney, Agent, or Firm* — Foley & Lardner LLP

(57) ABSTRACT

The present technology relates generally to compositions and methods of preventing or treating ischemic stroke. The present technology also relates to administering the anti-ASIC1a antibodies in effective amounts to treat a subject suffering from, or predisposed to, ischemic stroke.

20 Claims, 38 Drawing Sheets
Specification includes a Sequence Listing.

(56) References Cited

OTHER PUBLICATIONS

Min Qiang, "Selection of an ASIC1a-blocking combinatorial antibody that protects cells from ischemic death", PNAS, 2018, pp. E7469-E7477, vol. 115, No. 32.
Woods et al., "Monoclonal Antibody as an Emerging Therapies to Ischemic Stroke", Preprint, Not Peer-Reviewed Version, May 28, 2019, pp. 1-17, Retrieved from the Internet: <URL: https://www.preprints.org/manuscript/20190 5.0326/vl>.

* cited by examiner

ASC01     ASC02     ASC03

ASC04     ASC05     ASC06

$IC_{50} = 85 \pm 6$ nM
Hillslope=3.2

Ischemia  Reperfusion   Contralateral i.c.v. injection   TTC staining
                         of 4 µL vehicle/inhibitors ↓  1 h  ↓       2 h      ↓         24 h              ↓

PBS    Isotype   ASC06-IgG1 PcTx1

Nucleotide Sequence of ASC01 V$_H$ (SEQ ID NO: 1)

CAGGTGCAGCTGGTGGAGACTGGCCCCCGACTGGTGAAGCCTTCACAGACCCTGT
CCCTCACCTGCACTGTCTCCGGTGGCTCCATCAATAGTGGCGGTTACTACTGGGG
CTGGATCCGCCAGCATTCCGGGAAGGGCCTGGAGTGGATTGGCTACATCTATCCC
AGGGGGAGCAGCTACTACAACCCGTCCCTCAGGAGTCGAGTTACCATATCAGCA
GACACGTCTAGGAATAACTTCTCCCTGAAGTTGACCTCTGTGACTGCCGCGGACA
CGGCCGTGTATTACTGTGCGAGAGTCGGTTATACGGGTGCTTTTGATATCTGGGG
CCAAGGCACCCTGGTCACCGTCTCCTCA

FIG. 19A

Amino Acid Sequence of ASC01 V$_H$ (SEQ ID NO: 2)

QVQLVETGPRLVKPSQTLSLTCTVSGGSINSGGYYWGWIRQHSGKGLEWIG**YIYPR
GSSYYNPSLRSRVTISADTSRNNFSLKLTSVTAADTAVYYCARVGYTGAFDI**WGQG
TLVTVSS

FIG. 19B

Nucleotide Sequence of ASC01 V$_L$ (SEQ ID NO: 6)

CAGGCTGTGCTCACTCAGCCGTCCTCAGTGTCTGCGGCCCCAGGACAGAAGGTCA
CCATCTCCTGCTCTGGAGGCAACTCCAACATTGGGAATAATTATGTATCTTGGTA
CCAGCAGCTCCCAGGAACAGCCCCCAAACTCCTCATTTATGACAATAATAAGCGA
CCCTCAGGGATTCCTGACCGATTCTCTGGCTCCAAGTCTGGCACGGCAGCCACCC
TGGGCATCACCGGACTCCAGACTGGGGACGAGGCCGATTATTACTGCGGAACAT
GGGATAGCAGTCTGAGTGCTGGGGTGTTCGGCGAAGGGACCCAGCTCACCGTTTT
AGGT

FIG. 20A

Amino Acid Sequence of ASC01 V$_L$ (SEQ ID NO: 7)

QAVLTQPSSVSAAPGQKVTISCSGGNSNIGNNYVSWYQQLPGTAPKLLIYDNNKRPS
GIPDRFSGSKSGTAATLGITGLQTGDEADYYCGTWDSSLSAGVFGEGTQLTVLG

FIG. 20B

Nucleotide Sequence of ASC02 $V_H$ (SEQ ID NO: 11)

CAGGTCCAGCTGGTACAGTCTGGGGCTGAGGTGAAGAAGCCTGGGGCCTCAATG
AAGGTCTCCTGCACGACTTCTGGATACACCGTCACCGGCTACTACATCCACTGGC
TGCGGCAGGCCCCTGGACAAGGGTTTGAGTGGATGGGATGGATCAACCCTAATC
TTGGTGTCACAAATTATGCTCAGAAGTTTCAGGGCAGGGTCTCCATGACCAGGGA
CCCGTCCATCAAGACAGCCTACCTGGAACTGAGCGGGCTGAGATCTGACGACAC
GGCCATGTATTACTGTGCGAGAGCATCTACTGGTGGTATCTTCTATGACTATTGG
GGCCAGGGCACCCTGGTCACCGTCTCCTCA

FIG. 21A

Amino Acid Sequence of ASC02 $V_H$ (SEQ ID NO: 12)

QVQLVQSGAEVKKPGASMKVSCTTSGYTVTGYYIHWLRQAPGQGFEWMG**WINPN
LGVTNYAQKFQGRVSMTRDPSIKTAYLELSGLRSDDTAMYYCARASTGGIFYDY**W
GQGTLVTVSS

FIG. 21B

Nucleotide Sequence of ASC02 $V_L$ (SEQ ID NO: 16)

AATTTTATGCTGACTCAGCCCCACTCTATGTCGGAGTCTCCGGGGAAGACGGTTA
CCATCTCCTGCACCCGCAGCAGTGGCAATATTGCCAGCAACTATGTGCAGTGGTA
CCAGCAGCGCCCGGGCAGTTCCCCCACCACTGTGATTTATGACGATAACCAAAGA
CCCTCTGGGGTCCCTGATCGGTTCTCTGGCTCCATCGACAGCATCTCCAACTCTGC
CTCCCTCACCATCTCTGGACTGAAGACTGAGGACGAGGCTGACTACTATTGTCAG
TCTTATGATAGCAGCAGTGTGATATTCGGCGGAGGGACCAAGCTGACCGTCCTAG
GT

FIG. 22A

Amino Acid Sequence of ASC02 $V_L$ (SEQ ID NO: 17)

NFMLTQPHSMSESPGKTVTISCTRSSGNIASNYVQWYQQRPGSSPTTVIYDDNQRPS
GVPDRFSGSIDSISNSASLTISGLKTEDEADYYCQSYDSSSVIFGGGTKLTVLG

FIG. 22B

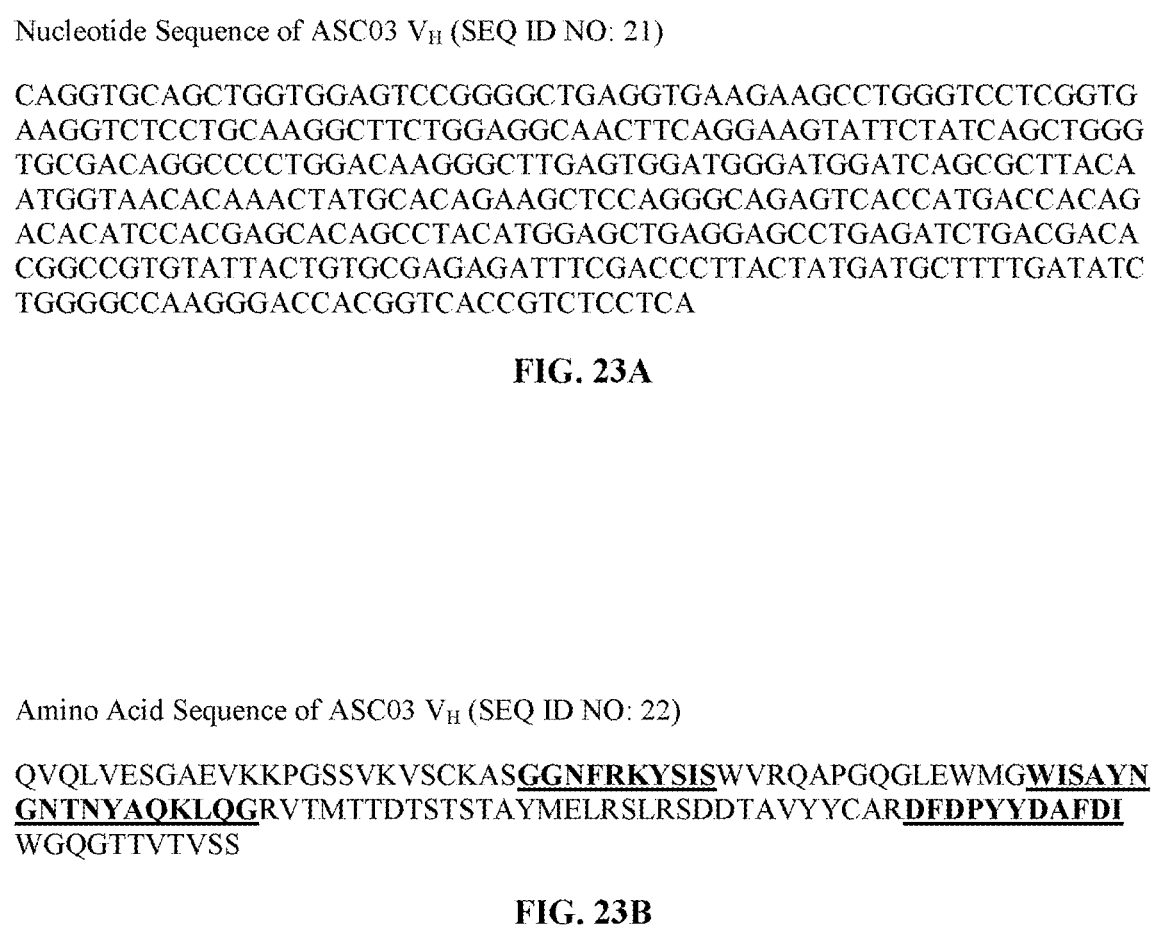

Nucleotide Sequence of ASC03 V$_H$ (SEQ ID NO: 21)

CAGGTGCAGCTGGTGGAGTCCGGGGCTGAGGTGAAGAAGCCTGGGTCCTCGGTG
AAGGTCTCCTGCAAGGCTTCTGGAGGCAACTTCAGGAAGTATTCTATCAGCTGGG
TGCGACAGGCCCCTGGACAAGGGCTTGAGTGGATGGGATGGATCAGCGCTTACA
ATGGTAACACAAACTATGCACAGAAGCTCCAGGGCAGAGTCACCATGACCACAG
ACACATCCACGAGCACAGCCTACATGGAGCTGAGGAGCCTGAGATCTGACGACA
CGGCCGTGTATTACTGTGCGAGAGATTTCGACCCTTACTATGATGCTTTTGATATC
TGGGGCCAAGGGACCACGGTCACCGTCTCCTCA

FIG. 23A

Amino Acid Sequence of ASC03 V$_H$ (SEQ ID NO: 22)

QVQLVESGAEVKKPGSSVKVSCKASGGNFRKYSISWVRQAPGQGLEWMG**WISAYN
GNTNYAQKLQGRVTMTTDTSTSTAYMELRSLRSDDTAVYYCARDFDPYYDAFDI**
WGQGTTVTVSS

FIG. 23B

Nucleotide Sequence of ASC03 V$_L$ (SEQ ID NO: 26)

CAGTCTGCCCTGACTCAGCCTGCCTCCGTGTCTGGGTCTCCTGGACAGTCGATCA
CCATCTCCTGCACTGGGACCAGCAGTGACGTTGGTGCTTATAATTATGTCTCCTG
GTACCAACAACACCCAGGCAAAGCCCCCAAACTCATGATTTATGATGTCAGTAAT
CGGCTCTCAGGGGTTTCTAATCGCTTCTCTGGCTCCAAGTCTGGCAACAGGGCCT
CCCTGACCATCTCTGGGCTCCAGGCTGAGGACGAGGCTGATTATTACTGCAGCTC
ATATAGAAGCGGCAACAGTCTGGCGTTCGGCGGAGGGACCAAGCTGACCGTCCT
AGGT

FIG. 24A

Amino Acid Sequence of ASC03 V$_L$ (SEQ ID NO: 27)

QSALTQPASVSGSPGQSITISC<u>TGTSSDVGAYNYVS</u>WYQQHPGKAPKLMIY<u>DVSNRL</u>
<u>S</u>GVSNRFSGSKSGNRASLTISGLQAEDEADYYC<u>SSYRSGNSLA</u>FGGGTKLTVLG

FIG. 24B

Nucleotide Sequence of ASC04 $V_H$ (SEQ ID NO: 31)

CAGGTCCAGCTGGTGCAGTCTGGGGCTGAGGTGAAGAAGCCTGGGTCCTCGGTG
AAGGTCTCCTGCAAGGCTTCTGGGGGCACCTTCAGCACCTACGCTATCAACTGGG
TGCGACAGGCCCCTGGACAAGGGCTTGAGTGGATGGGATGGATGAACCCTAACA
GTGGTAACACAGGCTATGCACAGAAGTTCCAGGGCAGAGTCACCATGACCAGGA
ACACCTCCATAAGCACAGCCTACATGGAGCTGAGCAGCCTGAGATCTGAGGACA
CGGCCGTGTATTACTGTGCGAGATATAGCTACGGTATGGACGTCTGGGGCCAAGG
GACTACGGTCACCGTCTCCTCA

FIG. 25A

Amino Acid Sequence of ASC04 $V_H$ (SEQ ID NO: 32)

QVQLVQSGAEVKKPGSSVKVSCKASGGTFSTYAINWVRQAPGQGLEWMG**WMNPN
SGNTGYAQKFQGRVTMTRNTSISTAYMELSSLRSEDTAVYYCARYSYGMDV**WGQ
GTTVTVSS

FIG. 25B

Nucleotide Sequence of ASC04 $V_L$ (SEQ ID NO: 36)

CAGGCTGTGCTCACTCAGCCGTCTTCCCTCTCTGCATCTCCTGGAGCATCAGTCAG
TCTCACCTGCACTTTACGCAGTGGCATCAATGTTGGTGCCTACAGGATATACTGG
TACCAGCAGAAGCCAGGGAGTCCTCCCCAGTTTCTCCTGAGGTACAAATCAGACT
CAGATAAGCAGCAGGGCTCTGGAGTCCCCAGCCGCTTCTCTGGATCCAGAGATGC
TTCGGCCAATGCAGGAATTTTACTCATCTCTGGGCTCCGGTCTGAGGATGAGGCT
GACTATTACTGTGCGATTTGGCACAGCAGCGCTTGGGTGTTCGGCGGAGGGACCA
AGCTGACCGTCCTAGGT

FIG. 26A

Amino Acid Sequence of ASC04 $V_L$ (SEQ ID NO: 37)

QAVLTQPSSLSASPGASVSLTCTLRSGINVGAYRIYWYQQKPGSPPQFLLRYKSDSD
KQQGSGVPSRFSGSRDASANAGILLISGLRSEDEADYYCAIWHSSAWVFGGGTKLTV
LG

FIG. 26B

Nucleotide Sequence of ASC05 V$_H$ (SEQ ID NO: 41)

CAGGTGCAGCTGGTGGAGTCCGGGGCTGAGGTGAAGAAGCCTGGGGCCTCAGTG
AGGGTTTCCTGCAAGGCATCTGGATACAGTTTCACCAACTACTATATGCACTGGG
TGCGACAGGCCCCTGGACAAGGGCTTGAGTGGATGGGAATTATCAGCCCTAGTG
GTCGTAGCACAAGCTTCGCACAGAAGTTCCAGGGCAGAGTCACCATGACCAGGG
ACACGTCCACGAGCACAGTCTACATGCATTTGAGCAGCCTGAGATCTGACGACAC
GGCCGTGTATTACTGTGCGAGAGGGGCGTGGTCCACTGATGCTTTTGATATCTGG
GGCCAAGGGACCACGGTCACCGTCTCCTCA

FIG. 27A

Amino Acid Sequence of ASC05 V$_H$ (SEQ ID NO: 42)

QVQLVESGAEVKKPGASVRVSCKAS<u>GYSFTNYYMH</u>WVRQAPGQGLEWMG<u>IISPSG</u>
<u>RSTSFAQKFQG</u>RVTMTRDTSTSTVYMHLSSLRSDDTAVYYCAR<u>GAWSTDAFDI</u>WG
QGTTVTVSS

FIG. 27B

Nucleotide Sequence of ASC05 V$_L$ (SEQ ID NO: 46)

CAGTCTGCCCTGACTCAGCCTGCCTCCGTGTCTGGGTCTCCTGGACAGTCGATCA
CCATCTCCTGCACTGGAACCAGCAGTGATGTTGGGAGTTATAACCTTGTCTCCTG
GTACCAACAGCACCCAGGCAAAGCCCCCAAACTCATGATTTATGAGGGCAGTAA
GCGGCCCTCAGGGGTTTCTAATCGCTTCTCTGGCTCCAAGTCTGGCAACACGGCC
TCCCTGACAATCTCTGGGCTCCAGGCTGAGGATGAGGCTGAGTATCACTGCAGCT
CATTTACAGGCAAGGGTTATGTCTTCGGAACTGGGACCAAGCTGACCGTCCTAGG
TGGCCTCGGG

FIG. 28A

Amino Acid Sequence of ASC05 V$_L$ (SEQ ID NO: 47)

QSALTQPASVSGSPGQSITISCTGTSSDVGSYNLVSWYQQHPGKAPKLMIYEGSKRP
SGVSNRFSGSKSGNTASLTISGLQAEDEAEYHCSSFTGKGYVFGTGTKLTVLGGLG

FIG. 28B

Nucleotide Sequence of ASC06 $V_H$ (SEQ ID NO: 51)

CAGGTACAGCTGCAGCAGTCAGGGGGAGGCTTGGTACAGCCTGGGGGGTCCCTG
AGACTCTCCTGTGCAGCCTCTGGATTCACCTTTAGCAGCTATGCCATGAGCTGGG
TCCGCCAGGCTCCAGGGAAGGGGCTGGAGTGGGTCTCAGCTATTAGTGGTAGTG
GTGGTAGCACATACTACGCAGACTCCGTGAAGGGCCGGTTCACCATCTCCAGAG
ACAATTCCAAGAACACGCTGTATCTGCAAATGAACAGCCTGAGAGCCGAGGACA
CGGCCGTATATTACTGTGCGAAAGATAGTTTCTATGGGTATAGCAAGGGGGACTG
GGGCCAGGGCACCCTGGTCACCGTCTCCTCA

FIG. 29A

Amino Acid Sequence of ASC06 $V_H$ (SEQ ID NO: 52)

QVQLQQSGGGLVQPGGSLRLSCAASGFTFSSYAMSWVRQAPGKGLEWVS**AISGSG
GSTYYADSVKGRFTISRDNSKNTLYLQMNSLRAEDTAVYYCAKDSFYGYSKGD**WG
QGTLVTVSS

FIG. 29B

Nucleotide Sequence of ASC06 V$_L$ (SEQ ID NO: 56)

CAGTCTGCCCTGACTCAGCCTGCCTCCGTGTCTGGGTCTCCTGGACAGTCGATCA
CCATCTCCTGCACTGGAACCAGCAGTGACGTTGGTGCTTATAACTATGTCTCCTG
GTACCAACAACAGCCAGGCAAAGCCCCCAAACTCATGATTTATGGGGTCAGTAA
TCGGCCCTCAGGGGTTTCTAATCGCTTCTCTGGCTCCAAGTCTGGCAACGCGGCC
TCCCTGACCATCTCTGGGCTCCAGGCTGAGGACGAGGCTGATTATTACTGCAGCT
CATATACAAGCAGCAGCACTTATGTCTTCGGAACTGGGACCAAGCTGACCGTCCT
AGGT

FIG. 30A

Amino Acid Sequence of ASC06 V$_L$ (SEQ ID NO: 57)

QSALTQPASVSGSPGQSITISCTGTSSDVGAYNYVSWYQQQPGKAPKLMIYGVSNRP
SGVSNRFSGSKSGNAASLTISGLQAEDEADYYCSSYTSSSTYVFGTGTKLTVLG

FIG. 30B

ASIC1 CHANNEL ANTAGONIST ANTIBODY

CROSS REFERENCE TO RELATED APPLICATIONS

This is a U.S. National Stage Application under 35 U.S.C. § 371 of International Patent Application No. PCT/CN2019/097246, filed on Jul. 23, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 4, 2022, is named 113536-0144_Sequence-Listing.txt and is approximately 28,956 bytes in size.

TECHNICAL FIELD

The present technology relates generally to compositions and methods of preventing or treating diseases associated with ASIC1a activity and/or signaling. More particularly, the present technology provides administering to a subject an effective amount of the anti-ASIC1a antibodies to treat a subject suffering from, or predisposed to, ischemic stroke and related conditions caused by or related to ASIC1a activity and/or signaling.

BACKGROUND

The following description is provided to assist the understanding of the reader. None of the information provided or references cited is admitted to be prior art.

Acid-Sensing Ion Channels (ASICs) are gated by extracellular protons. ASICs are cation channels activated by extracellular acidosis. At least four genes have been identified that encode six ASIC subunits: ASIC1a, ASIC1b, ASIC2a, ASIC2b, ASIC3, and ASIC4, among which, the "a" and "b" designations represent alternatively spliced variants of ASIC1 and ASIC2 genes, ACCN2 and ACCN1, respectively. Functional ASIC channels, which are sensitive to blockade by amiloride, are composed of three subunits assembled in either homomeric or heteromeric forms. ASIC1a is highly expressed in the brain, and forms functional homo- or heteromeric channels with other ASIC isoforms. With an activation threshold near pH 7.0, ASIC1a serves as a primary sensor of acidosis in the brain and is implicated in normal as well as patho-physiology.

SUMMARY OF THE PRESENT DISCLOSURE

In one aspect, the present technology provides methods for treating ischemic stroke in a subject in need thereof, comprising administering to the subject a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, 43, and 53; a $V_H$-CDR2 sequence of selected from the group consisting of: SEQ ID NOs: 4, 14, 24, 34, 44, and 54; and a $V_H$-CDR3 sequence selected from the group consisting of: SEQ ID NOs: 5, 15, 25, 35, 45, and 55; and the $V_L$ comprises an amino acid sequence selected from the group consisting of: a $V_L$-CDR1 sequence selected from the group consisting of: SEQ ID NOs: 8, 18, 28, 38, 48, and 58; a $V_L$-CDR2 sequence of selected from the group consisting of: SEQ ID NOs: 9, 19, 29, 39, 49, and 59; and a $V_L$-CDR3 sequence selected from the group consisting of: SEQ ID NOs: 10, 20, 30, 40, 50, and 60.

Additionally or alternatively, in some embodiments, the $V_H$ comprises an amino acid sequence selected from the group consisting of SEQ ID NOs: 2, 12, 22, 32, 42, and 52. Additionally or alternatively, in some embodiments, the $V_L$ comprises an amino acid sequence selected from the group consisting of SEQ ID NOs: 7, 17, 27, 37, 47 and 57. In some embodiments, the antibody or antigen binding fragment thereof comprises a $V_H$ amino acid sequence and a $V_L$ amino acid sequence selected from the group consisting of: SEQ ID NO: 2 and SEQ ID NO: 7 (ASC01); SEQ ID NO: 12 and SEQ ID NO: 17 (ASC02); SEQ ID NO: 22 and SEQ ID NO: 27 (ASC03); SEQ ID NO: 32 and SEQ ID NO: 37 (ASC04); SEQ ID NO: 42 and SEQ ID NO: 47 (ASC05); and SEQ ID NO: 52 and SEQ ID NO: 57 (ASC06), respectively. Additionally or alternatively, in some embodiments, the antibody or antigen binding fragment thereof is ASC06.

Additionally or alternatively, in some embodiments, the antibody or antigen binding fragment thereof further comprises a Fc domain of an isotype selected from the group consisting of IgG1, IgG2, IgG3, IgG4, IgA1, IgA2, IgM, IgD, and IgE. Additionally or alternatively, in some embodiments, the antibody or antigen binding fragment thereof is selected from the group consisting of Fab, F(ab')$_2$, Fab', scF$_v$, and F$_v$. Additionally or alternatively, in some embodiments, the antibody or antigen binding fragment thereof is a monoclonal antibody, a chimeric antibody, a humanized antibody, or a bispecific antibody.

Additionally or alternatively, in some embodiments, the antibody or antigen binding fragment thereof comprises a $V_H$ amino acid sequence and a $V_L$ amino acid sequence selected from the group consisting of: SEQ ID NO: 2 and SEQ ID NO: 7 (ASC01); SEQ ID NO: 12 and SEQ ID NO: 17 (ASC02); SEQ ID NO: 22 and SEQ ID NO: 27 (ASC03); SEQ ID NO: 32 and SEQ ID NO: 37 (ASC04); SEQ ID NO: 42 and SEQ ID NO: 47 (ASC05); and SEQ ID NO: 52 and SEQ ID NO: 57 (ASC06), respectively.

Additionally or alternatively, in some embodiments, the antibody or antigen binding fragment thereof binds to the ASIC1a protein. Additionally or alternatively, in some embodiments, the antibody or antigen binding fragment thereof binds a cell expressing the ASIC1a protein, or a fragment thereof. Additionally or alternatively, in some embodiments, the antibody or antigen binding fragment thereof binds an extracellular domain of the ASIC1a protein or full-length ASIC1a protein. Additionally or alternatively, in some embodiments, the antibody or antigen binding fragment thereof binds an epitope that spans two ASIC1a subunits. Additionally or alternatively, in some embodiments, the antibody or antigen binding fragment thereof inhibits proton-induced ASIC1a currents.

In one aspect, the present technology provides alleviating one or more symptoms of ischemic stroke in a subject in need thereof, the method comprising: administering to the subject a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, 43, and 53; a $V_H$-CDR2 sequence of selected from the group consisting of: SEQ ID NOs: 4, 14, 24, 34, 44, and 54; and a $V_H$-CDR3 sequence selected from the group consisting of: SEQ ID NOs: 5, 15, 25, 35, 45, and 55; and the $V_L$ comprises an amino acid sequence selected from the group consisting of: a $V_L$-CDR1 sequence selected from the group consisting of: SEQ ID NOs: 8, 18, 28, 38, 48, and 58; a $V_L$-CDR2 sequence of selected from the group consisting of: SEQ ID NOs: 9, 19, 29, 39, 49, and 59; and a $V_L$-CDR3 sequence selected from the group consisting of: SEQ ID NOs: 10, 20, 30, 40, 50, and 60.

Additionally or alternatively, in some embodiments, the antibody or antigen binding fragment thereof further comprises a Fc domain of an isotype selected from the group consisting of IgG1, IgG2, IgG3, IgG4, IgA1, IgA2, IgM, IgD, and IgE. Additionally or alternatively, in some embodiments, the antibody or antigen binding fragment thereof is selected from the group consisting of Fab, F(ab')$_2$, Fab', scF$_v$, and F$_v$. Additionally or alternatively, in some embodiments, the antibody or antigen binding fragment thereof is a monoclonal antibody, a chimeric antibody, a humanized antibody, or a bispecific antibody.

Additionally or alternatively, in some embodiments, the antibody or antigen binding fragment thereof binds to the ASIC1a protein. Additionally or alternatively, in some embodiments, the antibody or antigen binding fragment thereof binds an extracellular domain of the ASIC1a protein or full length-ASIC1a protein. Additionally or alternatively, in some embodiments, the antibody or antigen binding fragment thereof binds an epitope that spans two ASIC1a subunits. Additionally or alternatively, in some embodiments, the antibody or antigen binding fragment thereof inhibits ASIC1a. Additionally or alternatively, in some embodiments, the antibody or antigen binding fragment thereof inhibits ASIC1a currents. Additionally or alternatively, in some embodiments, the antibody or antigen binding fragment thereof inhibits proton-induced ASIC1a currents.

Additionally or alternatively, in some embodiments, the one or more symptoms of ischemic stroke is sudden weakness, paralysis or numbness of the face, arms, or legs, drooping of one side of the face, confusion, difficulty with speaking, difficulty with understanding speech, trouble seeing in one or both eyes, blurred vision, blackened vision, double vision, difficulty with breathing, dizziness, difficulty with walking, loss of balance, loss of coordination, unexplained falls, loss of consciousness, sudden headache or severe headache. Additionally or alternatively, in some embodiments, the one or more symptoms of ischemic stroke is sudden-onset face weakness, drooping of one side of the face, arm drift or abnormal speech.

In one aspect, the present technology provides a method for treating ischemic stroke in a subject in need thereof, comprising administering to the subject a therapeutically effective amount of an antibody or antigen binding fragment thereof comprising (a) a light chain immunoglobulin variable domain sequence ($V_L$) that is at least 80%, at least 85%, at least 90%, at least 95%, or at least 99% identical to the light chain immunoglobulin variable domain sequence of any one of SEQ ID NOs: 7, 17, 27, 37, 47, or 57; and/or (b) a heavy chain immunoglobulin variable domain sequence ($V_H$) that is at least 80%, at least 85%, at least 90%, at least 95%, or at least 99% identical to the heavy chain immunoglobulin variable domain sequence present in any one of SEQ ID NOs: 2, 12, 22, 32, 42, or 52.

In one aspect, the present technology provides an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, and 43; a $V_H$-CDR2 sequence of selected from the group consisting of: SEQ ID NOs: 4, 14, 24, 34, and 44; and a $V_H$-CDR3 sequence selected from the group consisting of: SEQ ID NOs: 5, 15, 25, 35, and 45; and the $V_L$ comprises an amino acid sequence selected from the group consisting of: a $V_L$-CDR1 sequence selected from the group consisting of: SEQ ID NOs: 8, 18, 28, 38, and 48; a $V_L$-CDR2 sequence of selected from the group consisting of: SEQ ID NOs: 9, 19, 29, 39, and 49; and a $V_L$-CDR3 sequence selected from the group consisting of: SEQ ID NOs: 10, 20, 30, 40, and 50. Additionally or alternatively, in some embodiments, the antibody, or antigen binding fragment thereof, further comprising a Fc domain of an isotype selected from the group consisting of IgG1, IgG2, IgG3, IgG4, IgA1, IgA2, IgM, IgD, and IgE. Additionally or alternatively, in some embodiments, the antigen binding fragment is selected from the group consisting of Fab, F(ab')$_2$, Fab', scF$_v$, and F$_v$. Additionally or alternatively, in some embodiments, the antibody, or antigen binding fragment thereof is a monoclonal antibody, a chimeric antibody, a humanized antibody, or a bispecific antibody. Additionally or alternatively, in some embodiments, antibody, or antigen binding fragment thereof binds to the ASIC1a protein. Additionally or alternatively, in some embodiments, the antibody or antigen binding fragment thereof binds an extracellular domain of the ASIC1a protein or full-length ASIC1a protein. Additionally or alternatively, in some embodiments, the antibody or antigen binding fragment thereof binds an epitope that spans two ASIC1a subunits. Additionally or alternatively, in some embodiments, the antibody or antigen binding fragment thereof inhibits ASIC1a currents. Additionally or alternatively, in some embodiments, the antibody or antigen binding fragment thereof inhibits proton-induced ASIC1a currents.

In one aspect, the present technology provides a composition comprising the antibody of any embodiment disclosed herein. Additionally or alternatively, in some embodiments, the nucleic acid sequence is selected from the group consisting of SEQ ID NOs: 1, 6, 11, 16, 21, 26, 31, 36, 41, 46, 51, and 56.

In one aspect, the present technology provides a host cell or a vector expressing any nucleic acid disclosed herein.

In one aspect, the present technology provides a kit comprising the antibody, or antigen binding fragment thereof of any embodiment disclosed herein and instructions for use. Additionally or alternatively, in some embodiments, the antibody, or antigen binding fragment thereof of any embodiment disclosed herein is coupled to at least one detectable label selected from the group consisting of a radioactive label, a fluorescent label, and a chromogenic label. Additionally or alternatively, in some embodiments, the kit further comprises a secondary antibody that specifically binds to the antibody, or antigen binding fragment thereof of any embodiment disclosed herein.

In one aspect, the present technology provides a method for detecting ASIC1a protein in a biological sample comprising contacting the biological sample with the antibody, or antigen binding fragment thereof of any embodiment disclosed herein, wherein the antibody, or antigen binding fragment thereof is conjugated to a detectable label; and detecting the presence and the level of the detectable label in the biological sample.

BRIEF DESCRIPTION OF THE DRAWINGS

FIG. 8B (bottom panel) shows a bar graph illustrating volumes of infarct areas in brains from the mice treated as in FIG. 8B (top panel). The * indicates a p value <0.05, ** indicates a p value <0.01 compared to the sham-control group. NS=not significant.

FIG. 9A shows the subarea of an unprocessed image. Scale bar=50 nm. FIG. 9B shows representative single particles selected from FIG. 9A. Scale bar=10 nm. FIG. 9C shows the corresponding representative class averages based on single particles (N=5,064). Scale bar=10 nm.

FIG. 10B (lower panels) shows the amplified fields of neurites indicating that ASC06-IgG1 binding occurs in the postsynaptic dendrites.

FIG. 12A shows the SDS-PAGE analysis of the composition of ΔhASIC1a-nanodisc. The ΔhASIC1a-nanodisc, which is illustrated on the right side, using computation modeling, in which the blue, yellow, purple colored ribbons on top represent a putative ΔhASIC1a trimer configuration, the red ribbons on the side of the disc represent MSP1, and the white ball clusters represent 1,2-dimyristoyl-sn-glycero-3-phosphocholine (DMPC). The empty nanodisc refers to a nanodisc assembly using acetylcholine instead of ΔhASIC1a.

FIG. 16 illustrates that ASC06-IgG1 interferes with neither SSD nor activation of ASIC1a.

Figure 17A:
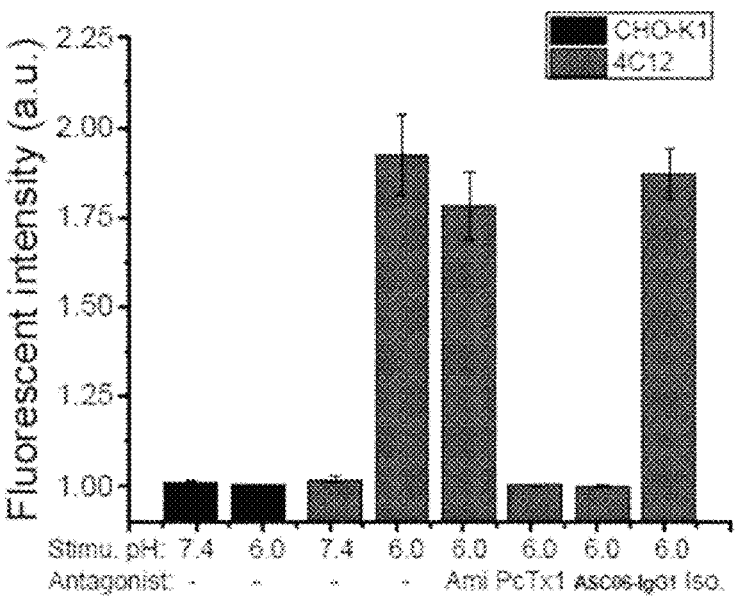
FIG. 17A shows the maximal fluorescent intensity of calcium influx in cytoplasm after acid induction in CHO-K1 cells, or hASIC1a-mCherry overexpressing stable CHO-K1 cells (4C12). Where indicated, 4C12 cells were pre-incubated with amiloride, PcTx1, ASC06-IgG1 or an isotype control antibody.
Figure 17B:
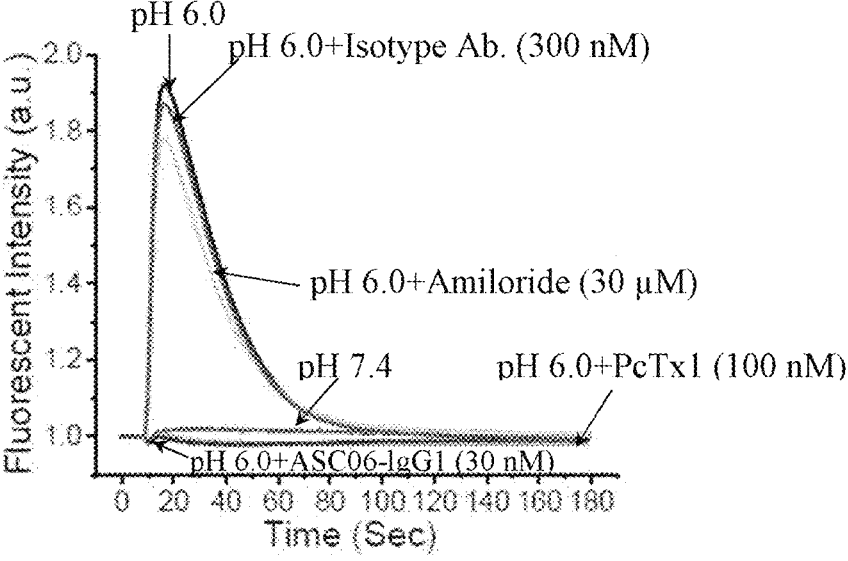

FIG. 17B the representative progression curves of the acid induced calcium influx in the 4C12 in the presence of amiloride, PcTx1, ASC06-IgG1 or an isotype control antibody. An irrelevant antibody was taken as isotype control.

Figure 18:
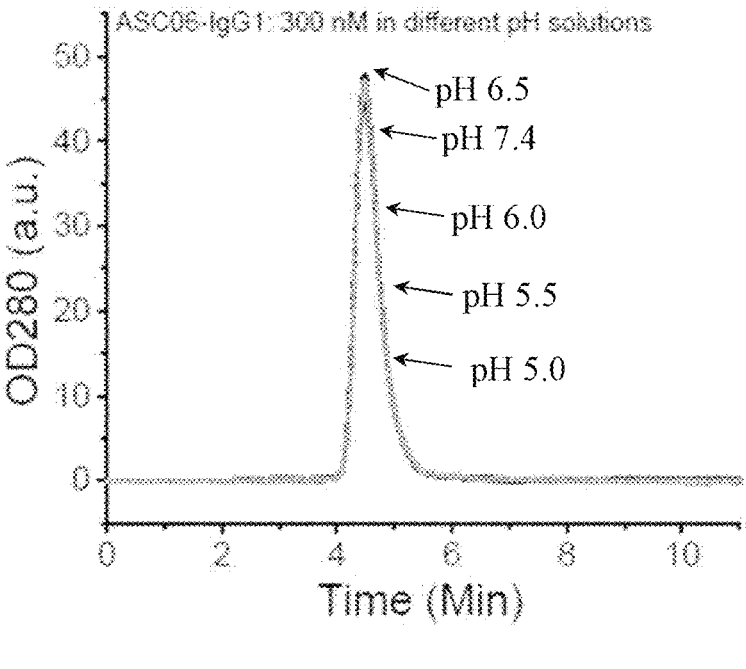

FIG. 18 shows the size exclusion chromatography-high performance liquid chromatography (SEC-HPLC) analysis of ASC06-IgG1. ASC06-IgG1 (0.5 mg/mL) was incubated with extracellular fluid of different pH for 6 hours at 37° C., followed by SEC-HPLC analysis.

FIG. 19A shows the nucleotide sequence of the $V_H$ domain of ASC01 (SEQ ID NO: 1).

FIG. 19B shows the amino acid sequence of the $V_H$ domain of ASC01 (SEQ ID NO: 2). $V_H$ CDR1 (SEQ ID NO: 3), $V_H$ CDR2 (SEQ ID NO: 4) and $V_H$ CDR3 (SEQ ID NO: 5) are indicated by an underlined boldface font.

FIG. 20A shows the nucleotide sequence of the $V_L$ domain of ASC01 (SEQ ID NO: 6)

FIG. 20B shows the amino acid sequence of the $V_L$ domain of ASC01 (SEQ ID NO: 7). $V_L$ CDR1 (SEQ ID NO: 8), $V_L$ CDR2 (SEQ ID NO: 9) and $V_L$ CDR3 (SEQ ID NO: 10) are indicated by an underlined boldface font.

FIG. 21A shows the nucleotide sequence of the $V_H$ domain of ASC02 (SEQ ID NO: 11).

FIG. 21B shows the amino acid sequence of the $V_H$ domain of ASC02 (SEQ ID NO: 12). $V_H$ CDR1 (SEQ ID NO: 13), $V_H$ CDR2 (SEQ ID NO: 14) and $V_H$ CDR3 (SEQ ID NO: 15) are indicated by an underlined boldface font.

FIG. 22A shows the nucleotide sequence of the $V_L$ domain of ASC02 (SEQ ID NO: 16).

FIG. 22B shows the amino acid sequence of the $V_L$ domain of ASC02 (SEQ ID NO: 17). $V_L$ CDR1 (SEQ ID NO: 18), $V_L$ CDR2 (SEQ ID NO: 19) and $V_L$ CDR3 (SEQ ID NO: 20) are indicated by an underlined boldface font.

FIG. 23A shows the nucleotide sequence of the $V_H$ domain of ASC03 (SEQ ID NO: 21).

FIG. 23B shows the amino acid sequence of the $V_H$ domain of ASC03 (SEQ ID NO: 22). $V_H$ CDR1(SEQ ID NO:23), $V_H$ CDR2 (SEQ ID NO: 24) and $V_H$ CDR3 (SEQ ID NO: 25) are indicated by an underlined boldface font.

FIG. 24A shows the nucleotide sequence of the $V_L$ domain of ASC03 (SEQ ID NO: 26).

FIG. 24B shows the amino acid sequence of the $V_L$ domain of ASC03 (SEQ ID NO: 27). $V_L$ CDR1 (SEQ ID NO:28), $V_L$ CDR2 (SEQ ID NO: 29) and $V_L$ CDR3 (SEQ ID NO: 30) are indicated by an underlined boldface font.

FIG. 25A shows the nucleotide sequence of the $V_H$ domain of ASC04 (SEQ ID NO: 31).

FIG. 25B shows the amino acid sequence of the $V_H$ domain of ASC04 (SEQ ID NO: 32). $V_H$ CDR1 (SEQ ID NO:33), $V_H$ CDR2 (SEQ ID NO: 34) and $V_H$ CDR3 (SEQ ID NO: 35) are indicated by an underlined boldface font.

FIG. 26A shows the nucleotide sequence of the $V_L$ domain of ASC04 (SEQ ID NO: 36).

FIG. 26B shows the amino acid sequence of the $V_L$ domain of ASC04 (SEQ ID NO: 37). $V_L$ CDR1 (SEQ ID NO: 38), $V_L$ CDR2 (SEQ ID NO: 39) and $V_L$ CDR3 (SEQ ID NO: 40) are indicated by an underlined boldface font.

FIG. 27A shows the nucleotide sequence of the $V_H$ domain of ASC05 (SEQ ID NO: 41).

FIG. 27B shows the amino acid sequence of the $V_H$ domain of ASC05 (SEQ ID NO: 42). $V_H$ CDR1 (SEQ ID NO: 43), $V_H$ CDR2 (SEQ ID NO: 44) and $V_H$ CDR3 (SEQ ID NO: 45) are indicated by an underlined boldface font.

FIG. 28A shows the nucleotide sequence of the V_L domain of ASC05 (SEQ ID NO: 46).

FIG. 28B shows the amino acid sequence of the V_L domain of ASC05 (SEQ ID NO: 47). V_L CDR1 (SEQ ID NO: 48), V_L CDR2 (SEQ ID NO: 49) and V_L CDR3 (SEQ ID NO: 50) are indicated by an underlined boldface font.

FIG. 29A shows the nucleotide sequence of the V_H domain of ASC06 (SEQ ID NO: 51).

FIG. 29B shows the amino acid sequence of the V_H domain of ASC06 (SEQ ID NO: 52). V_H CDR1 (SEQ ID NO: 53), V_H CDR2 (SEQ ID NO: 54) and V_H CDR3 (SEQ ID NO: 55) are indicated by an underlined boldface font.

FIG. 30A shows the nucleotide sequence of the V_L domain of ASC06 (SEQ ID NO: 56).

FIG. 30B shows the amino acid sequence of the V_L domain of ASC06 (SEQ ID NO: 57). V_L CDR1 (SEQ ID NO: 58), V_L CDR2 (SEQ ID NO: 59) and V_L CDR3 (SEQ ID NO: 60) are indicated by an underlined boldface font.

DETAILED DESCRIPTION

It is to be appreciated that certain aspects, modes, embodiments, variations and features of the present technology are described below in various levels of detail in order to provide a substantial understanding of the present technology. The present technology provides methods of treating ischemic stroke and/or related disorders.

While the exemplified antibodies that target the ASIC1a protein described herein are scFv and IgG1 antibodies, the description is intended to embrace broadly to any immunologic binding agent, such as IgG, IgM, IgA, IgD, IgE, and genetically modified IgG, and fragments thereof as well as polypeptides comprising antibody complementarity determining regions (CDR) domains that retain the antigen binding activity described herein.

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. In some embodiments, the anti-ASIC1a antibodies of the present technology is administered by an intracranial (intracerebroventricular) route, an intrathecal route or an intra-arterial route. Administration includes self-administration and the administration by another.

As used herein, the term "amino acid" is used to refer to any organic molecule that contains at least one amino group and at least one carboxyl group. Typically, at least one amino group is at the a position relative to a carboxyl group. The term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding affinity for the molecule of interest that is at least $10^3$ M$^{-1}$ greater, at least $10^4$ M$^{-1}$ greater or at least $10^5$ M$^{-1}$ greater than a binding affinity for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy (V_H) region and the variable light (V_L) region. Together, the V_H region and the V_L region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the 0-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds ASIC1a protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Anti-ASIC1a antibodies of the present technology" as used herein, refers to antibodies (including monoclonal antibodies, polyclonal antibodies, humanized antibodies, chimeric antibodies, recombinant antibodies, multispecific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', $F(ab')_2$, and Fv fragments; diabodies; bi-specific antibodies; linear antibodies; single-chain antibody molecules; and multispecific antibodies formed from antibody fragments.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and Hollinger et al., *Proc. Natl. Acad. Sci. USA,* 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a ASIC1a polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, Fab, Fab' and F(ab')$_2$, but are not limited thereto.

Any of the above-noted antibody fragments are obtained using conventional techniques known to those of skill in the art, and the fragments are screened for binding specificity and neutralization activity in the same manner as are intact antibodies.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a skin tissue, hair, nails, sebaceous glands, or a muscle biopsy sample.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, isolated anti-ASIC1a antibodies of the present technology would be free of materials that would interfere with diagnostic or therapeutic uses of the agent. Such interfering materials may include enzymes, hormones and other proteinaceous and nonproteinaceous solutes.

Figure 9A:
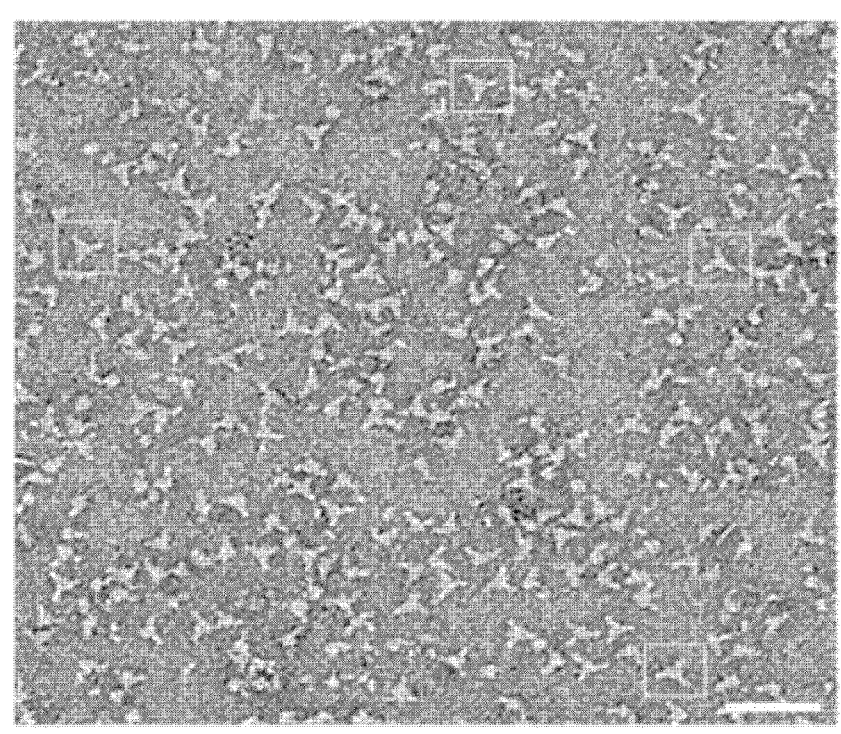
FIGS. 9A-9C show a negative-stain electron microscopy image of the complex of ectodomain of hASIC1a (hASIC1a-ECD) with ASC06-Fab complex.
Figure 9B:
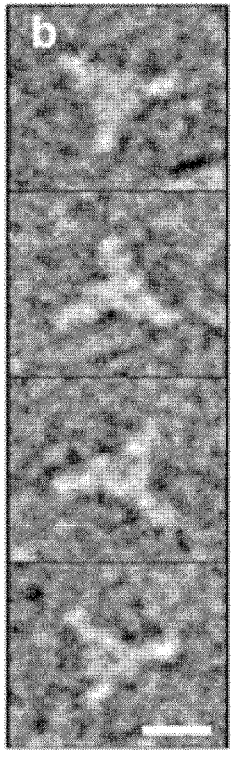
Figure 9C:
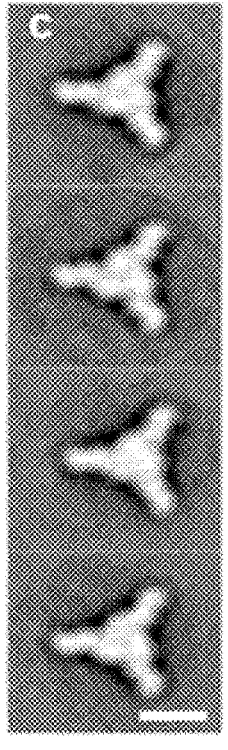
Figure 9D:
FIG. 9D shows the conformational epitope of ASC06-IgG1 as detected by a molecular dynamic simulation. First subunit is displayed on the left side of the image, and a second subunit is shown on the right side. A part of the first subunit, including beta sheets near bottom of the image are located behind the second subunit. The binding site of ASC06-IgG1, which is shown using dots (dark gray dots in the first subunit, light gray dots in the second subunit), is formed by two ASIC1a subunits.
Figure 9E:
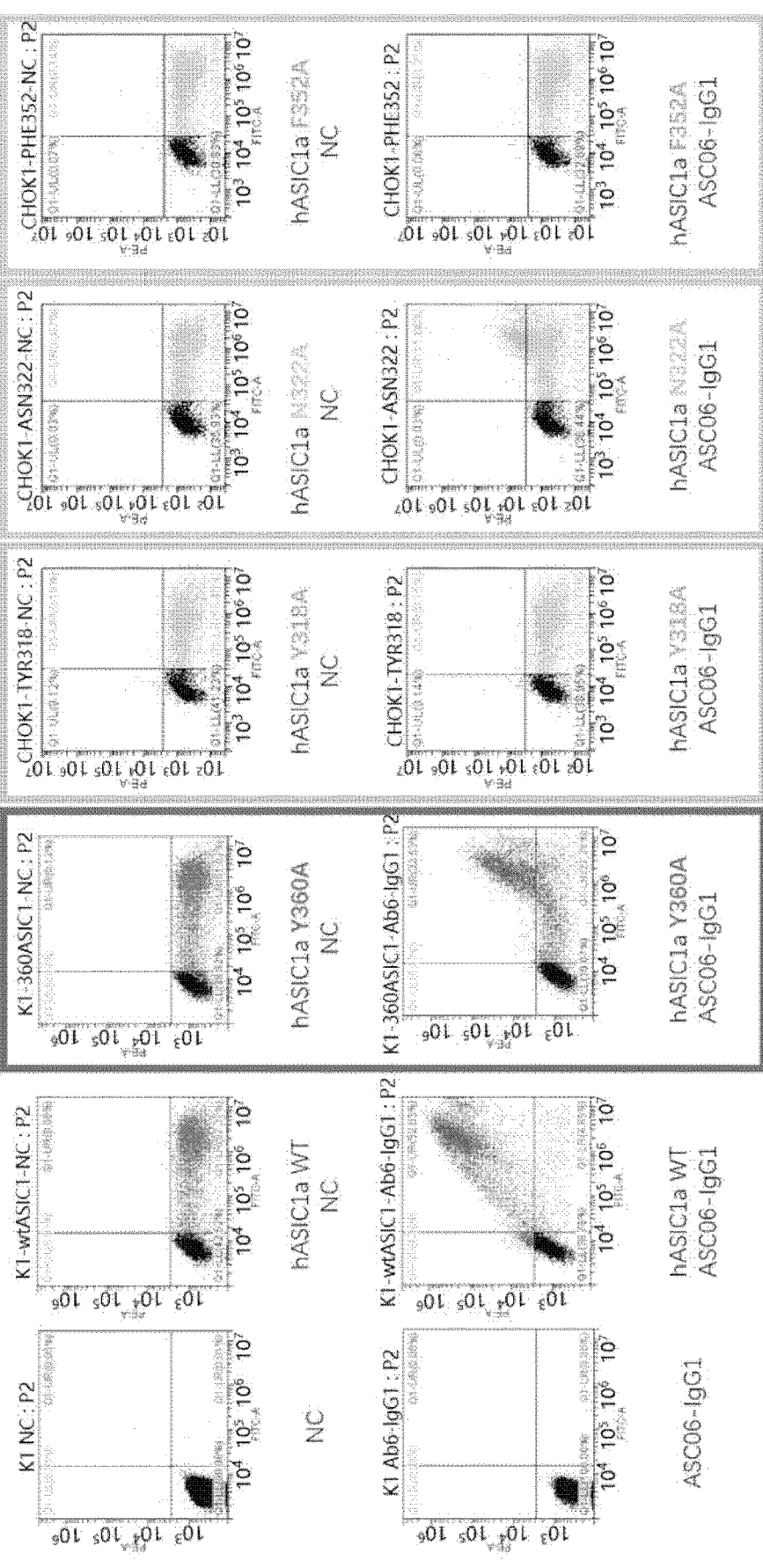
FIG. 9E shows the identification the amino acid residues in hASIC1a protein that have a role in binding to ASC06-IgG1. CHO-K1 cells transiently transfected with the indicated alanine substitution mutant hASIC1a-eYFP proteins were assayed for binding to the ASC06-IgG1 using a FACS-based assay. The top panel shows negative controls (NC) where no first antibody but only second antibody was included. The lower panel shows experiments in which ASC06-IgG1 was incubated with the cells. Positive control where cells expressing wild type hASIC1a protein are shown. Another negative control, in which CHO-K1 cells express no hASIC1a, is also shown on the left hand side.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" is a region of the ASIC1a protein trimer to which the anti-ASIC1a antibodies of the present technology specifically bind, including the extracellular domain of ASIC1a. In some embodiments, the epitope may span two ASIC1a subunits. In some embodiments, the epitope is a conformational epitope or a non-conformational epitope. To screen for anti-ASIC1a antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-ASIC1a antibody binds the same site or epitope as an anti-ASIC1a antibody of the present technology. Alternatively, or additionally, epitope mapping can be performed by methods known in the art. For example, the antibody sequence can be mutagenized such as by alanine scanning, to identify contact residues, as shown in FIG. 9E. In a different method, peptides corresponding to different regions of ASIC1a protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the terms "Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Riechmann et al., *Nature* 332: 323-327 (1988); and Presta, *Curr. Op. Struct. Biol.* 2:593-596 (1992). See e.g., Ahmed & Cheung, *FEBS Letters* 588(2):288-297 (2014); Saxena & Wu, *Frontiers in immunology* 7: 580 (2016).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or V$_H$) and a heavy chain constant region. The heavy chain constant region is comprised of three domains, CH$_1$, CH$_2$ and CH$_3$. Each light chain is comprised of a light chain variable region (abbreviated herein as LCVR or V$_L$) and a light chain constant region. The light chain constant region is comprised of one domain, C$_L$. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxyl-terminus in the following order: FR$_1$, CDR$_1$, FR$_2$, CDR$_2$, FR$_3$, CDR$_3$, FR$_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816, 567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, PA.).

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$ M, $10^{-6}$ M, $10^{-7}$M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a ASIC1a polypeptide), or an epitope on a particular polypeptide, without substantially binding to any other polypeptide, or polypeptide epitope.

As used herein, the terms "subject," "individual," or "patient" can be an individual organism, a vertebrate, a mammal, or a human.

"Treating", "treat", or "treatment" as used herein covers the treatment of a disease or disorder described herein, in a subject, such as a human, and includes: (i) inhibiting the disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-ASIC1a antibodies described herein are contemplated. For example, it may be desirable to improve the binding affinity and/or other biological properties of the antibody. Amino acid sequence variants of an anti-ASIC1a antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

| Amino Acid Substitutions | | |
| --- | --- | --- |
| Original Residue | Exemplary Substitutions | Conservative Substitutions |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

Pathogenesis of Ischemic Stroke

A stroke is caused by interruption or reduction of the supply of oxygen-rich blood to a part of the brain. Without oxygen, brain cells start to die within a few minutes. Stroke is usually presented through the symptoms such as sudden weakness; paralysis or numbness of the face, arms, or legs, especially on one side of the body; drooping of one side of the face; confusion; difficulty with speaking, such as slurred words, or difficulty understanding speech; trouble seeing in one or both eyes, such as blurred or blackened vision, or double vision in one or both eyes; problems with breathing; dizziness; difficulty with walking; loss of balance or coordination, causing, e.g., unexplained falls; loss of consciousness, and sudden and severe headache. Symptoms which are most common include sudden-onset face weakness (e.g., drooping of one side of the face), arm drift and abnormal speech. These symptoms typically start suddenly, over seconds to minutes, and in most cases do not progress further. Immediate emergency treatment is critical to surviving a stroke with the least amount of damage to the brain and ability to function.

Ischemic strokes, which account for about 87% of all strokes, occur when blood supply to a part of the brain is cut off because of obstruction of the blood vessels by blood clots or other particles. Fatty deposits called plaque can also cause blockages by building up in the blood vessels. The blocked blood flow in an ischemic stroke may be caused by atherosclerosis, which causes narrowing of the arteries overtime. Ischemic strokes can be caused by a blockage anywhere along the arteries feeding the brain.

An ischemic stroke may be an embolic stroke, where a blood clot or plaque fragment forms somewhere else in the body (usually the heart) and travels to the brain. Once in the brain, the clot travels to a blood vessel small enough to block its passage. The clot lodges there, blocking the blood vessel and causing a stroke. About 15% of embolic strokes occur in people with atrial fibrillation (Afib).

An ischemic stroke may be a thrombotic stroke, which is caused by a blood clot that forms inside one of the arteries supplying blood to the brain. This type of stroke is usually seen in people with high cholesterol levels and atherosclerosis. Thrombotic stroke may be large vessel thrombosis or small vessel disease. Large vessel thrombosis occurs in the brain's larger arteries. In most cases it is caused by long-term atherosclerosis in combination with rapid blood clot formation. High cholesterol is a common risk factor for this type of stroke. Small vessel disease or lacunar infarction is closely linked to high blood pressure.

Anti-ASIC1a Antibodies of the Present Technology

The present technology describes methods and compositions for the generation and use of anti-ASIC1a antibodies of the present technology (e.g., anti-ASIC1a antibodies or antigen binding fragments thereof). The anti-ASIC1a antibodies of the present technology may be useful in the diagnosis, or treatment of ischemic stroke. Anti-ASIC1a antibodies of the present technology within the scope of the present technology include, e.g., but are not limited to, monoclonal, chimeric, humanized, bispecific antibodies and diabodies that specifically bind the target polypeptide, a homolog, derivative or a fragment thereof.

The Table below provides the complementarity determining region (CDR) sequences of the anti-ASIC1a antibodies of the present technology:

| Sequence Identifier | Description | Sequence |
|---|---|---|
| SEQ ID NO: 3 | ASC01 $V_H$ CDR1 | GGSINSGGYYWG |
| SEQ ID NO: 4 | ASC01 $V_H$ CDR2 | YIYPRGSSYYNPSLRS |
| SEQ ID NO: 5 | ASC01 $V_H$ CDR3 | VGYTGAFDI |
| SEQ ID NO: 8 | ASC01 $V_L$ CDR1 | SGGNSNIGNNYVS |
| SEQ ID NO: 9 | ASC01 $V_L$ CDR2 | DNNKRPS |
| SEQ ID NO: 10 | ASC01 $V_L$ CDR3 | GTWDSSLSAGV |
| SEQ ID NO: 13 | ASC02 $V_H$ CDR1 | GYTVTGYYIH |
| SEQ ID NO: 14 | ASC02 $V_H$ CDR2 | WINPNLGVTNYAQKFQG |
| SEQ ID NO: 15 | ASC02 $V_H$ CDR3 | ASTGGIFYDY |
| SEQ ID NO: 18 | ASC02 $V_L$ CDR1 | TRSSGNIASNYVQ |
| SEQ ID NO: 19 | ASC02 $V_L$ CDR2 | DDNQRPS |
| SEQ ID NO: 20 | ASC02 $V_L$ CDR3 | QSYDSSSVI |
| SEQ ID NO: 23 | ASC03 $V_H$ CDR1 | GGNFRKYSIS |
| SEQ ID NO: 24 | ASC03 $V_H$ CDR2 | WISAYNGNTNYAQKLQG |
| SEQ ID NO: 25 | ASC03 $V_H$ CDR3 | DFDPYYDAFDI |
| SEQ ID NO: 28 | ASC03 $V_L$ CDR1 | TGTSSDVGAYNYVS |
| SEQ ID NO: 29 | ASC03 $V_L$ CDR2 | DVSNRLS |
| SEQ ID NO: 30 | ASC03 $V_L$ CDR3 | SSYRSGNSLA |
| SEQ ID NO: 33 | ASC04 $V_H$ CDR1 | GGTFSTYAIN |
| SEQ ID NO: 34 | ASC04 $V_H$ CDR2 | WMNPNSGNTGYAQKFQG |
| SEQ ID NO: 35 | ASC04 $V_H$ CDR3 | YSYGMDV |
| SEQ ID NO: 38 | ASC04 $V_L$ CDR1 | TLRSGINVGAYRIY |
| SEQ ID NO: 39 | ASC04 $V_L$ CDR2 | KSDSDKQ |
| SEQ ID NO: 40 | ASC04 $V_L$ CDR3 | AIWHSSAWV |
| SEQ ID NO: 43 | ASC05 $V_H$ CDR1 | GYSFTNYYMH |
| SEQ ID NO: 44 | ASC05 $V_H$ CDR2 | IISPSGRSTSFAQKFQG |
| SEQ ID NO: 45 | ASC05 $V_H$ CDR3 | GAWSTDAFDI |
| SEQ ID NO: 48 | ASC05 $V_L$ CDR1 | TGTSSDVGSYNLVS |
| SEQ ID NO: 49 | ASC05 $V_L$ CDR2 | EGSKRPS |
| SEQ ID NO: 50 | ASC05 $V_L$ CDR3 | SSFTGKGYV |
| SEQ ID NO: 53 | ASC06 $V_H$ CDR1 | GFTFSSYAMS |
| SEQ ID NO: 54 | ASC06 $V_H$ CDR2 | AISGSGGSTYYADSVKG |
| SEQ ID NO: 55 | ASC06 $V_H$ CDR3 | DSFYGYSKGD |
| SEQ ID NO: 58 | ASC06 $V_L$ CDR1 | TGTSSDVGAYNYVSW |

-continued

| Sequence Identifier | Description | Sequence |
|---|---|---|
| SEQ ID NO: 59 | ASC06 V_L CDR2 | GVSNRPS |
| SEQ ID NO: 60 | ASC06 V_L CDR3 | SSYTSSSTYV |

Accordingly, the antibody or antigen binding fragment thereof (anti-ASIC1a antibodies of the present technology) may comprise a heavy chain immunoglobulin variable domain ($V_H$) and a light chain immunoglobulin variable domain ($V_L$), wherein the $V_H$ comprises complementarity determining regions $V_H$ CDR1, $V_H$ CDR2 and $V_H$ CDR3 disclosed herein; and wherein the $V_L$ comprises complementarity determining regions $V_L$ CDR1, $V_L$ CDR2 and $V_L$ CDR3 disclosed herein.

In one aspect, the present technology provides an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, 43, and 53; a $V_H$-CDR2 sequence of selected from the group consisting of: SEQ ID NOs: 4, 14, 24, 34, 44, and 54; and a $V_H$-CDR3 sequence selected from the group consisting of: SEQ ID NOs: 5, 15, 25, 35, 45, and 55; and the $V_L$ comprises an amino acid sequence selected from the group consisting of: a $V_L$-CDR1 sequence selected from the group consisting of: SEQ ID NOs: 8, 18, 28, 38, 48, and 58; a $V_L$-CDR2 sequence of selected from the group consisting of: SEQ ID NOs: 9, 19, 29, 39, 49, and 59; and a $V_L$-CDR3 sequence selected from the group consisting of: SEQ ID NOs: 10, 20, 30, 40, 50, and 60.

Additionally or alternatively, in some embodiments, the $V_H$ comprises a $V_H$-CDR1 sequence selected from the group consisting of: SEQ ID NOs: 3, 13, 23, 33, and 43; a $V_H$-CDR2 sequence of selected from the group consisting of: SEQ ID NOs: 4, 14, 24, 34, and 44; and a $V_H$-CDR3 sequence selected from the group consisting of: SEQ ID NOs: 5, 15, 25, 35, and 45; and the $V_L$ comprises an amino acid sequence selected from the group consisting of: a $V_L$-CDR1 sequence selected from the group consisting of: SEQ ID NOs: 8, 18, 28, 38, and 48; a $V_L$-CDR2 sequence of selected from the group consisting of: SEQ ID NOs: 9, 19, 29, 39, and 49; and a $V_L$-CDR3 sequence selected from the group consisting of: SEQ ID NOs: 10, 20, 30, 40, and 50. Additionally or alternatively, in some embodiments, the antibody, or antigen binding fragment thereof, further comprising a Fc domain of an isotype selected from the group consisting of IgG1, IgG2, IgG3, IgG4, IgA1, IgA2, IgM, IgD, and IgE. Additionally or alternatively, in some embodiments, the antigen binding fragment is selected from the group consisting of Fab, F(ab')$_2$, Fab', scF$_v$, and F$_v$. Additionally or alternatively, in some embodiments, the antibody, or antigen binding fragment thereof is a monoclonal antibody, a chimeric antibody, a humanized antibody, or a bispecific antibody. Additionally or alternatively, in some embodiments, antibody, or antigen binding fragment thereof binds to the ASIC1a protein. Additionally or alternatively, in some embodiments, the antibody or antigen binding fragment thereof binds an extracellular domain of ASIC1a. Additionally or alternatively, in some embodiments, the antibody or antigen binding fragment thereof binds an epitope that spans two ASIC1a subunits. Additionally or alternatively, in some embodiments, the antibody or antigen binding fragment thereof inhibits ASIC1a. Additionally or alternatively, in some embodiments, the antibody or antigen binding fragment thereof inhibits proton-induced ASIC1a currents.

In one aspect, the present technology provides a composition comprising the antibody of any embodiment disclosed herein. Additionally or alternatively, in some embodiments, the nucleic acid sequence is selected from the group consisting of SEQ ID NOs: 1, 6, 11, 16, 21, 26, 31, 36, 41, 46, 51, and 56.

In one aspect, the present technology provides a host cell or a vector expressing any nucleic acid disclosed herein.

In one aspect, the present technology provides a kit comprising the antibody, or antigen binding fragment thereof of any embodiment disclosed herein and instructions for use. Additionally or alternatively, in some embodiments, the antibody, or antigen binding fragment thereof of any embodiment disclosed herein is coupled to at least one detectable label selected from the group consisting of a radioactive label, a fluorescent label, and a chromogenic label. Additionally or alternatively, in some embodiments, the kit further comprises a secondary antibody that specifically binds to the antibody, or antigen binding fragment thereof of any embodiment disclosed herein.

In one aspect, the present technology provides a method for detecting ASIC1a protein in a biological sample comprising contacting the biological sample with the antibody, or antigen binding fragment thereof of any embodiment disclosed herein, conjugated to a detectable label; and detecting the presence and the level of the detectable label in the biological sample.

In some embodiments, the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and the $V_L$ CDR1 comprises an amino acid sequence set forth in SEQ ID NO: 8, $V_L$ CDR2 comprises an amino acid sequence set forth in SEQ ID NO: 9, and $V_L$ CDR3 comprises an amino acid sequence set forth in SEQ ID NO: 10.

In some embodiments, the $V_H$ CDR1 comprises an amino acid sequence set forth in SEQ ID NO: 13, $V_H$ CDR2 comprises an amino acid sequence set forth in SEQ ID NO: 14, and $V_H$ CDR3 comprises an amino acid sequence set forth in SEQ ID NO: 15; and the $V_L$ CDR1 comprises an amino acid sequence set forth in SEQ ID NO: 18, $V_L$ CDR2 comprises an amino acid sequence set forth in SEQ ID NO: 19, and $V_L$ CDR3 comprises an amino acid sequence set forth in SEQ ID NO: 20.

In some embodiments, the $V_H$ CDR1 comprises an amino acid sequence set forth in SEQ ID NO: 23, $V_H$ CDR2 comprises an amino acid sequence set forth in SEQ ID NO: 24, and $V_H$ CDR3 comprises an amino acid sequence set forth in SEQ ID NO: 25; and the $V_L$ CDR1 comprises an amino acid sequence set forth in SEQ ID NO: 28, $V_L$ CDR2 comprises an amino acid sequence set forth in SEQ ID NO: 29, and $V_L$ CDR3 comprises an amino acid sequence set forth in SEQ ID NO: 30.

In some embodiments, the $V_H$ CDR1 comprises an amino acid sequence set forth in SEQ ID NO: 33, $V_H$ CDR2 comprises an amino acid sequence set forth in SEQ ID NO: 34, and $V_H$ CDR3 comprises an amino acid sequence set forth in SEQ ID NO: 35; and the $V_L$ CDR1 comprises an amino acid sequence set forth in SEQ ID NO: 38, $V_L$ CDR2 comprises an amino acid sequence set forth in SEQ ID NO: 39, and $V_L$ CDR3 comprises an amino acid sequence set forth in SEQ ID NO: 40.

In some embodiments, the $V_H$ CDR1 comprises an amino acid sequence set forth in SEQ ID NO: 43, $V_H$ CDR2 comprises an amino acid sequence set forth in SEQ ID NO: 44, and $V_H$ CDR3 comprises an amino acid sequence set forth in SEQ ID NO: 45; and the $V_L$ CDR1 comprises an amino acid sequence set forth in SEQ ID NO: 48, $V_L$ CDR2 comprises an amino acid sequence set forth in SEQ ID NO: 49, and $V_L$ CDR3 comprises an amino acid sequence set forth in SEQ ID NO: 50.

In some embodiments, the $V_H$ CDR1 comprises an amino acid sequence set forth in SEQ ID NO: 53, $V_H$ CDR2 comprises an amino acid sequence set forth in SEQ ID NO: 54, and $V_H$ CDR3 comprises an amino acid sequence set forth in SEQ ID NO: 55; and the $V_L$ CDR1 comprises an amino acid sequence set forth in SEQ ID NO: 58, $V_L$ CDR2 comprises an amino acid sequence set forth in SEQ ID NO: 59, and $V_L$ CDR3 comprises an amino acid sequence set forth in SEQ ID NO: 60.

In some embodiments, the $V_H$ comprises an amino acid sequence selected from the group consisting of SEQ ID NOs: 2, 12, 22, 32, 42, and 52. In some embodiments, the $V_L$ comprises an amino acid sequence selected from the group consisting of SEQ ID NOs: 7, 17, 27, 37, 47 and 57.

The antibody or antigen binding fragment thereof (anti-ASIC1a antibodies of the present technology) may specifically bind ASIC1a protein. In some embodiments, the anti-ASIC1a antibodies of the present technology may bind the extracellular domain of ASIC1a. In some embodiments, the anti-ASIC1a antibodies of the present technology may bind an epitope that spans two ASIC1a subunits.

In some embodiments, the anti-ASIC1a antibodies of the present technology inhibit the function of ASIC1a trimer. In some embodiments, the anti-ASIC1a antibodies of the present technology stabilize ASIC1a trimer. In some embodiments, the anti-ASIC1a antibodies of the present technology inhibit heterooligomerization (e.g. heterotrimerization) of ASIC1a with other ASIC1 isomers.

In some embodiments, the antibody or antigen binding fragment thereof is an antibody, scFv, (scFv)$_2$, Fab, Fab', F(ab')$_2$ or an scFv-Fc antibody. In some embodiments, the antibody or antigen binding fragment thereof is an scFv antibody. In some embodiments, the scFv antibody is ASC01, ASC02, ASC03, ASC04, ASC05 or ASC06.

Formulations

By way of an example, anti-ASIC1a antibodies of the present technology is formulated in a simple delivery vehicle. However, anti-ASIC1a antibodies of the present technology may be lyophilized or incorporated in a gel, cream, biomaterial, sustained release delivery vehicle.

Anti-ASIC1a antibodies of the present technology are generally combined with a pharmaceutically acceptable carrier. The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids and amino acid copolymers. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like.

Modes of Administration and Effective Dosages

Any method known to those in the art for contacting a cell, organ or tissue with an immunoglobulin related composition of the present technology may be employed. Suitable methods include in vitro, ex vivo, or in vivo methods. In vivo methods typically include the administration of an anti-ASIC1a antibodies of the present technology, such as those described above, to a mammal, suitably a human. When used in vivo for therapy, the anti-ASIC1a antibodies of the present technology are administered to the subject in effective amounts (i.e., amounts that have desired therapeutic effect). The dose and dosage regimen will depend upon the degree of the symptoms in the subject, the characteristics of the particular anti-ASIC1a antibodies of the present technology used, e.g., its therapeutic index, the subject, and the subject's history.

The effective amount may be determined during preclinical trials and clinical trials by methods familiar to physicians and clinicians. An effective amount of the anti-ASIC1a antibodies of the present technology useful in the methods may be administered to a mammal in need thereof by any of a number of well-known methods for administering pharmaceutical compounds. The anti-ASIC1a antibodies of the present technology may be administered systemically or locally.

The immunoglobulin-related compositions described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

In some embodiments, immunoglobulin-related compositions described herein are administered by a parenteral route. In some embodiments, the antibody or antigen binding fragment thereof is administered by a topical route.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The anti-ASIC1a antibodies of the present technology compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the anti-ASIC1a antibodies of the present technology can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of anti-ASIC1a antibodies of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

An anti-ASIC1a antibody of the present technology can be formulated in a carrier system. The carrier can be a colloidal system. The colloidal system can be a liposome, a phospholipid bilayer vehicle. In one embodiment, the therapeutic anti-ASIC1a antibodies of the present technology is encapsulated in a liposome while maintaining the integrity of the anti-ASIC1a antibodies of the present technology. As one skilled in the art would appreciate, there are a variety of methods to prepare liposomes. (See Lichtenberg et al., Methods Biochem. Anal., 33:337-462 (1988); Anselem et al., Liposome Technology, CRC Press (1993)). Liposomal formulations can delay clearance and increase cellular uptake (See Reddy, Ann. Pharmacother., 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the anti-ASIC1a antibodies of the present technology can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, Ann. Pharmacother., 34(7-8):915-923 (2000)). A polymer formulation for human growth hormone (hGH) has been used in clinical trials. (See Kozarich and Rich, Chemical Biology, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the anti-ASIC1a antibodies of the present technology are prepared with carriers that will protect the anti-ASIC1a antibodies of the present technology against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The anti-ASIC1a antibodies of the present technology can also be formulated to enhance intracellular delivery. For example, liposomal delivery systems are known in the art, see, e.g., Chonn and Cullis, "Recent Advances in Liposome Drug Delivery Systems," Current Opinion in Biotechnology 6:698-708 (1995); Weiner, "Liposomes for Protein Delivery: Selecting Manufacture and Development Processes," Immunomethods, 4(3):201-9 (1994); and Gregoriadis, "Engineering Liposomes for Drug Delivery: Progress and Problems," Trends Biotechnol., 13(12):527-37 (1995). Mizguchi et al., Cancer Lett., 100:63-69 (1996), describes the use of fusogenic liposomes to deliver a protein to cells both in vivo and in vitro.

Dosage, toxicity and therapeutic efficacy of the anti-ASIC1a antibodies of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the anti-ASIC1a antibodies of the present technology exhibit high therapeutic indices. While anti-ASIC1a antibodies of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any anti-ASIC1a antibodies of the present technology used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the anti-ASIC1a antibodies of the present technology, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the anti-ASIC1a antibodies of the present technology ranges from 0.001-10,000 micrograms per kg body weight. In one embodiment, anti-ASIC1a antibodies of the present technology concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and until the subject shows partial or complete amelioration of symptoms of disease. Thereafter, the patient can be administered a prophylactic regime.

In some embodiments, a therapeutically effective amount of the anti-ASIC1a antibodies of the present technology may be defined as a concentration of the anti-ASIC1a antibodies of the present technology at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue. In some embodiments, the doses are administered by single daily or weekly administration, but may also include continuous administration (e.g., parenteral infusion or transdermal application). In some embodiments, the dosage of the anti-ASIC1a antibodies of the present technology is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h.

For example, a therapeutically effective amount may partially or completely alleviate one or more symptoms of ischemic stroke, including sudden weakness; paralysis or numbness of the face, arms, or legs, especially on one side of the body; drooping of one side of the face; confusion; difficulty with speaking, such as slurred words, or difficulty understanding speech; trouble seeing in one or both eyes, such as blurred or blackened vision, or double vision in one or both eyes; problems with breathing; dizziness; difficulty with walking; loss of balance or coordination, causing, e.g., unexplained falls; loss of consciousness, and sudden and severe headache. A therapeutically effective amount may partially or completely alleviate one or more symptoms of ischemic stroke, including, but not limited to, sudden-onset face weakness (such as drooping of one side) of the face, arm drift and abnormal speech.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In some embodiments, the mammal is a human.

Use of the Anti-ASIC1a Antibodies of the Present Technology

General. The anti-ASIC1a antibodies of the present technology are useful in methods known in the art relating to the localization and/or quantitation of ASIC1a protein or a mutant thereof (e.g., for use in measuring levels of the ASIC1a protein within appropriate physiological samples, for use in diagnostic methods, for use in imaging the polypeptide, and the like). The anti-ASIC1a antibodies of the present technology are useful to isolate a ASIC1a protein by standard techniques, such as affinity chromatography or immunoprecipitation. The anti-ASIC1a antibodies of the present technology can facilitate the purification of natural immunoreactive ASIC1a protein from biological samples, e.g., mammalian sera or cells as well as recombinantly-produced immunoreactive ASIC1a protein expressed in a host system. Moreover, anti-ASIC1a antibodies of the present technology can be used to detect an immunoreactive ASIC1a protein or a fragment thereof (e.g., in plasma, a cellular lysate or cell supernatant) in order to evaluate the abundance and pattern of expression of the immunoreactive polypeptide. The anti-ASIC1a antibodies of the present technology can be used diagnostically to monitor immunoreactive ASIC1a protein levels in tissue as part of a clinical testing procedure, e.g., to determine the efficacy of a given treatment regimen. As noted above, the detection can be facilitated by coupling (i.e., physically linking) the anti-ASIC1a antibodies of the present technology to a detectable substance.

Detection of ASIC1a protein. An exemplary method for detecting the presence or absence of an immunoreactive ASIC1a protein in a biological sample involves obtaining a biological sample from a test subject and contacting the biological sample with the anti-ASIC1a antibodies of the present technology capable of detecting an immunoreactive ASIC1a protein such that the presence of an immunoreactive ASIC1a protein is detected in the biological sample. Detection may be accomplished by means of a detectable label attached to the antibody.

The term "labeled" with regard to the anti-ASIC1a antibodies of the present technology is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-ASIC1a antibodies of the present technology disclosed herein are conjugated to one or more detectable labels. For such uses, the anti-ASIC1a antibodies of the present technology may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled ASIC1a-protein binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive ASIC1a protein in a biological sample in vitro as well as in vivo. In vitro techniques for detection of an immunoreactive ASIC1a protein include enzyme linked immunosorbent assays (ELISAs), Western blots, immunoprecipitations, radioimmunoassay, and immunofluorescence. Furthermore, in vivo techniques for detection of an immunoreactive ASIC1a protein include introducing into a subject a labeled anti-ASIC1a antibodies of the present technology. For example, the anti-ASIC1a antibodies of the present technology can be labeled with a radioactive marker whose presence and location in a subject can be detected by standard imaging techniques. In one embodiment, the biological sample contains ASIC1a protein molecules from the test subject.

Immunoassay and Imaging. The anti-ASIC1a antibodies of the present technology can be used to assay immunoreactive ASIC1a protein levels in a biological sample (e.g., human plasma) using antibody-based techniques. For example, protein expression in tissues can be studied with classical immunohistological methods. Jalkanen, M. et al., J. Cell. Biol. 101: 976-985, 1985; Jalkanen, M. et al., J. Cell. Biol. 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium (3H), indium ($^{112}$In), and technetium ($^{99}$mTc), and fluorescent labels, such as fluorescein, rhodamine, and green fluorescent protein (GFP), as well as biotin.

In addition to assaying immunoreactive ASIC1a protein levels in a biological sample, the anti-ASIC1a antibodies of the present technology may be used for in vivo imaging of ASIC1a protein. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-ASIC1a antibodies of the present technology by labeling of nutrients for the relevant scFv clone.

An anti-ASIC1a antibody of the present technology which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled the anti-ASIC1a antibodies of the present technology will then accumulate at the location of cells which contain the specific target polypeptide. For example, labeled the anti-ASIC1a antibodies of the present technology will accumulate within the subject in cells and tissues in which the ASIC1a protein has localized.

Thus, the present technology provides a diagnostic method of a medical condition, which involves: (a) assaying the expression of immunoreactive ASIC1a protein by measuring binding of the anti-ASIC1a antibodies of the present technology in cells or body fluid of an individual; (b) comparing the amount of immunoreactive ASIC1a protein present in the sample with a standard reference, wherein an increase or decrease in immunoreactive ASIC1a protein levels compared to the standard is indicative of a medical condition.

Affinity purification. The anti-ASIC1a antibodies of the present technology may be used to purify immunoreactive ASIC1a protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers, pp,* 4-12 (1995); Rothschild et al., *Nucl. Acids Res.,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hy-droxy-aminomethane.

Noncovalent Binding Association. An antibody or poly-peptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide contain-ing an attached trityl group or with a second solid support having hydrophobic character.

A solid support can also be provided with a member of a specific binding pair and, therefore, can be conjugated to a polypeptide or a second solid support containing a comple-mentary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific bind-ing pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of the Anti-ASIC1a Antibodies of the Present Technology

General. The anti-ASIC1a antibodies of the present tech-nology are useful in diagnostic methods. As such, the present technology provides methods using the antibodies in the diagnosis of ASIC1a protein activity in a subject. The anti-ASIC1a antibodies of the present technology may be selected such that they have any level of epitope binding specificity and very high binding affinity to a ASIC1a protein. In general, the higher the binding affinity of an antibody the more stringent wash conditions can be per-formed in an immunoassay to remove nonspecifically bound material without removing target polypeptide. Accordingly, the anti-ASIC1a antibodies of the present technology useful in diagnostic assays usually have binding affinities of about $108 \text{ M}^{-1}$, $10^9 \text{ M}^{-1}$, $10^{10} \text{ M}^{-1}$, $10^{11} \text{ M}^{-1}$ or $10^{12} \text{ M}^{-1}$. Further, it is desirable that the anti-ASIC1a antibodies of the present technology used as diagnostic reagents have a sufficient kinetic on-rate to reach equilibrium under standard condi-tions in at least 12 h, at least five (5) h, or at least one (1) hour.

The anti-ASIC1a antibodies of the present technology can be used to detect an immunoreactive ASIC1a protein in a variety of standard assay formats. Such formats include immunoprecipitation, Western blotting, ELISA, radioimmu-noassay, and immunometric assays. See Harlow & Lane, Antibodies, A Laboratory Manual (Cold Spring Harbor Publications, New York, 1988); U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of ASIC1a protein in a sample obtained from the subject. In certain embodiments, the sample is selected from the group con-sisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., the anti-ASIC1a antibodies of the present technology or a population of the anti-ASIC1a antibodies of the present technology immobilized to a solid phase, and another the anti-ASIC1a antibodies of the present technology or a population of the anti-ASIC1a antibodies of the present technology in solution. Typically, the solution the anti-ASIC1a antibodies of the present technology or popu-lation of the anti-ASIC1a antibodies of the present technol-ogy is labeled. If an antibody population is used, the population can contain antibodies binding to different epitope specificities within the target polypeptide. Accord-ingly, the same population can be used for both solid phase and solution antibody. If the anti-ASIC1a antibodies of the present technology are used, first and second ASIC1a pro-tein monoclonal antibodies having different binding speci-ficities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simul-taneously, the assay is referred to as a simultaneous assay. After contacting the ASIC1a protein with the anti-ASIC1a antibodies of the present technology, a sample is incubated for a period that usually varies from about 10 min to about 24 hr and is usually about 1 hr. A wash step is then performed to remove components of the sample not specifi-cally bound to the anti-ASIC1a antibodies of the present technology being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive ASIC1a protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the ASIC1a protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, the anti-ASIC1a antibodies of the present technology can be joined to a linker molecule, such as biotin for attachment to a surface bound linker, such as avidin.

In some embodiments, the present disclosure provides the anti-ASIC1a antibodies of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the ASIC1a protein antibodies of the present technology.

B. Therapeutic Use of the Anti-ASIC1a Antibodies of the Present Technology

General. In some aspects, the anti-ASIC1a antibodies of the present technology are useful in methods disclosed herein provide therapies for the prevention, amelioration or treatment of ischemic stroke and related conditions.

In one aspect, the present technology provides a method of treating ischemic stroke in a subject in need thereof, the method comprising: administering to the subject a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, 43, and 53; a $V_H$-CDR2 sequence of selected from the group consisting of: SEQ ID NOs: 4, 14, 24, 34, 44, and 54; and a $V_H$-CDR3 sequence selected from the group consisting of: SEQ ID NOs: 5, 15, 25, 35, 45, and 55; and the $V_L$ comprises an amino acid sequence selected from the group consisting of: a $V_L$-CDR1 sequence selected from the group consisting of: SEQ ID NOs: 8, 18, 28, 38, 48, and 58; a $V_L$-CDR2 sequence of selected from the group consisting of: SEQ ID NOs: 9, 19, 29, 39, 49, and 59; and a $V_L$-CDR3 sequence selected from the group consisting of SEQ ID NOs: 10, 20, 30, 40, 50, and 60.

In some embodiments, the $V_H$ comprises $V_H$ CDR1, $V_H$ CDR2, and $V_H$ CDR3, and the $V_L$ comprises $V_L$ CDR1, $V_L$ CDR2, and $V_L$ CDR3. In some embodiments, the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and the $V_L$ CDR1 comprises an amino acid sequence set forth in SEQ ID NO: 8, $V_L$ CDR2 comprises an amino acid sequence set forth in SEQ ID NO: 9, and $V_L$ CDR3 comprises an amino acid sequence set forth in SEQ ID NO: 10. In some embodiments, the $V_H$ CDR1 comprises an amino acid sequence set forth in SEQ ID NO: 13, $V_H$ CDR2 comprises an amino acid sequence set forth in SEQ ID NO: 14, and $V_H$ CDR3 comprises an amino acid sequence set forth in SEQ ID NO: 15; and the $V_L$ CDR1 comprises an amino acid sequence set forth in SEQ ID NO: 18, $V_L$ CDR2 comprises an amino acid sequence set forth in SEQ ID NO: 19, and $V_L$ CDR3 comprises an amino acid sequence set forth in SEQ ID NO: 20. In some embodiments, the $V_H$ CDR1 comprises an amino acid sequence set forth in SEQ ID NO: 23, $V_H$ CDR2 comprises an amino acid sequence set forth in SEQ ID NO: 24, and $V_H$ CDR3 comprises an amino acid sequence set forth in SEQ ID NO: 25; and the $V_L$ CDR1 comprises an amino acid sequence set forth in SEQ ID NO: 28, $V_L$ CDR2 comprises an amino acid sequence set forth in SEQ ID NO: 29, and $V_L$ CDR3 comprises an amino acid sequence set forth in SEQ ID NO: 30. In some embodiments, the $V_H$ CDR1 comprises an amino acid sequence set forth in SEQ ID NO: 33, $V_H$ CDR2 comprises an amino acid sequence set forth in SEQ ID NO: 34, and $V_H$ CDR3 comprises an amino acid sequence set forth in SEQ ID NO: 35; and the $V_L$ CDR1 comprises an amino acid sequence set forth in SEQ ID NO: 38, $V_L$ CDR2 comprises an amino acid sequence set forth in SEQ ID NO: 39, and $V_L$ CDR3 comprises an amino acid sequence set forth in SEQ ID NO: 40. In some embodiments, the $V_H$ CDR1 comprises an amino acid sequence set forth in SEQ ID NO: 43, $V_H$ CDR2 comprises an amino acid sequence set forth in SEQ ID NO: 44, and $V_H$ CDR3 comprises an amino acid sequence set forth in SEQ ID NO:

45; and the $V_L$ CDR1 comprises an amino acid sequence set forth in SEQ ID NO: 48, $V_L$ CDR2 comprises an amino acid sequence set forth in SEQ ID NO: 49, and $V_L$ CDR3 comprises an amino acid sequence set forth in SEQ ID NO: 50. In some embodiments, the $V_H$ CDR1 comprises an amino acid sequence set forth in SEQ ID NO: 53, $V_H$ CDR2 comprises an amino acid sequence set forth in SEQ ID NO: 54, and $V_H$ CDR3 comprises an amino acid sequence set forth in SEQ ID NO: 55; and the $V_L$ CDR1 comprises an amino acid sequence set forth in SEQ ID NO: 58, $V_L$ CDR2 comprises an amino acid sequence set forth in SEQ ID NO: 59, and $V_L$ CDR3 comprises an amino acid sequence set forth in SEQ ID NO: 60.

In some embodiments, the $V_H$ comprises an amino acid sequence selected from the group consisting of SEQ ID NOs: 2, 12, 22, 32, 42, and 52. In some embodiments, the $V_L$ comprises an amino acid sequence selected from the group consisting of SEQ ID NOs: 7, 17, 27, 37, 47 and 57.

In one aspect, the present technology provides alleviating one or more symptoms of ischemic stroke in a subject in need thereof, the method comprising: administering to the subject a therapeutically effective amount of an antibody or antigen binding fragment thereof comprising a heavy chain immunoglobulin variable domain ($V_H$) and a light chain immunoglobulin variable domain ($V_L$), wherein the $V_H$ comprises a $V_H$-CDR1 sequence selected from the group consisting of: SEQ ID NOs: 3, 13, 23, 33, 43, and 53; a $V_H$-CDR2 sequence of selected from the group consisting of: SEQ ID NOs: 4, 14, 24, 34, 44, and 54; and a $V_H$-CDR3 sequence selected from the group consisting of: SEQ ID NOs: 5, 15, 25, 35, 45, and 55; and the $V_L$ comprises an amino acid sequence selected from the group consisting of: a $V_L$-CDR1 sequence selected from the group consisting of: SEQ ID NOs: 8, 18, 28, 38, 48, and 58; a $V_L$-CDR2 sequence of selected from the group consisting of: SEQ ID NOs: 9, 19, 29, 39, 49, and 59; and a $V_L$-CDR3 sequence selected from the group consisting of: SEQ ID NOs: 10, 20, 30, 40, 50, and 60.

In some embodiments, the $V_H$ comprises $V_H$ CDR1, $V_H$ CDR2, and $V_H$ CDR3, and the $V_L$ comprises $V_L$ CDR1, $V_L$ CDR2, and $V_L$ CDR3. In some embodiments, the $V_H$ CDR1 comprises an amino acid sequence set forth in SEQ ID NO: 3, $V_H$ CDR2 comprises an amino acid sequence set forth in SEQ ID NO: 4, and $V_H$ CDR3 comprises an amino acid sequence set forth in SEQ ID NO: 5; and the $V_L$ CDR1 comprises an amino acid sequence set forth in SEQ ID NO: 8, $V_L$ CDR2 comprises an amino acid sequence set forth in SEQ ID NO: 9, and $V_L$ CDR3 comprises an amino acid sequence set forth in SEQ ID NO: 10. In some embodiments, the $V_H$ CDR1 comprises an amino acid sequence set forth in SEQ ID NO: 13, $V_H$ CDR2 comprises an amino acid sequence set forth in SEQ ID NO: 14, and $V_H$ CDR3 comprises an amino acid sequence set forth in SEQ ID NO: 15; and the $V_L$ CDR1 comprises an amino acid sequence set forth in SEQ ID NO: 18, $V_L$ CDR2 comprises an amino acid sequence set forth in SEQ ID NO: 19, and $V_L$ CDR3 comprises an amino acid sequence set forth in SEQ ID NO: 20. In some embodiments, the $V_H$ CDR1 comprises an amino acid sequence set forth in SEQ ID NO: 23, $V_H$ CDR2 comprises an amino acid sequence set forth in SEQ ID NO: 24, and $V_H$ CDR3 comprises an amino acid sequence set forth in SEQ ID NO: 25; and the $V_L$ CDR1 comprises an amino acid sequence set forth in SEQ ID NO: 28, $V_L$ CDR2 comprises an amino acid sequence set forth in SEQ ID NO: 29, and $V_L$ CDR3 comprises an amino acid sequence set forth in SEQ ID NO: 30. In some embodiments, the $V_H$ CDR1 comprises an amino acid sequence set forth in SEQ ID NO: 33, $V_H$ CDR2 comprises an amino acid sequence set forth in SEQ ID NO: 34, and $V_H$ CDR3 comprises an amino acid sequence set forth in SEQ ID NO: 35; and the $V_L$ CDR1 comprises an amino acid sequence set forth in SEQ ID NO: 38, $V_L$ CDR2 comprises an amino acid sequence set forth in SEQ ID NO: 39, and $V_L$ CDR3 comprises an amino acid sequence set forth in SEQ ID NO: 40. In some embodiments, the $V_H$ CDR1 comprises an amino acid sequence set forth in SEQ ID NO: 43, $V_H$ CDR2 comprises an amino acid sequence set forth in SEQ ID NO: 44, and $V_H$ CDR3 comprises an amino acid sequence set forth in SEQ ID NO: 45; and the $V_L$ CDR1 comprises an amino acid sequence set forth in SEQ ID NO: 48, $V_L$ CDR2 comprises an amino acid sequence set forth in SEQ ID NO: 49, and $V_L$ CDR3 comprises an amino acid sequence set forth in SEQ ID NO: 50. In some embodiments, the $V_H$ CDR1 comprises an amino acid sequence set forth in SEQ ID NO: 53, $V_H$ CDR2 comprises an amino acid sequence set forth in SEQ ID NO: 54, and $V_H$ CDR3 comprises an amino acid sequence set forth in SEQ ID NO: 55; and the $V_L$ CDR1 comprises an amino acid sequence set forth in SEQ ID NO: 58, $V_L$ CDR2 comprises an amino acid sequence set forth in SEQ ID NO: 59, and $V_L$ CDR3 comprises an amino acid sequence set forth in SEQ ID NO: 60.

In one aspect, the present technology provides a method for treating ischemic stroke in a subject in need thereof, comprising administering to the subject a therapeutically effective amount of an antibody or antigen binding fragment thereof comprising (a) a light chain immunoglobulin variable domain sequence that is at least 80%, at least 85%, at least 90%, at least 95%, or at least 99% identical to the light chain immunoglobulin variable domain sequence of any one of SEQ ID NOs: 7, 17, 27, 37, 47, or 57; and/or (b) a heavy chain immunoglobulin variable domain sequence ($V_H$) that is at least 80%, at least 85%, at least 90%, at least 95%, or at least 99% identical to the heavy chain immunoglobulin variable domain sequence present in any one of SEQ ID NOs: 2, 12, 22, 32, 42, or 52.

In some embodiments, the antibody or antigen binding fragment thereof binds ASIC1a protein. In some embodiments, the antibody or antigen binding fragment thereof binds the extracellular domain of ASIC1a. In some embodiments, the antibody or antigen binding fragment thereof binds an epitope that spans two ASIC1a subunits. In some embodiments, the antibody or antigen binding fragment thereof inhibits the function of ASIC1a trimer.

In some embodiments, the one or more symptoms of ischemic stroke is sudden weakness; paralysis or numbness of the face, arms, or legs, especially on one side of the body; drooping of one side of the face; confusion; difficulty with speaking, such as slurred words, or difficulty understanding speech; trouble seeing in one or both eyes, such as blurred or blackened vision, or double vision in one or both eyes; problems with breathing; dizziness; difficulty with walking; loss of balance or coordination, causing, e.g., unexplained falls; loss of consciousness, and sudden or severe headache. In some embodiments, the one or more symptoms of ischemic stroke is selected from the group consisting of sudden-onset face weakness (such as drooping of one side of the face), arm drift and abnormal speech.

In some embodiments, the antibody or antigen binding fragment thereof is an antibody, scFv, (scFv)$_2$, Fab, Fab', F(ab')$_2$ or an scFv-Fc antibody. In some embodiments, the antibody or antigen binding fragment thereof is an scFv antibody. In some embodiments, the scFv antibody is ASC01, ASC02, ASC03, ASC04, ASC05 or ASC06.

Thus, for example, one or more the anti-ASIC1a antibodies of the present technology may be: (1) co-formulated and administered or delivered alone or simultaneously in a combined formulation with other active agents or the anti-ASIC1a antibodies of the present technology; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. Administering such combinations of the anti-ASIC1a antibodies of the present technology and other active agents can result in synergistic biological effect when administered in a therapeutically effective amount to a subject suffering from a medical disease or condition and in need of treatment. An advantage of such an approach is that lower doses of the anti-ASIC1a antibodies of the present technology and/or other active agents may be needed to prevent, ameliorate or treat a subject suffering from, or predisposed to, ischemic stroke in a subject. Further, potential side-effects of treatment may be avoided by use of lower dosages of the anti-ASIC1a antibodies of the present technology and/or other active agents.

The anti-ASIC1a antibodies of the present technology are described herein such as ASC01, ASC02, ASC03, ASC04, ASC05, ASC06, etc. are useful to prevent or treat disease. Specifically, the disclosure provides for both prophylactic and therapeutic methods of treating a subject suffering from, or predisposed to, ischemic stroke. Accordingly, the present methods provide for the prevention and/or treatment a subject suffering from, or predisposed to, ischemic stroke in a subject by administering to the subject an effective amount of the anti-ASIC1a antibodies of the present technology to a subject in need thereof to restore of the function of the mutant the ion channel protein trimer. The present technology provides the treatment of a subject suffering from, or predisposed to, ischemic stroke in mammals through administration of therapeutically effective amounts of the anti-ASIC1a antibodies of the present technology as disclosed herein, such as ASC01, ASC02, ASC03, ASC04, ASC05, ASC06, etc. to subjects in need thereof.

Determination of the Biological Effect of the Anti-ASIC1a Antibodies of the Present Technology.

In various embodiments, suitable in vitro or in vivo assays are performed to determine the effect of a specific therapeutic based on the anti-ASIC1a antibodies of the present technology and whether its administration is indicated for treatment. In various embodiments, in vitro assays can be performed with representative cell lines, CHO-K1 cells, such as the CHO-K1/hASIC1a (a stable cell line overexpressing the full-length hASIC1a) disclosed herein. These experiments may be used to determine if a given anti-ASIC1a antibodies of the present technology exerts the desired effect in inhibiting the activity of ASIC1a protein trimers. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

In some embodiments, the ASIC1a activity is determined by assays well known in the art, including, but not limited to electrophysiological assays such as patch clamp, as disclosed herein. In some embodiments, the ASIC1a activity is determined by assays that measure biological activity in animal models. In some embodiments, the ASIC1a activity is determined by assays that measure the rescue of disease phenotype of the animal models, including, but not limited to the mouse middle cerebral artery occlusion (MCAO)-induced ischemic stroke model, disclosed herein.

Modes of Administration and Effective Dosages

Any method known to those in the art for contacting a cell, organ or tissue with an immunoglobulin related composition of the present technology may be employed. Suitable methods include in vitro, ex vivo, or in vivo methods. In vivo methods typically include the administration of an immunoglobulin-related composition, such as those described above, to a mammal, suitably a human. When used in vivo for therapy, the anti-ASIC1a antibodies of the present technology are administered to the subject in effective amounts (i.e., amounts that have desired therapeutic effect). The dose and dosage regimen will depend upon the degree of the symptoms in the subject, the characteristics of the particular immunoglobulin used, e.g., its therapeutic index, the subject, and the subject's history.

The effective amount may be determined during preclinical trials and clinical trials by methods familiar to physicians and clinicians. An effective amount of an immunoglobulin useful in the methods may be administered to a mammal in need thereof by any of a number of well-known methods for administering pharmaceutical compounds. The immunoglobulin may be administered systemically or locally.

C. Kits

The present technology provides kits for the detection and/or treatment of ischemic stroke, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of ischemic stroke. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive ASIC1a protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-ASIC1a antibodies of the present technology (or antigen binding fragments thereof) capable of binding a ASIC1a protein in a biological sample; means for determining the amount of the ASIC1a protein in the sample; and means for comparing the amount of the immunoreactive ASIC1a protein in the sample with a standard. One or more of the anti-ASIC1a antibodies may be labeled. The kit components, (e.g., reagents) can be packaged in a suitable container. The kit can further comprise instructions for using the kit to detect the immunoreactive ASIC1a protein.

For antibody-based kits, the kit can comprise, e.g., 1) a first antibody, e.g. a humanized, or chimeric anti-ASIC1a antibody of the present technology (or an antigen binding fragment thereof), attached to a solid support, which binds to a ASIC1a protein; and, optionally; 2) a second, different antibody which binds to either the ASIC1a protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a ASIC1a protein in vitro or in vivo, or for treatment of ischemic stroke in a subject in need thereof. In certain embodiments, the use of the reagents can be according to the methods of the present technology.

EXAMPLES

The present technology is further illustrated by the following examples, which should not be construed as limiting in any way. For each of the examples below, any immunologic binding agent, such as IgG, IgM, IgA, IgD, IgE, and genetically modified IgG, and fragments thereof described herein could be used. By way of example, but not by limitation, the scFv or IgG1 antibodies used in the examples below could be ASC01, ASC02, ASC03, ASC04, ASC05 or ASC06, etc.

Example 1: Materials and Methods

Reagents and Abbreviations. All of the reagents were purchased from Sigma or as otherwise stated at the highest analytical grades. The recombinant protein symbols are used in the format where an italicized lowercase letter of the initial of species (e.g., human, mouse, rat, etc.) is used as the first letter in the symbol followed by the gene name (e.g., hASIC1a represents the hASIC1a protein). Antibodies were arbitrarily numbered like ASC00, according to the panning results. The arbitrary number with or without the "-IgG1" symbol represents the antibody in the format of scFv fused with Fc or full-length IgG1 (IgG1), respectively.

Cell Culture. The CHO-K1 cell line (#CRL-9618; ATCC) was maintained in an F-12k media (#21127022; Gibco) containing 10% (vol/vol) FBS (#1600074; Gibco), whereas the FreeStyle 293F (#R79007; ThermoFisher Scientific) cell line was cultured in a Freestyle 293 expression media (#12338026; Thermo-Fisher Scientific). *Spodoptera fru-giperda* 9 (Sf9) cells (#12659017; Thermo-Fisher Scientific) was cultured at 27° C. in an ESF921 media (#96-001-01; Expression Systems). Primary cortical neurons dissected from E18-d-old C57 BL/6 mice or ASIC1a$^{-/-}$ mice were maintained in a Neurobasal media (#21103049; Gibco) supplemented with B27 (#17504044; Gibco) and Glutamx I (#35050061; Gibco). The CHO-K1/hASIC1a stable cell line overexpressing the full-length hASIC1a (1-528 amino acids) channel was generated as follows: The cDNA of the full-length hASIC1a with a C-terminal eYFP fusion or a C-terminal mCherry fusion was constructed, cloned into a pCDNA3.1-Neo expressing vector, and transfected into the CHO-K1 cells using Lipofectin 2000. The CHO-K1/ hASIC1a stable cell line was selected by the antibiotic, geneticin (up to 1 mg/mL), and validated by the fused fluorescence proteins eYFP ($\lambda_{ex}$=488 nm; $\lambda_{em}$=528 nm) or mCherry fluorescence ($\lambda_{ex}$=587 nm; $\lambda_{em}$=610 nm) using flow cytometry. Over 80% positive cells survived when cultured in the presence of 200 g/mL geneticin for 30 days. The clonal stable lines were sorted using a flow cytometry instrument (BD FACSAria III) based on the expression of eYFP (6H7 cell line) and mCherry (4C12 cell line) and expanded using an F-12K media supplemented with 10% (vol/vol) FBS and 200 µg/mL geneticin. The hASIC1a-specific monoclonal antibody, ASC06, was used to further confirm the overexpression of hASIC1a.

Purification of Recombinant Truncated hASIC1a. The cDNA encoding the truncated hASIC1a (ΔhASIC1a) fused to an N-terminal Flag-tag was cloned into a pEG BacMam expression vector (courtesy of Eric Gouaux, Howard Hughes Medical Institute, Oregon Health and Science University, Portland, OR). The ΔhASIC1a protein was then heterologously expressed in the HEK293F cells using the BacMam system. Goehring, et al., Nat Protoc 9:2574-2585 (2014). In brief, the pEG BacMam-ΔhASIC1a construct was transformed into the DH10Bac *Escherichia coli* cells (ΔhASIC1a bacmids). The resulting bacmids were then transfected into the Sf9 cells using the FuGENE transfection reagent (Promega) to obtain the P3 baculovirus (amplified twice). The HEK293F cells ($2 \times 10^6$ cells per mL) were infected by the baculovirus at the multiplicity of infection (MOI) of 1:25 (virus:cell) for 24 h at 37° C. The infected cells were incubated in the presence of 2 mM sodium butyrate at 37° C. for 48 h to boost the expression of the target protein. Cells were harvested by centrifugation at 2,000×g per 1 min.

Figure 12A:
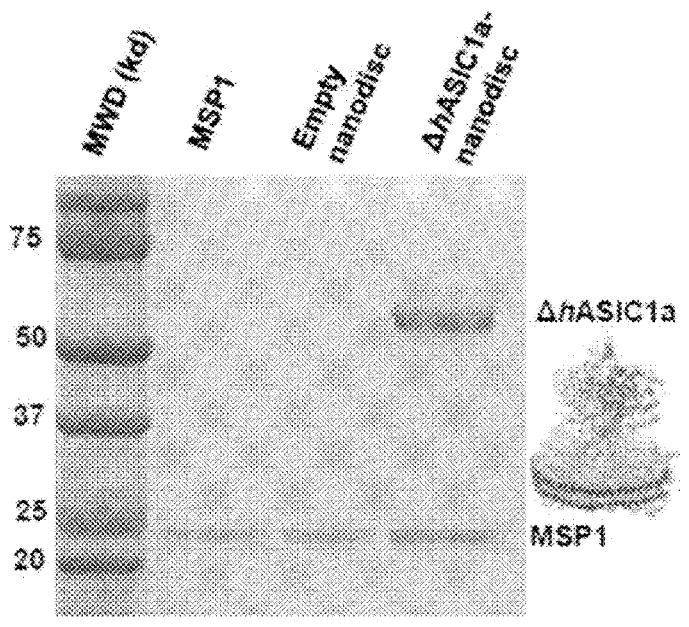

The following steps were carried out on ice unless specified otherwise. The cell pellet from a 2 L culture was first resuspended in 100 mL of a hypotonic buffer (10 mM Tris, pH 7.5, 10 mM MgCl$_2$, 20 mM KCl) supplemented with the protease inhibitor mixture (one tablet per 50 mL; Roche). The cells were ground using a Dounce homogenizer, and centrifuged at 80,000×g for 40 min. After repeating the process once, the resulting pellets were resuspended in 100 mL of a hypertonic buffer (10 mM Tris, pH 7.5, 10 mM MgCl$_2$, 20 mM KCl, 1 M NaCl), homogenized, and centrifuged. This procedure was also repeated one more time. The resulting pellets were then mixed and treated with 2 mg/mL iodoacetamide in a 50 mL hypotonic buffer containing protease inhibitors for 30 min. The recombinant ΔhASIC1a protein was extracted in the cell lysis buffer (100 mM Tris, pH 7.5, 1.6 M NaCl, 1% n-dodecyl b-D-maltopyranoside (DDM), 0.2% cholesteryl hemisuccinate (CHS)) under gentle agitation at 4° C. for 3 h. After 30 min of centrifugation at 15,000×g, supernatant was incubated with the anti-FLAG M2 magnetic beads (#M8823; Sigma) overnight under gentle agitation. The magnetic beads were washed once each with buffer A (50 mM Tris, pH 7.5, 800 mM NaCl, 10% glycerol, 0.1% DDM, 0.02% CHS, 10 mM $MgCl_2$) and buffer B (25 mM Tris, pH 7.5, 800 mM NaCl, 10% glycerol, 0.05% DDM, 0.01% CHS). The ΔhASIC1a protein was eluted using the buffer B supplemented with 0.1 mg/mL Flag peptide, concentrated, further purified using the SEC on a Superdex 200 column (GE Healthcare), and concentrated to yield 60 μL of 15 mg/mL stock solution. As shown in FIG. 12A, the resultant homogeneous ΔhASIC1a was >90% pure as judged by SDS-PAGE analysis.

Nanodisc Assembly of hASIC1a Channel. To mimic the lipid bilayer environment of cellular membranes, the purified ΔhASIC1a protein was incorporated into a lipid nanodisc by mixing the ΔhASIC1a protein with the membrane scaffold protein (MSP). and 1,2-dimyristoyl-sn-glycero-3-phosphocholine (DMPC) at a molar ratio of 3:2:65. The associated detergents were removed by gentle agitation with the Bio-Beads SM2 [Bio-Beads:DDM=10:1 (wt/wt); Bio-Rad]overnight. The ΔhASIC1a-embedded nanodiscs were separated from the unassembled nanodisc using the Flag peptide-specific magnetic beads. D'Antona et al., *Biochemistry* 53:127-134 (2014). The desired ΔhASIC1a nanodisc assembly was further purified and collected using a Superose 6 column (GE Healthcare) in a buffer containing 20 mM Tris, pH 7.5, and 150 mM NaCl. The empty nanodiscs were packaged without the addition of ΔhASIC1a. The composition of the assembled ΔhASIC1a nanodiscs was analyzed by SDS-PAGE, EM, and dynamic light scattering (FIGS. 9A-C, 12A, 12B)

Differential Enrichment-Based Screening of Combinatorial Antibody Library. The hASIC1a-specific scFv antibodies were selected from a combinatorial human monoclonal scFv antibody phage library ($10^{11}$ diversity) after three rounds of affinity enrichment against the biotinylated ΔhASIC1a nanodiscs immobilized on the streptavidin-coated magnetic beads (#21925; Pierce). The phage antibody library panning was performed using a modified procedure. Xu, et al. *Front Mol Neurosci* 10: 298 (2017). Briefly, phagemids (displaying the antibody library) binding to the antigen (ΔhASIC1a nanodiscs) were enriched at each cycle and eluted with Glycine-HCl (pH 2.2). The XL1-Blue cells were used to express and amplify the output phagemids for the next rounds of panning. To minimize nonspecific enrichment, a differential enrichment phage display selection was used, in which excessive amounts of the empty nanodiscs (two times above the amount of ΔhASIC1a nanodiscs) were used to pull down the nonspecific phagemids before panning against the ΔhASIC1a nanodiscs in the second and third cycles. After three iterations, 96 positive colonies were selected and analyzed by phage ELISA. Xu, et al. *Front Mol Neurosci* 10: 298 (2017). All of the positive clones were sequenced. Both the DNA and protein sequences of CDR3 domains were analyzed using the international ImMunoGeneTics information platform. A phylogenetic tree was constructed after aligning of the CDR3 sequences. Six distinctive scFv sequences were highly enriched.

Expression and Purification of Antibodies. Genes encoding the candidate scFv sequences were cloned into a modified pFUSE expression vector (#pfuse-hg1fc2; Invivogen) to obtain the scFv-Fc fusion protein constituting the entire Fc domain of human IgG1. For the full-length IgG1 antibody, variable regions of heavy chain ($V_H$ domain) and light chain ($V_L$ domain) from the scFv vector were cloned to plasmids with intact constant heavy chain domain ($CH_1$, $CH_2$ and $CH_3$) and intact constant light chain domain ($C_L$), respectively. The HEK293F cells transfected with the scFv-Fc vectors or cotransfected with equal molar of heavy-chain vectors and light-chain vectors were cultured for 4 d. After centrifugation, the scFv-Fc or full-length IgG1 antibodies secreted into the media were purified using a HiTrap Protein A HP column (#17-0403-03; GE Healthcare) with a citrate elution buffer, pH 3.4, on an AKTA purifier 100 (GE Healthcare). The purified antibodies were then concentrated (15 mg/mL) and stored in a PBS buffer, pH 7.4, at −80° C. As shown, e.g., in FIG. 12D, SDS-PAGE analysis showed that the purified single chain and full length antibodies were at least 90% pure.

Figure 14:
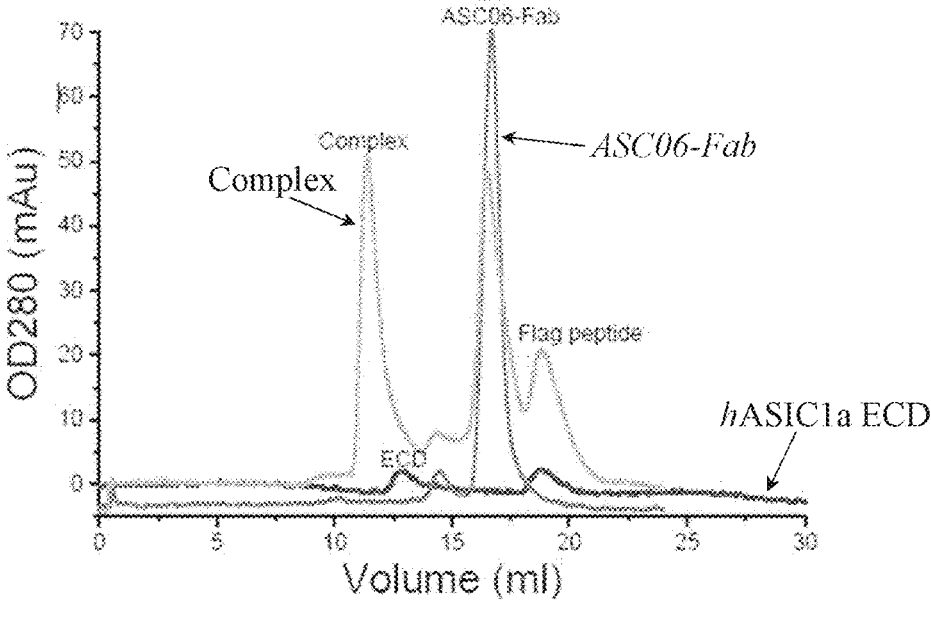
FIG. 14 shows the gel filtration profile of the complex assembled by hASIC1a-ECD and ASC06-Fab. The gel filtration profiles of hASIC1a-ECD alone, ASC06-Fab alone and the complex are shown. Superdex 200 size exclusion chromatography column was used (24 mL volume).

Negative Stain Electron Microscopy (EM): (1) Sample Preparation and Data Collection. The antigen-binding fragment of ASC06-IgG1 (ASC06-Fab) was prepared by digesting ASC06-IgG1 with papain followed by protein A affinity purification and gel filtration. The ectodomain of hASIC1a (hASIC1a-ECD) with an N-terminal fused IL-2 tag and Flag tag was expressed in HEK293F cells and purified by anti-Flag M2 magnetic beads and gel filtration using PBS buffer, pH 7.4. The ASC06-Fab and hASIC1a-ECD were incubated at a molar ratio of 3:1 in PBS buffer, pH 7.4, overnight at 4° C. to form a tertiary complex. This complex was further isolated by gel filtration. As shown in FIG. 14, the complex formed a distinct peak, which was distinguishable both from ASC06-Fab alone and hASIC1a-ECD alone. The peak fractions containing this complex were collected and subjected to negative staining EM.

The EM samples were prepared by diluting the purified complex of hASIC1a-ECD and ASC06-Fab to 0.01 mg/mL. Then, 4-μL sample droplets were absorbed for 1 min on freshly glow-discharged copper grids covered by a thin and continuous carbon film (#BZ31024a; Beijing Zhongjingkeyi Technology). The grids were washed with two drops of deionized water, subsequently negatively stained with two drops of 0.75% (wt/vol) uranyl formate (#22450; Electron Microscopy Sciences) for 1 min before blotting with filter papers, and then, air dried.

All micrographs were recorded with a Tecnai G2 Spirit transmission electron microscope (FEI) equipped with an $LaB_6$ cathode operated at 120 kV and a 4,000×4,000 Eagle CCD camera at a calibrated magnification of 67,000 times, resulting in a pixel size of 1.74 Å.

EMI mage Processing and 3D Reconstruction. The Scipion software suite was used for all image processing steps. de la Rosa-Trevin et al., *J Struct Biol* 157:38-46 (2016). All of the recorded micrographs were first decimated twofold (resulting in a pixel size of 3.48 Å). Then, a total of 5,064 particles were manually selected from 100 micrographs with the EMAN2 Boxer function using a box size of 96×96 pixels. Tang et al., *J Struct Biol.* 157(1):38-46 (2007). Reference-free 2D class averages analyses was generated using the Xmipp CL2D function. de la Rosa-Trevin et al., *J Struct Biol* 184:321-328. (2013).

Molecular Dynamics Simulation. The models for the hASIC1a and for the ASC06 in Fab format were derived by homology by using the Swiss Model website. Biasini et al. *Nucleic Acids Res* 42:W252-W258 (2014). The template for ASIC1a proteins was obtained from the structure of the truncated chicken protein [Protein Data Bank (PDB) ID code 4FZ0]. To compare the negative staining results with a possible atomistic model, a series of different possible dockings of the Fab to the ECD of the hASIC1a (only residues 73-425 were kept) was first generated using the ClusPro 2.0 server and the antibody docking mode. Comeau et al., *Bioinformatics* 28:2608-2614SR (2004); and Brenke et al., *Bioinformatics* 28(20):2608-14 (2012). Eight of the dockings of the Fab to the ECD of the hASIC1a with geometry that was more compatible with the one described by the negative staining were then subselected and energy minimization was performed followed by 20-ns molecular dynamics simulation to relax the interaction and stabilize the structure of the complex. After this procedure, only one model seemed to satisfy the overall geometry that is experimentally observed in negative staining experiments. Simulations were performed using the Gromacs 4.6.7 package and the Amber14ffSB force field. Pronk et al., *Bioinformatics* 29: 845-854 (2013); and Lindorff-Larsen et al., *Proteins* 78: 1950-1958 (2010). All of the systems were solvated with full-atom TIP3P water containing $Cl^-$ and $K^+$ ions at a concentration of ~0.15 M to mimic a physiological ionic strength.

Temperature T and pressure P were kept constant at 300 K and 1 atm, respectively, using the Berendsen thermostat and barostat. Berendsen et al., *J Chem Phys* 81:3684-3690 (1984). Fast smooth Particle-Mesh Ewald summation was used for long-range electrostatic interactions, with a cutoff of 1.0 nm for the direct interactions. Darden et al., *J Chem Phys* 98:10089-10093 (1993).

As shown in FIG. 12A, the model of the ASIC1a inserted in the nanodisc was obtained starting from the crystal structure of MSP1 protein (PDB ID code 2MSC) in complex with the ASIC1a trimer and filled with 91 DMPC molecules.

ELISA assays. Avidin (#21121; Pierce) was diluted to a final concentration of 2 ng/μL in the Carbonate-Bicarbonate buffer (#C3041; Sigma). The resulting avidin solution was used to coat the 96-well plates (25 μL per well) at 4° C. overnight. The coated plates were washed once with phosphate buffered solution containing 0.05% Tween-20 (PBST) (150 μL per well) followed by the addition and incubation of 25 μL biotinylated ΔhASIC1a nanodisc solution (2 ng/μL) in each well at 37° C. for 1 h. The PBST buffer alone and the empty nanodisc solution (2 ng/μL) were used as the background and negative controls, respectively. After removal of the incubation solution, the resulting plates were rinsed once using the PBST buffer and incubated with a blocking solution containing 5% (vol/vol) milk in PBST (150 μL per well) at 37° C. for 1 h. After blocking and PBST washing (one time), 25 μL of the scFv-Fc antibody solution (10 g/mL in PBST containing 1% (vol/vol) milk) was added to each well and incubated at 37° C. for 1 h. The resulting plates were rinsed eight times using PBST before subjecting to HRP detection. A solution containing the goat anti-human Fc HRP-conjugated secondary antibody (dilution factor 1:5, 000; #A0170; Sigma) and the anti-M13 HRP-conjugated secondary antibody (dilution factor 1:5,000; #27-9421-01; GE/Amersham/Whatman) was added into the above plates (50 μL per well) and incubated at 37° C. for 1 h. The plates were then washed eight times with PBST followed by the addition of 50 μL 2,2'-azinobis [3-ethylbenzothiazoline-6-sulfonic acid]-diammonium salt solution (#11684302001;

Roche) into each well. After 20 min of incubation at room temperature, the absorption changes at 405 nm in each well were measured on a microplate reader (Enspire; PerkinElmer).

Affinity Determination. Surface plasmon resonance (SPR) and flow cytometry were used to study the interaction between the monoclonal antibody and hASIC1a. SPR-binding studies were performed on a Biacore T200 (GE Healthcare). The anti-Flag antibody was amine coupled to the surface of a biosensor chip CM5 series S (GE Healthcare). The recombinant Flag-tagged ΔhASIC1a was then immobilized onto the chip surface. Serially diluted antibody ASC06-IgG1 (1, 5, 10, 50, 100 nM) was applied in a running buffer (pH 7.4) containing 25 mM HEPES, 500 mM NaCl, 0.05% EDTA, and 0.05% DDM. The kinetics of binding/dissociation was measured as a change in the SPR signal resonance units. Apparent binding affinities were calculated using the Biacore T200 evaluation software with a single-cycle kinetic model.

In the flow cytometry-binding experiments, ASIC1a-eYFP-expressing stable cells (6H7) were collected and resuspended in ice cold FACS buffer (PBS, 0.05% BSA, 2 mM EDTA). Equal numbers of 6H7 cells (50,000 cells per tube) were then incubated with different concentrations of ASC06-IgG1 for 20 min at 4° C., washed with 1 mL ice cold FACS buffer, centrifuged, and pellets were resuspended in 100 μL ice cold FACS buffer containing the Alexa555-conjugated secondary antibody that recognizes human Fc (1:800 (vol/vol) dilution; Life Technology). After incubating at 4° C. for 15 min, the cells were washed twice and resuspended in the FACS buffer. Cells were sorted and analyzed on a flow cytometer (CytoFLEX S; Beckman Culter) to determine relative binding level by the antibodies to the stable cell lines overexpressing hASIC1a. Mean fluorescent intensities of Alexa555 in eYFP-positive cells were recorded and analyzed to calculate the apparent binding affinity of antibody.

Cell Membrane Colocalization Studies Using Immunocytochemistry (ICC). Cells (CHO-K1) were seeded onto the poly-D-lysine-coated glass bottom 24-well plates at a concentration of $2 \times 10^5$ cells per mL. After 12 h of cultivation, the CHO-K1 cells were transfected with ASIC plasmids by Lipofectin 3000 reagent. Twenty-four hours after transfection, the cells were fixed in 4% paraformaldehyde and incubated for 30 min in a blocking solution (5% goat serum in PBS). The resulting cells were incubated with 2 g/mL ASC06-IgG1 at 4° C. overnight followed by three PBS washes for 5 min each and incubation with the Alexa555-conjugated goat anti-human secondary antibody (Life Technology). After three additional PBS washes for 5 min each, the nuclei of the cells were stained with DAPI (#10236276001; Roche). The ICC analysis was performed on a laser scanning confocal microscopy (ZEISS LSM710) with a 63×N.A. 1.4 objective at 25° C. Images were collected on a 1,024×1,024-pixel EM-CCD camera. Data acquisition and analyses were performed with the ZEN 2012 professional software.

Electrophysiological Experiments. The inward cellular ASIC1a current was recorded from a single cell using standard whole-cell recording techniques by a patch-clamp amplifier (Axon 200B; Axon Instruments). Membrane currents were sampled and analyzed using a Digidata 1320A interface and a personal computer with Clampex and Clampfit software (Version 9.0.1; Axon Instruments). For a typical experiment, the extracellular fluid (ECF) used contained 150 mM NaCl, 5 mM KCl, 10 mM HEPES, 10 mM D-glucose, 2 mM $CaCl_2$, and 1.0 mM $MgCl_2$, with the osmotic pressure in the range of 320-335 mOsm, and pH 7.4 adjusted with 5 M NaOH. Patch electrodes (4-6 MΩ) contained 30 mM NaCl, 120 mM KCl, 0.5 mM CaCl$_2$, 1 mM MgCl$_2$, 10 mM HEPES, 2 mM MgATP, and 5 mM EGTA (pH 7.2 adjusted with 5 M KOH) at 300 mOsm. The ASIC1a activating ECF is identical to the normal ECF, except that MES was used to replace HEPES to maintain the ECF at pH 6.0. A coverslip with discretely distributed individual CHO-ASIC1a stable cells (6H7) on the surface was placed into a recording chamber under a constant perfusion (~2-3 mL/min) generated by an ALA 8 channel perfusion system (ALA Scientific Instruments Inc.) mounted on an inverted microscope. After achieving the break-in (whole-cell) configuration, the cell was voltage clamped at a holding potential of −70 mV. The normal ECF (pH 7.4) was first perfused onto the patched cell, and then, the activating ECF of pH 6.0 was rapidly applied to elicit a maximum inward ASIC1a current as control current. When testing the inhibition effect of the antibody, ECFs of pH 7.4 containing different concentrations of ASC06-IgG1 were perfused from low to high concentration into the recording chamber for 10-15 min. To measure the inhibition of the current, the activating ECFs of pH 6.0 containing the corresponding concentrations of the testing antibodies were applied to the same patched 6H7 cell to generate the inward currents that can be normalized to the control current of the same cell. The small molecule inhibitor amiloride (#S1811; Selleck) and the venom peptide PcTx1 (#4435s; Peptide Institute) at concentrations of 30 M and 100 nM, respectively, were used as the positive controls for the inhibition of the ASIC1a current. Data acquired from four to five cells were used for statistical calculation of inhibition effects.

For the measurement of steady-state desensitization (SSD), the pH of the conditioning ECF was adjusted to 7.6, 7.4, 7.2, 7.0, and 6.8 (in a HEPES buffer), while the activating ECF was maintained at pH 6.0 (in an MES buffer). For the measurement of pH activation of the hASIC1a in the 6H7 stable cells, the conditioning ECF was fixed at pH 7.6 (in a HEPES buffer), and the pH of the activating ECF was adjusted to 7.4, 7.2, 7.0, 6.8, 6.5, 6.3, and 6.0. The hASIC1a currents were recorded when the stable cell line 6H7 was patched in the presence and absence of 300 nM ASC06-IgG1. The relative currents expressed as fractions of the maximum amplitude on the sensorgram (I/Imax) were calculated and plotted to constitute SSD and pH activation profiles. Each data point represents the average of at least five patched cells.

Calcium Influx. The FLIPR Calcium 5 Assay kit was used to determine the acid-induced calcium influx in the hASIC1a-mCherry-expressing stable CHO-K1 cells (4C12). Cells were seeded in a clear bottom 96-well plate at a density of 10,000 per well 24 h before assay. Assay buffer and dye loading buffer (1.26 mM CaCl$_2$, 0.5 mM MgCl$_2$, 0.4 mM MgSO$_4$, 5.33 mM KCl, 0.44 mM KH$_2$PO$_4$, 4.17 mM NaHCO$_3$, 138 mM NaCl, 0.338 mM Na$_2$HPO$_4$, 20 mM HEPES, pH 7.4) were prepared according to the manufacturer's instruction. Probenecid was added to the dye loading buffer to a final concentration of 2.5 mM immediately before use. Fifty microliters of the assay buffer containing ASC06-IgG1 was incubated with the 4C12 cells for 30 min at 37° C., and an equal volume of the dye loading buffer was added. Amiloride as well as PcTx1 and an isotype antibody were used as the positive and negative controls, respectively. Cells were incubated with the dye loading buffer for 1 h before reading on an FDSS/μCELL plate reader (Hamamatsu). 100 μL of the pH 6.0 activation buffer (same composition with assay buffer; pH was adjusted to 6.0) was added to the cells at a speed of 50 μL/s. The progression curve of the calcium signal produced in each well was recorded continuously for 10 s before the addition of the activation buffer (preread) and 170 s after the addition on an FDSS/μCELL (excitation wavelength: 480 nm; emission wavelength: 540 nm) FLIPR reader. To determine the IC$_{50}$ value of ASC06-IgG1 in the inhibition of ASIC1a-mediated current, a 1:3 serial dilution of ASC06-IgG1 was applied to the 4C12 cells with six repeats for each concentration.

Acidosis-Induced Cell Death. The hASIC1a-eYFP stable cells (6H7) and CHO-K1 cells were seeded in a 96-well plate at a density of 10,000 cells per well 1 d before treatment. ECF solutions at pH 5.5, 6.0, and 7.4 were used to treat the cells at 37° C. for 6 h. To test the rescuing effect of ASC06-IgG1, the antibody was dissolved in an acidic ECF (pH 5.5) to make the final antibody concentrations of 0, 50, 100, 300, 500, and 1,000 nM. The 6H7 cells were first preincubated with the antibody at the corresponding concentrations at 37° C. for 30 min in cell media. After replacing the cell media with the corresponding acidic ECFs, the cells were incubated at 37° C. for 6 h, washed with a PBS buffer (pH 7.4), and then cultured in a 1% FBS DMEM/F-12K media overnight. The supernatants of the overnight culture were collected for the LDH release measurement using a LDH Assay kit (#88953; Thermo Fisher Scientific). The cells viability was determined using the CCK-8 assay kit (#CK04; Dojindo).

The Middle Cerebral Artery Occlusion (MCAO) Model. Animal care and the experimental protocols were approved by the Animal Ethics Committee of Shanghai Jiao Tong University School of Medicine, Shanghai, China. A transient ischemic stroke in the left brain hemisphere was established in male mice (C57 BL/6, 20-25 g) using middle cerebral artery occlusion (MCAO) for 1 h before reperfusion. Three hours after ischemia, a total of 4 μL of vehicle solution (PBS) in the absence or presence of neuroprotective agents) 100 nM PcTx1 or 3.0 μg/μL endotoxin-free ASC06-IgG1 (20 M)) was administered by an intracerebroventricular (i.c.v.) injection on the contralateral side of the brain hemisphere. An irrelevant endotoxin-free antibody (3.0 μg/μL, 20 M) was used as isotype control. The cerebral blood flow was monitored by transcranial LASER Doppler to ensure that the ischemia was successfully induced. Mice were sacrificed 24 h after the i.c.v. injection. Mice brains were rapidly dissected and sectioned transversely into serial intervals slices followed by staining with a 2% vital dye 2,3,5-triphenyltetrazolium hydrochloride (TTC). The infarct area was calculated by subtracting the normal area stained with TTC in the ischemic hemisphere from that of the nonischemic hemisphere. The infarct volume was calculated by summing infarction areas of all sections and multiplying by slice thickness.

Data Analysis. The results were expressed as means±SD unless otherwise indicated. Data analysis was performed by one-way ANOVA using OriginPro 2017 statistical software. Significance was assumed at the P value <0.05.

Figure 12B:
FIG. 12B shows the results of dynamic light scattering (DLS) measurement illustrating the size of nanodiscs assembly. The inserted images show modeled particles labeled with calculated diameters.
Figure 12B:
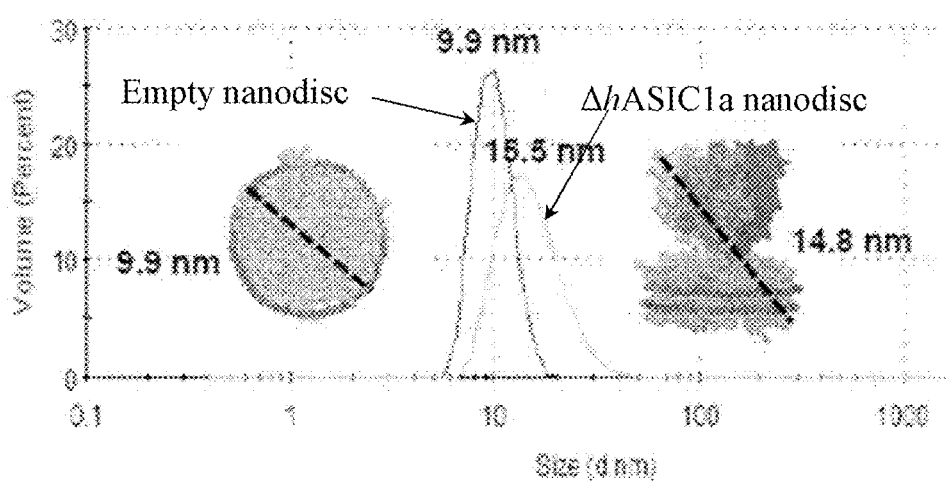
Figure 12C:
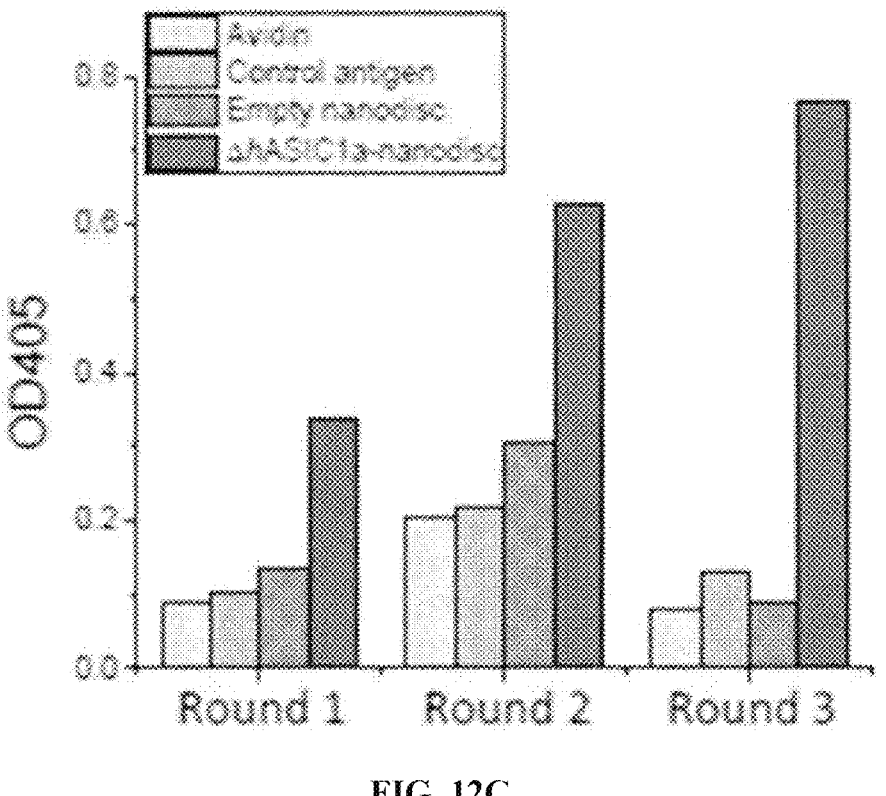
FIG. 12C shows the outputs of the positive phagemids in the "differential enrichment" panning.

Example 2: Selection of Functional Antibodies Against hASIC1a Using Nanodiscs A truncated ASIC1a (amino acids 13-464; ΔhASIC1a) was overexpressed and purified to assemble a soluble hASIC1a-displaying system. To mimic the native-like membrane environment and keep the natural extracellular conformation of hASIC1a, the truncated human ASIC1a protein was assembled it into nanodiscs, as described herein. Empty nanodiscs were prepared using identical procedure except for the addition of ΔhASIC1a. The ΔhASIC1a-loaded nano-discs (ΔhASIC1a nanodiscs) were purified using Superose 6 size exclusion chromatography (SEC). The composition of ΔhASIC1a nanodiscs was analyzed using SDS-PAGE. As shown in FIG. 12A, ΔhASIC1a protein and the MSP1 protein were present in the nanodiscs. The ΔhASIC1a pro-tein in the nanodisc was over 90% pure as judged by SDS-PAGE analysis. Densitometric analysis of the SDS/PAGE bands corresponding to membrane scaffold protein 1 (MSP1) and monomer ΔhASIC1a revealed that the molar ratio of MSP1 and ΔhASIC1a is ~2:3. The ΔhASIC1a nanodiscs and the empty nanodiscs were analyzed by to dynamic light scattering. As shown in FIG. 12B, each of the nanodiscs exhibited only one peak, indicating that the nano-discs were homogeneous. The apparent diameter of the assembled ΔhASIC1a nanodiscs was about 15.5 nm, whereas the empty nanodiscs had an apparent size of about 9.9 nm (FIG. 12B), consistent with incorporation of the ΔhASIC1a proteins in ΔhASIC1a nanodiscs (FIG. 12B). As shown in FIG. 12B, a computation model of the ΔhASIC1a nanodisc computed the distance from extra cellular domains (ECDs) to the bottom edge of the nanodisc to be ~14.8 nm, which was computed to be the largest distance.

The biotinylated nanodiscs were used in combination with streptavidin-coated magnetic beads for the panning of a human scFv combinatorial antibody library in phage con-taining $10^{11}$ members. To minimize the nonspecific interac-tions of the phagemids with the nanodisc structure, a dif-ferential enrichment strategy using empty nanodiscs was used as described herein. After three rounds of panning, six of enriched sequences were acquired, the six antibodies were purified in scFv format, and named as ASC01-ASC06.

FIGS. 19A and 19B show the nucleotide sequence and amino acid sequence of heavy chain variable region of ASC01, respectively. FIGS. 20A and 20B show the nucleo-tide sequence and amino acid sequence of light chain variable region of ASC01, respectively. The nucleotide sequence and amino acid sequence of heavy chain variable region of ASC02 is shown in FIGS. 21A and 21B, respec-tively. The nucleotide sequence and amino acid sequence of light chain variable region of ASC02 is shown in FIGS. 22A and 22B, respectively. The nucleotide sequence and amino acid sequence of heavy chain variable region of ASC03 is shown in FIGS. 23A and 23B, respectively. The nucleotide sequence and amino acid sequence of light chain variable region of ASC03 is shown in FIGS. 24A and 24B, respec-tively. The nucleotide sequence and amino acid sequence of heavy chain variable region of ASC04 is shown in FIGS. 25A and 25B, respectively. The nucleotide sequence and amino acid sequence of light chain variable region of ASC04 is shown in FIGS. 26A and 26B, respectively. The nucleo-tide sequence and amino acid sequence of heavy chain variable region of ASC05 is shown in FIGS. 27A and 27B, respectively. The nucleotide sequence and amino acid sequence of light chain variable region of ASC05 is shown in FIGS. 28A and 28B, respectively. The nucleotide sequence and amino acid sequence of heavy chain variable region of ASC06 is shown in FIGS. 29A and 29B, respec-tively. The nucleotide sequence and amino acid sequence of light chain variable region of ASC06 is shown in FIGS. 30A and 30B, respectively.

Example 3: Binding Ability to ΔhASIC1a-Nanodiscs

Figure 1:
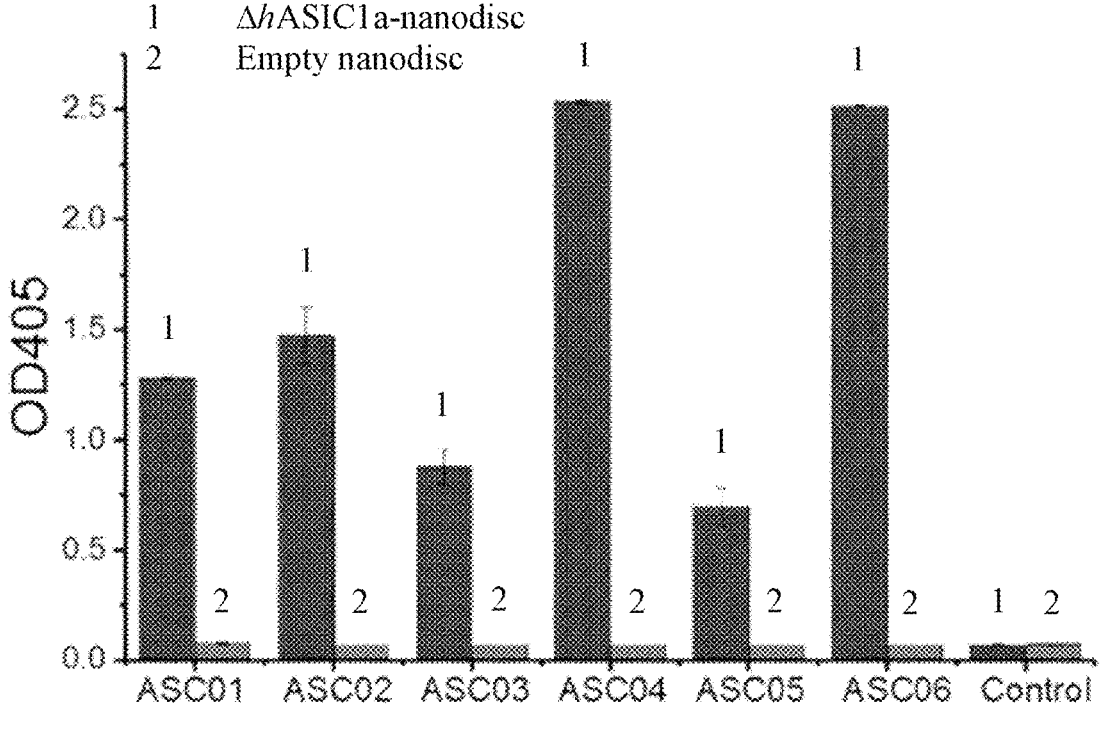
FIG. 1 shows the binding of purified scFv antibodies ASC01-ASC06 to nanodiscs containing truncated hASIC1a (amino acids 13-464; hereafter "ΔhASIC1a") as measured by ELISA. Empty nanodiscs were used as a negative control.

The binding ability of ASC01-ASC06 antibodies in scFv format to ΔhASIC1a-nanodiscs, in comparison to the empty nanodiscs, was evaluated using ELISA. As shown in FIG. 1, the ELISA signal observed with the ΔhASIC1a nanodiscs was more than the signal observed with empty nanodiscs, indicating that the enrichment of the scFv antibodies specific to the ΔhASIC1a component of the nanodiscs. Affinities of the antibodies were then measured. The table below shows binding affinities of the ASC01-ASC06 (scFv format) to ΔhASIC1a-nanodiscs as measured using the Octet system. ASC04 and ASC06 showed the strongest affinities for ΔhASIC1a nanodiscs.

| Anti-body | Conc. (nM) | Re-sponse | KD (M) | KD Error | Full X^2 | Full R^2 |
|---|---|---|---|---|---|---|
| ASC01 | 500 | 0.431 | 4.51E−08 | 4.53E−08 | 0.092567 | 0.841785 |
| ASC02 | 500 | 0.2888 | 2.62E−07 | 4.67E−07 | 0.038915 | 0.930618 |
| ASC03 | 500 | 0.2693 | 2.59E−07 | 2.13E−06 | 0.022532 | 0.966885 |
| ASC04 | 500 | 0.995 | 2.08E−08 | 9.79E−08 | 0.048226 | 0.969884 |
| ASC05 | 500 | 0.5016 | 1.37E−07 | 3.29E−08 | 0.077732 | 0.951689 |
| ASC06 | 500 | 0.5712 | 2.17E−08 | 9.66E−09 | 0.069729 | 0.873408 |

Figure 2:
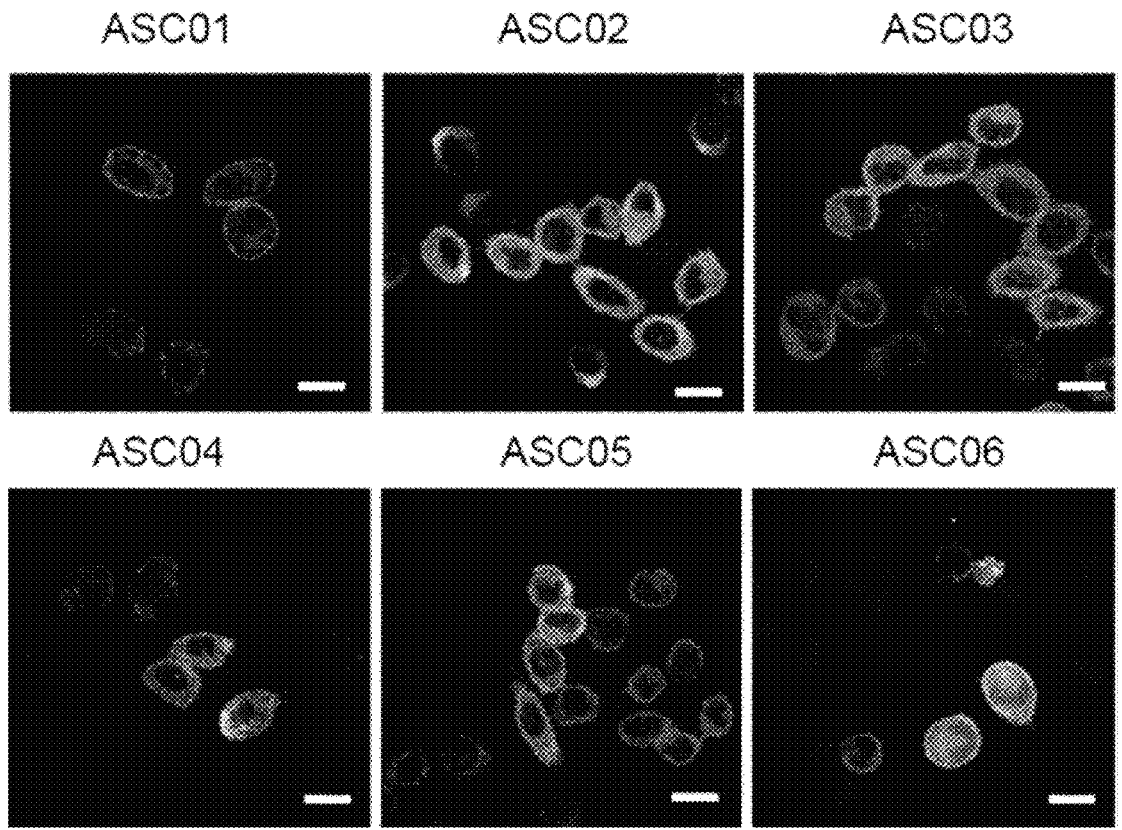
FIG. 2 shows confocal microscopy images illustrating the interactions of the six scFv antibodies with cells expressing hASIC1a on the surface. The CHO-K1 cells were transiently transfected with plasmids encoding hASIC1a-eYFP (green), and stained with ASC01-ASC06 (red), nuclei were labeled by DAPI (blue), bars=10 μm.

Example 4: Binding of ASC01-ASC06 to ASIC1a Protein Expressed on Cell Sur Face To understand whether ASC01-ASC06 specifically bind to the ASIC1a protein expressed on cell surface, the binding of the antibodies to CHO-K1/hASIC1a cells was evaluated using immunocytochemistry. The CHO-K1/hASIC1a cells overexpress the full-length hASIC1a (1-528 amino acids) protein fused with eYFP. Immunocytochemistry (ICC) stud-ies showed eYFP (green) expressed on the cell surface. As shown in FIG. 2, ASC02, ASC03, ASC04, and ASC06 (red) localized more to the plasma membranes of cells expressing hASIC1a-eYFP compared to ASC01 and ASC05. ASC06 showed more co-localization with hASIC1a-eYFP on the stained membrane, compared to the other antibodies. It is likely that ASC01-ASC05 recognize specific ASIC1a con-firmations or subpopulations.

Figure 3A:
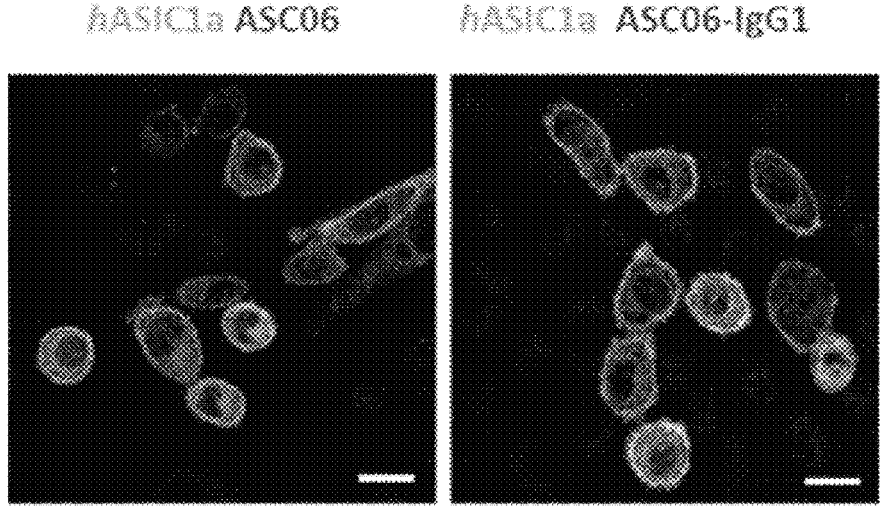
FIG. 3A shows CHO-K1/hASIC1a cells stained with ASC06 scFv and ASC06-IgG1 antibodies. The CHO-K1 cells were transiently transfected with plasmids encoding hASIC1a-eYFP (green), and stained with ASC06 scFv and ASC06-IgG1 antibodies (red), nuclei were labeled by DAPI (blue), bars=10 μm.
Figure 12D:
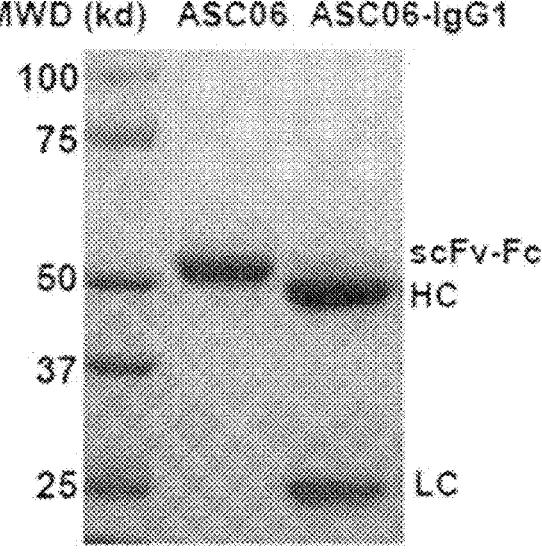
FIG. 12D shows the SDS-PAGE analysis of the purified single chain (ASC06) and full length (ASC06-IgG1) antibodies.

The ASC06 antibody was converted into a full length IgG1 form (ASC06-IgG1) for further study. The yields after purification of ASC06-IgG1 and ASC06 were similar at ~78 mg/L. As shown in FIG. 12D, SDS-PAGE analysis sug-gested that the single chain (ASC06) and full length (ASC06-IgG1) antibodies were over 90% pure, and showed protein bands at expected locations. The binding of ASC06-IgG1 to CHO-K1/hASIC1a cells was evaluated using immu-nocytochemistry, in comparison with the ASC06 (scFv for-mat) antibody. As shown in FIG. 3A, ASC06-IgG1 showed membrane co-localization with hASIC1a on the cellular surface like ASC06.

Figure 10A:
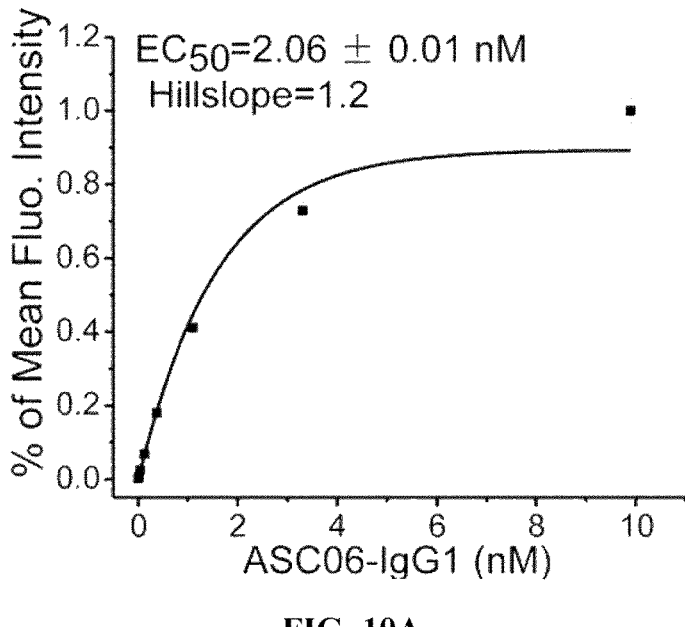
FIG. 10A shows the dose-dependent binding of ASC06-IgG1 to 6H7 cell line, which is a stable line expressing the hASIC1a-eYFP fusion protein. The data show an apparent binding affinity of 2.06±0.01 nM (n=3).
Figure 10B:
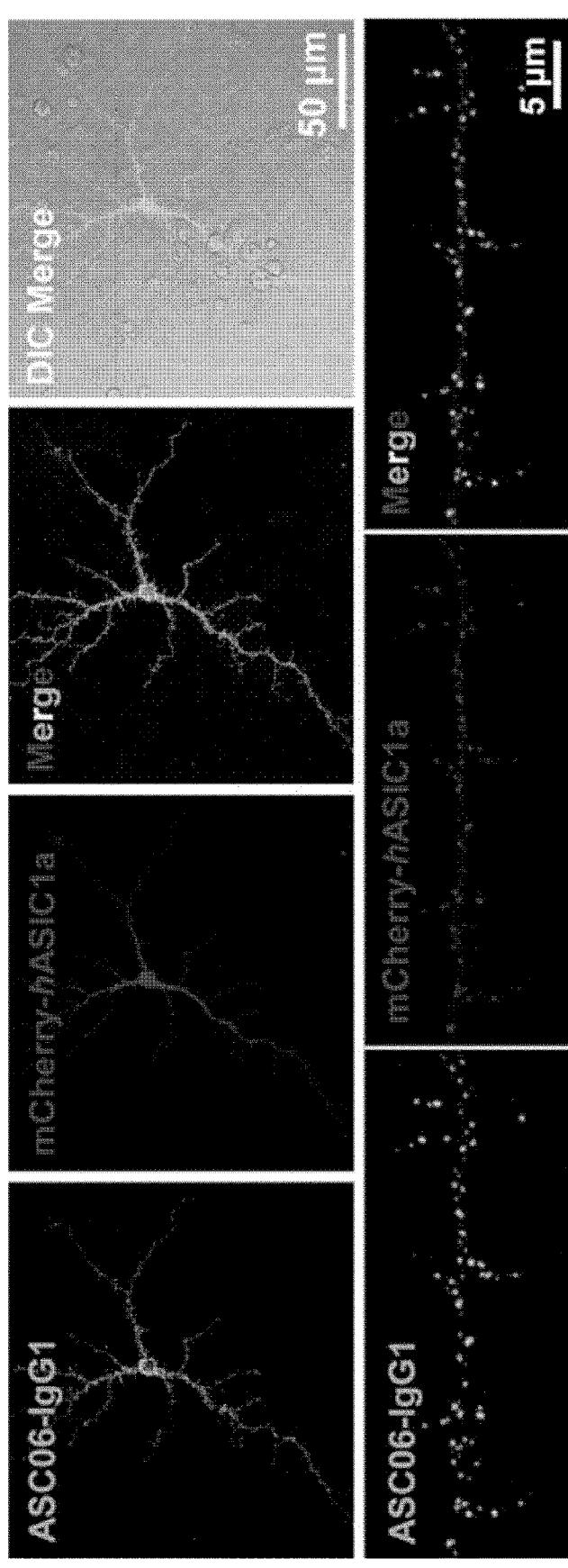
FIG. 10B (upper panels) shows confocal microscopy images of ASC06-IgG1-stained primary neurons (green) from cortex of the mASIC1a KO mice sparsely transfected with hASIC1a-mCherry (red). Differential interference contrast (DIC) view shows the bright field image merged with fluorescent view of neurons.

The binding specificity of ASC06-IgG1 was also shown using the primary cortical neurons from the ASIC1a KO mice (ASIC1a$^{-/-}$). As expected, the primary neurons from the KO mice showed no apparent binding to ASC06-IgG1 in the merged differential interference contrast (DIC) micro-scope view. As shown in FIG. 10B, when the neurons were transiently transfected with hASIC1a-mCherry, the expres-sion of hASIC1a on the membrane of the neuron was validated and visualized by ASC06-IgG1. Furthermore, the amplified view of ASC06-IgG1 signal in neuritis showed that the transiently expressed and ASC06-IgG1-labeled hASIC1a was located mainly in the postsynaptic dendrites of neurons (FIG. 10B).

Example 5: Binding Affinity of ASC06-IgG1 to Purified ΔhASIC1a Protein

Figure 3B:
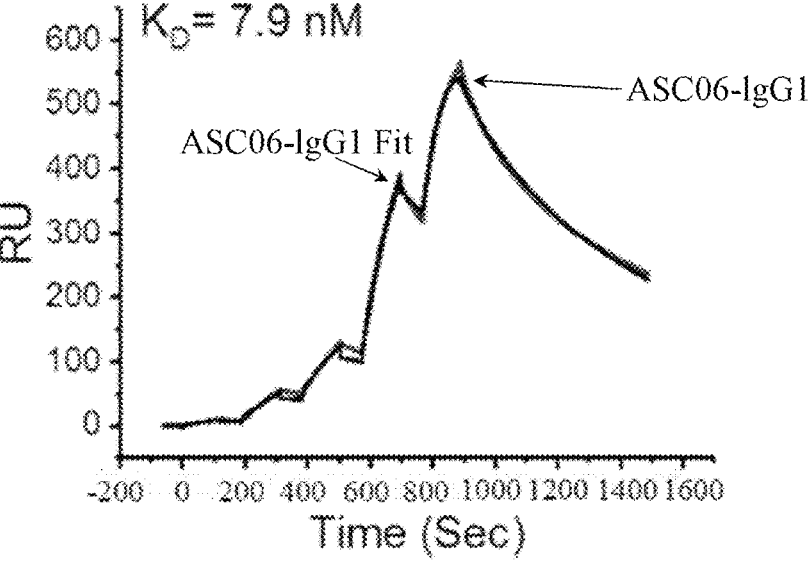
FIG. 3B shows the binding affinity of ASC06-IgG1 to ΔhASIC1a as determined using a Biacore SPR (surface plasmon resonance) system, with a single cycle kinetic (SCK) model. The line graph depicting the Resonance Units (RU, which reflects the change in analyte binding capacity of the surface) as a function of time. The binding affinity of ASC06-IgG1 to ΔhASIC1a was determined to be 7.9 nM.
Figure 15:
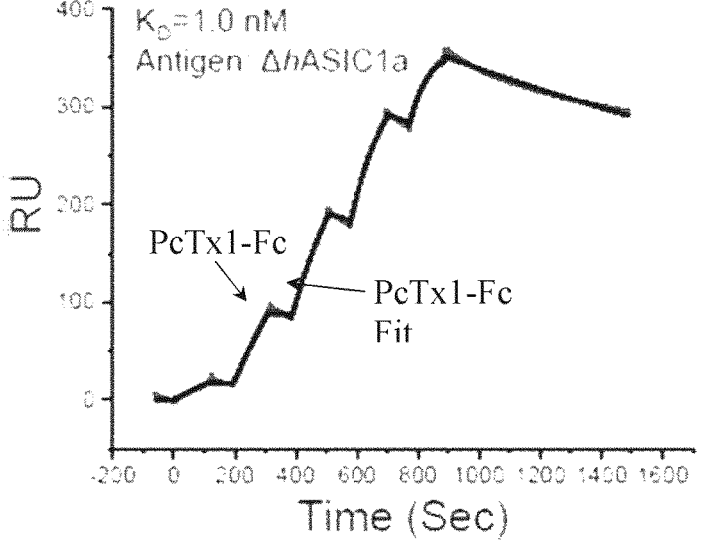
FIG. 15 shows a SPR sensorgram of PcTx1-Fc. The binding affinity of PcTx1-Fc to ΔhASIC1a was determined to be 1.0 nM, based on a single cycle kinetic method.

The binding affinity of ASC06-IgG1 to the purified ΔhASIC1a protein was measured using surface-plasmonresonance (SPR). The venom peptide PcTx1 fused with Fc (PcTx1-Fc) was used as a positive control for binding to the ΔhASIC1a protein. As shown in FIG. 15, PcTx1-Fc showed an apparent $K_d$ of 1.0 nM for binding to the ΔhASIC1a protein, consistent with reports in the literature. Hoagland et al., J Biol Chem 285:41852-41862 (2010). As shown in FIG. 3B, ASC06-IgG1 exhibited an apparent KD value of 7.9 nM for binding to the purified ΔhASIC1a protein, as measured by SPR using the Biacore T200 instrument. As a positive control, the venom peptide PcTx1 fused with Fc (PcTx1-Fc) was used.

Example 6: Binding Affinity of ASC06-IgG1 to ASIC1a Protein Expressed on Cell Surface The binding affinity of ASC06-IgG1 to the full length hASIC1a protein expressed on a cell surface was determined using quantitative fluorescence activated cell sorting (FACS). As shown in FIG. 10A, the apparent $EC_{50}$ value (concentration providing 50% of maximal binding) was determined to be 2.06±0.01 nM, which is consistent with the measured KD value (7.9 nM) against the purified ΔhASIC1a indicating that the truncated hASIC1a and cell-surface expressed full length hASIC1a share a similar extracellular conformation.

Example 7: Binding Selectivity of ASC06-IgG1

Figure 4A:
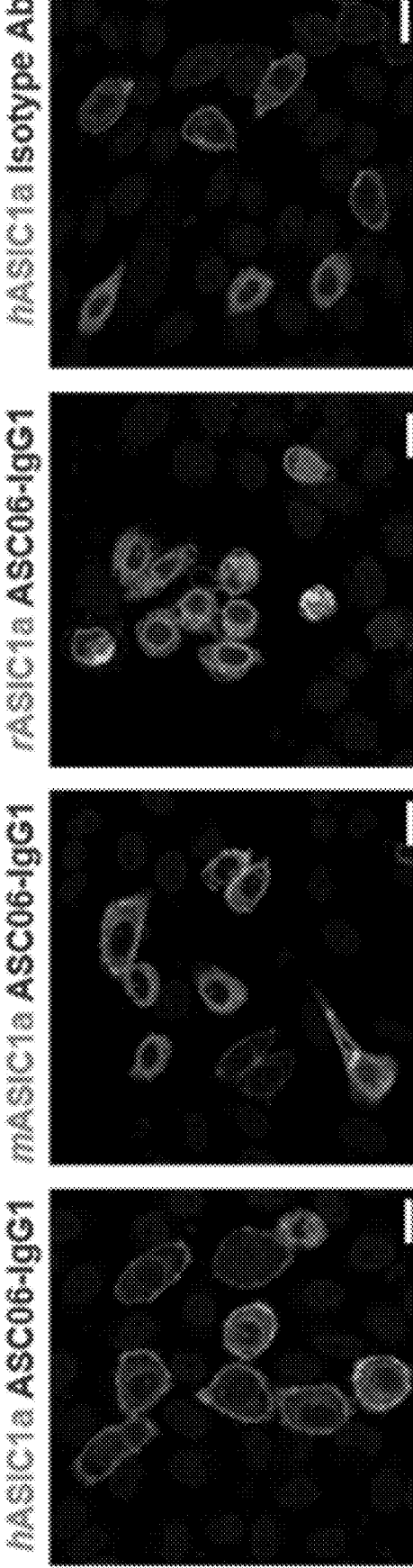
FIG. 4A shows confocal microscopy images illustrating species specificity of ASC06-IgG1. CHO-K1 cells were transiently transfected with hASIC1a-eYFP, mASIC1a-eYFP, or rASIC1a-eYFP (green) plasmids and stained with ASC06-IgG1 (red). DAPI (blue) was used to stain the nuclei of cells. Bars represent a 10 μm scale.
Figure 4B:
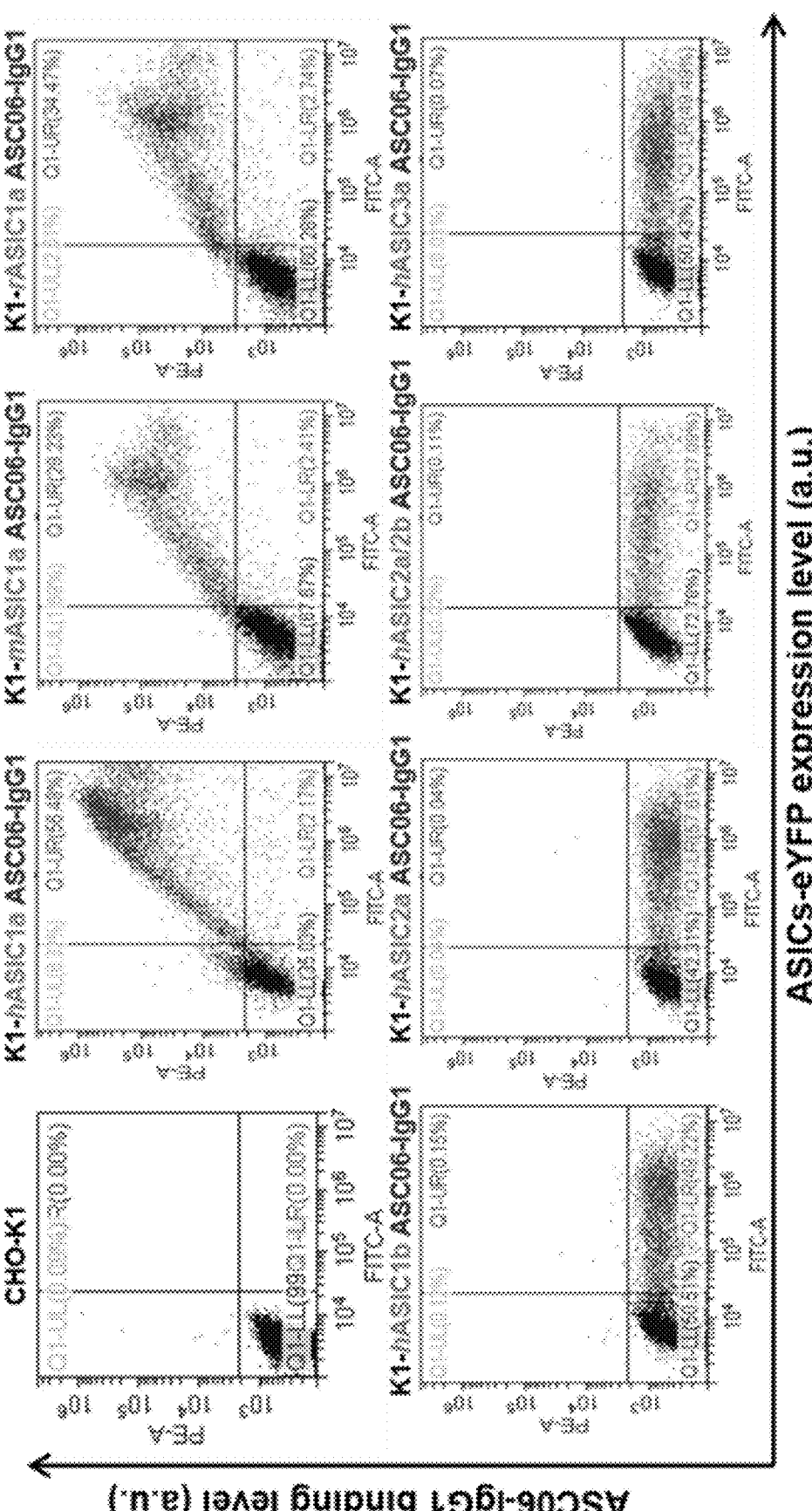
FIG. 4B illustrates species- and ASIC1 subtype-specificity of ASC06-IgG1 as determined by FACS sorting. CHO-K1 cells were transiently transfected with hASIC1a-eYFP, mASIC1a-eYFP, rASIC1a-eYFP, hASIC1b-eYFP, hASIC2a-eYFP, hASIC2a/2b-eYFP and hASIC3a-eYFP plasmids, and stained with Alexa555-conjugated ASC06-IgG1. 10,000 cells were sorted. Alexa555- and eYFP-double-positive cells, which are displayed in the upper right quadrant of the FACS profile, are indicative of binding of ASC06-IgG1 to given ASIC1 subtype or homolog.

To test the species and subtype selectivity of ASC06-IgG1, vectors encoding human ASIC1b-eYFP fusion, rat ASIC1a-eYFP fusion, mouse ASIC1a-eYFP fusion, hASIC2a-eYFP fusion, hASIC2b-eYFP fusion, and hASIC3a-eYFP fusion were constructed. The CHO-K1 cells were transiently transfected with these plasmids. FACS binding assay and immunocytochemistry (ICC) were carried out to determine if ASC06-IgG1 is able to bind to the cell surface-expressed ASIC homologs and isotypes. As shown in FIG. 4A, ICC staining showed membrane co-localization of ASC06-IgG1 with hASIC1a-eYFP, rASIC1a-eYFP, and mASIC1a-eYFP consistent with the high sequence homology between human and rodent ASIC1a. As shown in FIG. 4B, FACS results revealed that ASC06-IgG1 recognized only human/mouse/rat homologs of ASIC1a, but not other ASIC1 subtypes hASIC1b, hASIC2a, hASIC2a/2b or hASIC3a indicating a subtype selectivity of ASC06-IgG1 antibody.

Example 8: Potency of ASC06-IgG1 in Cell Culture: Patch Clamp Experiments

Figure 5A:
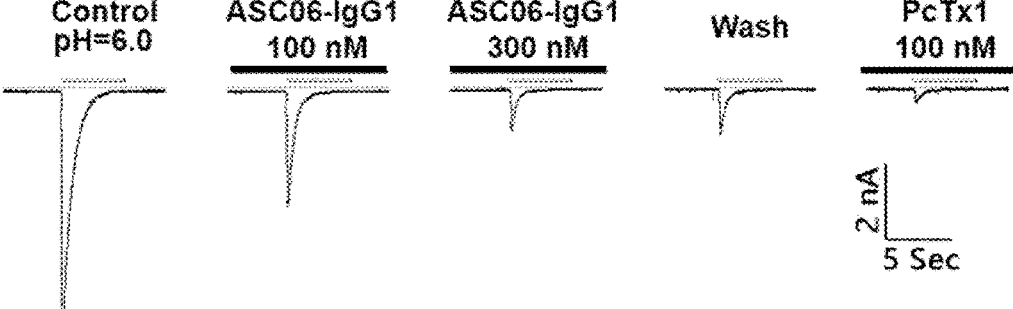
FIG. 5A shows the representative current traces from a single hASIC1a stable CHO-K1 cell in the absence or presence of different doses of ASC06-IgG1 (100 nM, 300 nM). The gray lines above the current traces show time at which the extracellular pH value was decreased from pH 7.4 to pH 6.0 and recording was conducted. The black lines above the current traces represent treatment with indicated agents. Cells treated with pH 6 were used as a negative control, and the venom peptide Psalmotoxin-1 (PcTx1) was used as a positive control. "Wash" represents the recovery of the current after the treatment of 300 nM ASC06-IgG1 followed by 15 min infusion of washing solution.
Figure 5B:
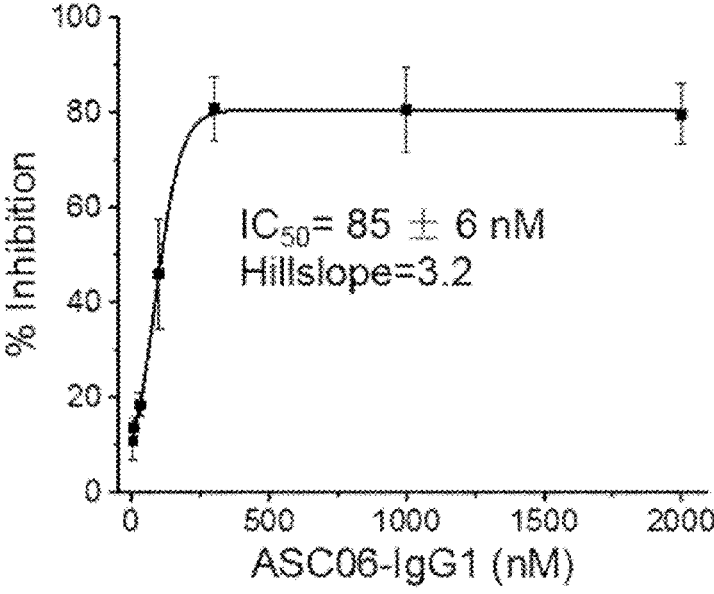
FIG. 5B shows the dose-dependent inhibition of the acid-induced hASIC1a currents by the ASC06-IgG1. The apparent $IC_{50}$ value is measured to be 85±6 nM (N=3-5). Data are shown as mean±standard deviation of five repeats.
Figure 5C:
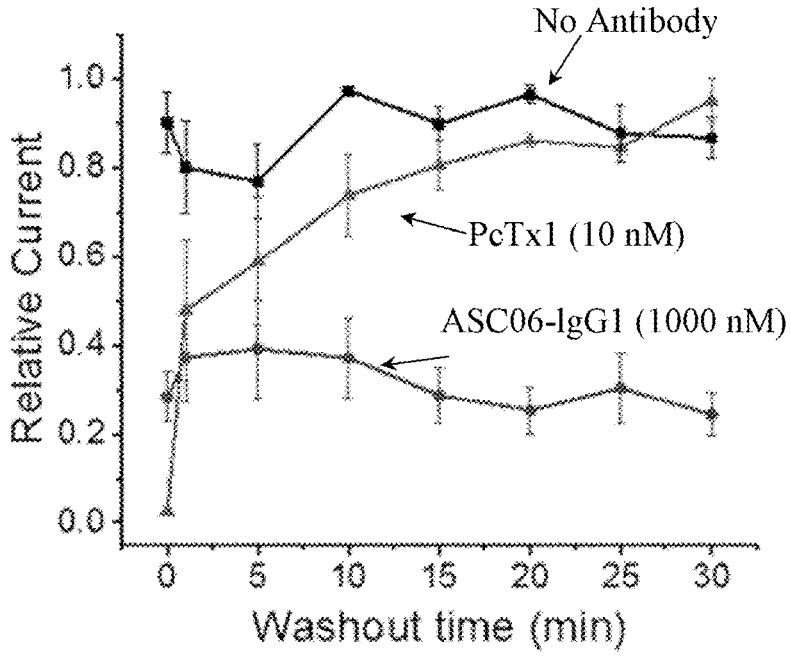
FIG. 5C shows a washout experiment illustrating the hASIC1a currents during washout time following the treatment with ASC06-IgG1 or PcTx1. The line graphs show relative currents as a function of washout time (minutes) (N=4).

The function of ASC06-IgG1 was characterized using electrophysiology approach. The effect of ASC06-IgG1 antibody on the acid-induced, hASIC1a-mediated electrical current in cells was analyzed. PcTx1 was used as a positive control. As shown in FIG. 5A, whole-cell recording mode showed that decreasing the extracellular pH value (from pH 7.4 to pH 6.0) resulted in the formation of an electric current in the hASIC1a overexpressing stable cell line. The amplitudes of the hASIC1a-mediated inward currents of the stable cells were recorded and quantitated in the absence and presence of ASC06-IgG1, with venom peptide PcTx1 (100 nM) used as positive control. As shown in FIG. 5B-5C, ASC06-IgG1 displayed a sustained (30 minutes), and dose-dependent inhibition of up to 80% of the acid (pH 6.0)-induced currents with an apparent $IC_{50}$ value of 85±6 nM. In contrast, as shown in FIGS. 5A&5C, the positive control PcTx1 showed a nearly complete inhibition of the current.

Unlike the sustained inhibition with the antibody after washing, the inhibition with PcTx1 could be readily washed out within 5 minutes (FIG. 5C).

Figures 11A, 11B:
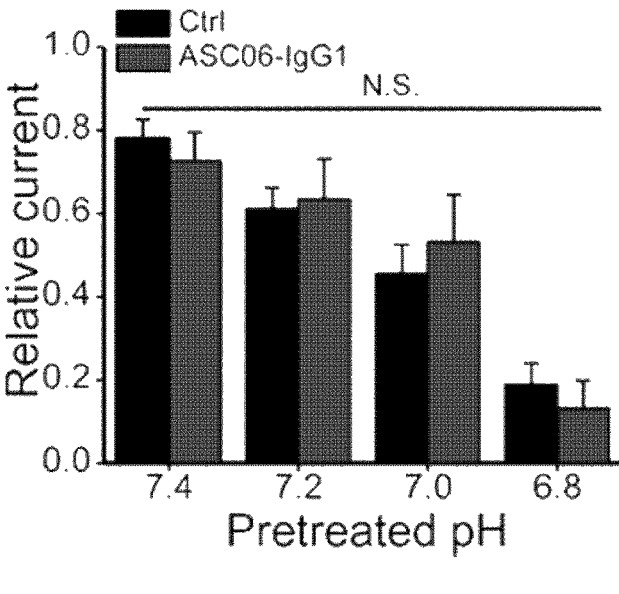
FIG. 11A shows the effect of ASC06-IgG1 on the steady-state desensitization (SSD) profile of the hASIC1a (n=6-8).
FIG. 11B shows the effect of ASC06-IgG1 on the proton activation profile of the hASIC1a (n=5).
Figure 16A:
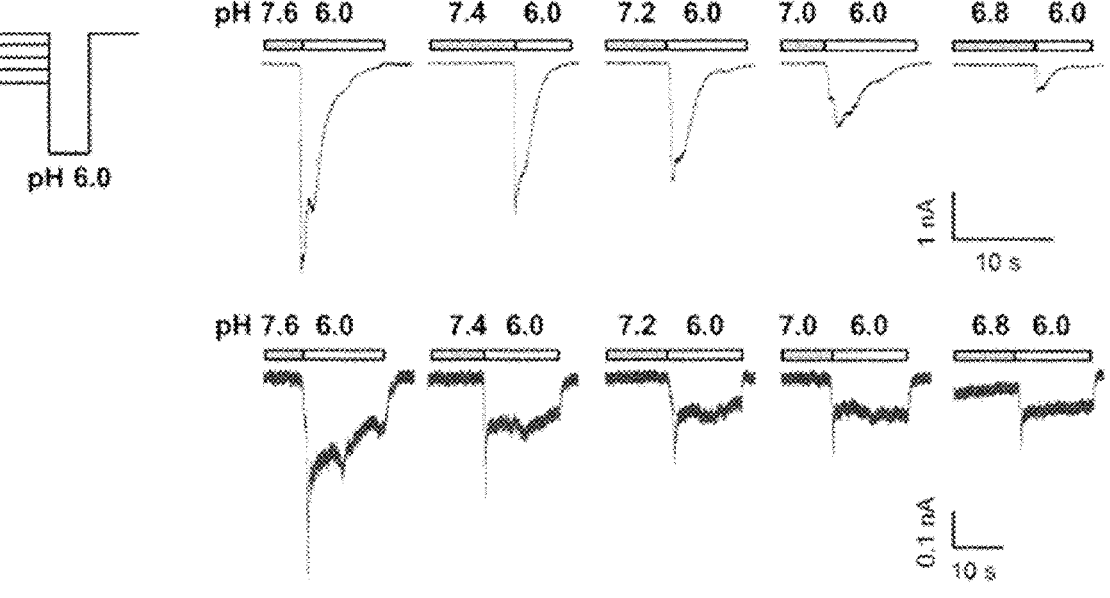
FIG. 16A shows representative traces of the ASIC1a currents evoked by pH 6.0 stimulation at various conditioning pH values. The traces in the top panel show the currents in the absence of ASC06-IgG1, and the traces in the bottom panel show currents in the presence of 300 nM ASC06-IgG1.
Figure 16B:
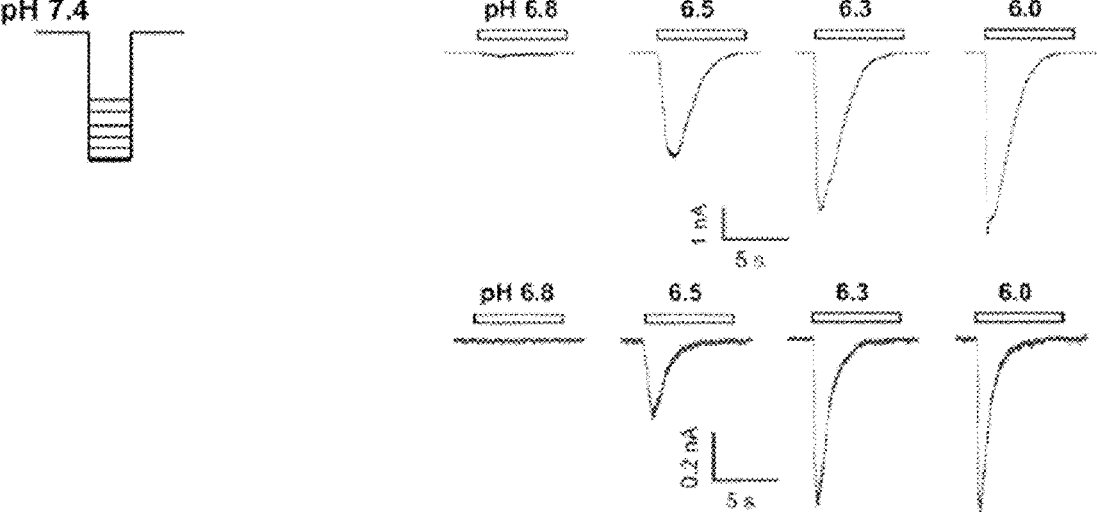
FIG. 16B shows representative current traces elicited by pH ranging from 6.8 to 6.0 with conditioning pH 7.4. Top, without ASC06-IgG1; Bottom, with ASC06-IgG1 (300 nM). Traces of pH 7.2 and pH 7.0 activation are not shown because there was no current being evoked at these conditions.

To understand the mechanism by which ASC06-IgG1 blocked the hASIC1a currents, SSD and pH activation of hASIC1a in the absence and presence of ASC06-IgG1 were examined. The $pH_{50}$ (a drop in extracellular pH, which can open 50% of the ASIC1a channel) values of the SSD curve and the pH activation curve for hASIC1a were measured and compared with or without 300 nM ASC06-IgG1. As shown in FIGS. 11A-11B, the SSD was induced when applying the conditioning extracellular fluids (ECFs) with different pH values and the activating ECF at pH 6.0, whereas the pH activation curve was constructed when applying the activating ECFs with varying pH values and the conditioning ECF at pH 7.6. No significant differences in the $pH_{50}$ values of SSD and pH activation were observed with 300 nM ASC06-IgG1. In addition, as shown in FIGS. 16A-16B, ASC06-IgG1 interfered with neither SSD nor activation of ASIC1a, as shown by the representative traces of both SSD and activation of ASIC1a currents treated with/without ASC06-IgG1. Therefore, ASC06-IgG1 seemed to block the activation of the hASIC1a using a mechanism that is noncompetitive with the proton concentration.

Figure 6A:
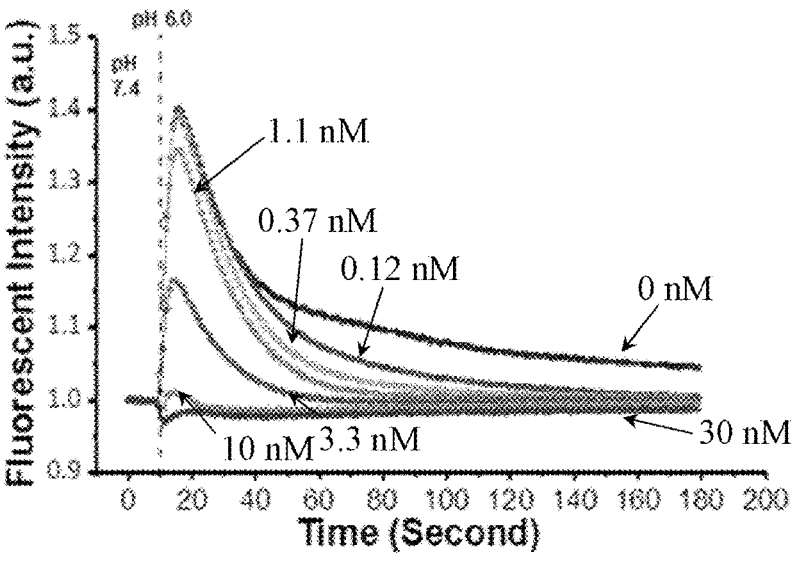
FIG. 6A shows the inhibition of acid induced ASIC1a-mediated calcium influx by ASC06-IgG1. Shown are the representative progression curves of the acid-induced calcium influx in CHO-K1 cells stably overexpressing hASIC1a-mCherry (4C12) in the presence of various concentrations of ASC06-IgG1 (from 30 to 0.12 nM in 1:3 serial dilutions).
Figure 6B:
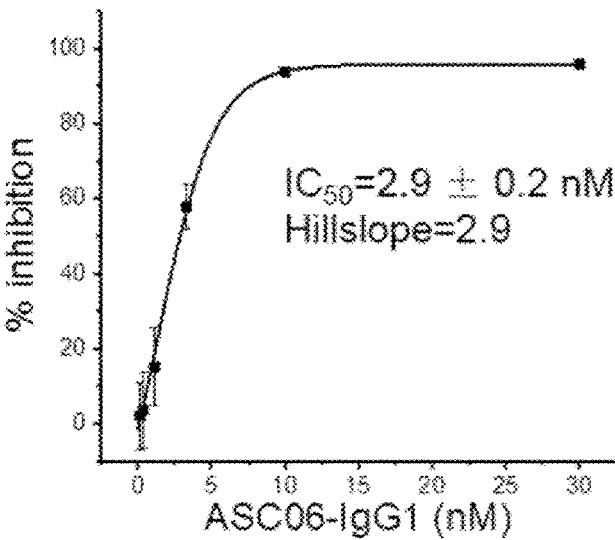
FIG. 6B shows the dose-dependent inhibition of ASC06-IgG1 to the acid induced calcium influx (N=6).

Example 9: Potency of ASC06-IgG1 in Cell Culture: FLIPR-Based Assay for the Inhibition of ASIC1a Mediated Calcium Influx by ASC06-IgG The calcium influx of the ASIC1a was measured on a FLIPR instrument using the stable cell line 4C12 expressing hASIC1a-mCherry fusion. The effect of ASC06-IgG1 antibody on the acid-induced, hASIC1a-mediated calcium influx in cells was analyzed using a FLIPR instrument by measuring the intracellular fluorescent signal of a calcium sensitive dye (Calcium 5, Molecular Devices), using the stable cell line expressing hASIC1a-mCherry fusion. In the 4C12 cells, the activation of the homomeric hASIC1a at pH 6.0 at the 10th second of recording seemed to induce a strong calcium influx, whereas the acid-induced calcium influx was not observed for the CHO-K1 cells without hASIC1a expression (FIG. 17A). As shown in FIGS. 6A and 6B, the activation of the homomeric hASIC1a channel at pH 6.0 in the stable cells at the tenth second of recording appeared to induce a strong calcium influx. The hASIC1a specific antibody, ASC06-IgG1 displayed a dose-dependent inhibition of calcium influx with an $IC_{50}$ of 2.9±0.2 nM. In contrast, as shown in FIG. 17B, the nonselective small molecule ASICs blocker, amiloride, showed only 21% inhibition at 30 M.

Example 10: pH Stability of ASC06-IgG1

The tolerance of ASC06-IgG1 to acidic conditions was tested. A concentrated ASC06-IgG1 solution (3.3 M) was incubated at different pH values (from 7.4 to 5.0) for 6 h at 37° C. and subjected to SEC-HPLC analysis. As shown in FIG. 18, no significant degradation or aggregation of ASC06-IgG1 was observed.

Example 11: ASC06-IgG1 Prevents Acidosis-Induced Cell Death In Vitro

Extracellular acidosis in stroke or ischemia-reperfusion injury is known to induce the activation of ASIC1a channels, which leads to neuronal death in the central nervous system, most likely through transient increase of intracellular calcium and related cell signaling mediated by ASIC1a. The

Figure 7A:
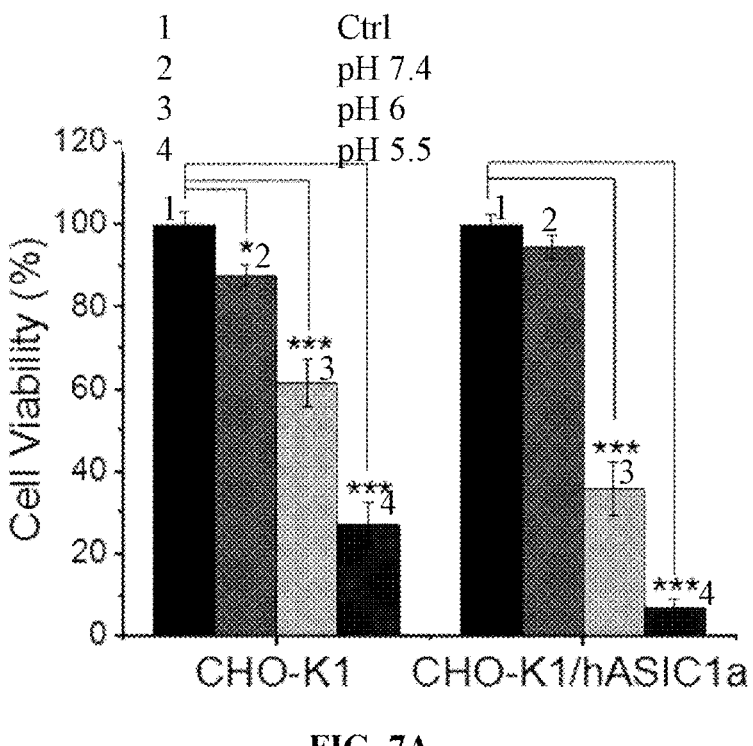
FIG. 7A shows the effect of pH (pH=5.5, 6.0, and 7.4) on the viability of CHO-K1 cells with and without the membrane expression of hASIC1a-eYFP as measured by the cytoplasmic dehydrogenase activity (N=5-6).
Figure 7B:
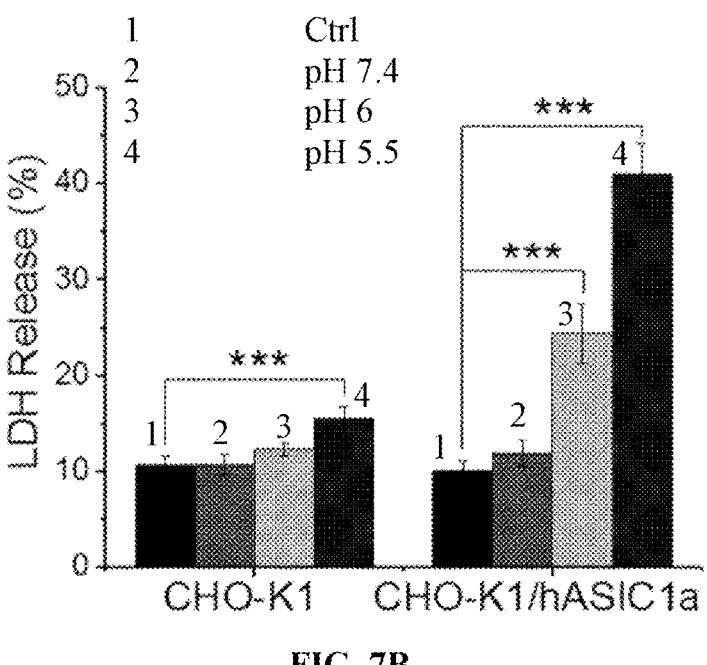
FIG. 7B shows the effect of pH (pH=5.5, 6.0, and 7.4) on the CHO-K1 cells with and without the membrane expression of hASIC1a-eYFP. Bar graphs show the released LDH contents (N=5-6).
Figure 7C:
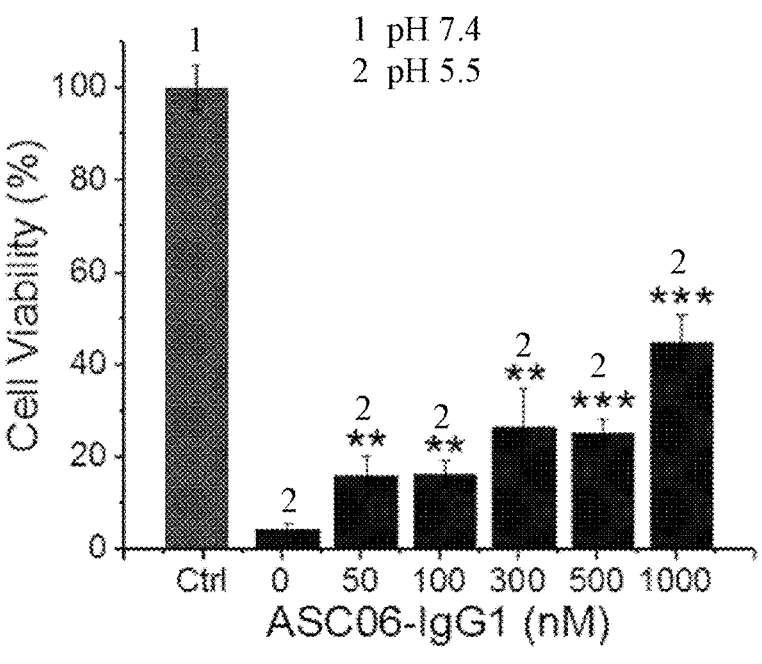
FIG. 7C shows the dose-dependent protection from acidosis-induced cell death by ASC06-IgG1 as measured by viability of the hASIC1a-eYFP stable cells in the presence of increasing concentrations of ASC06-IgG1. Data are shown as mean±standard deviation of four repeats (N=3-5).
Figure 7D:
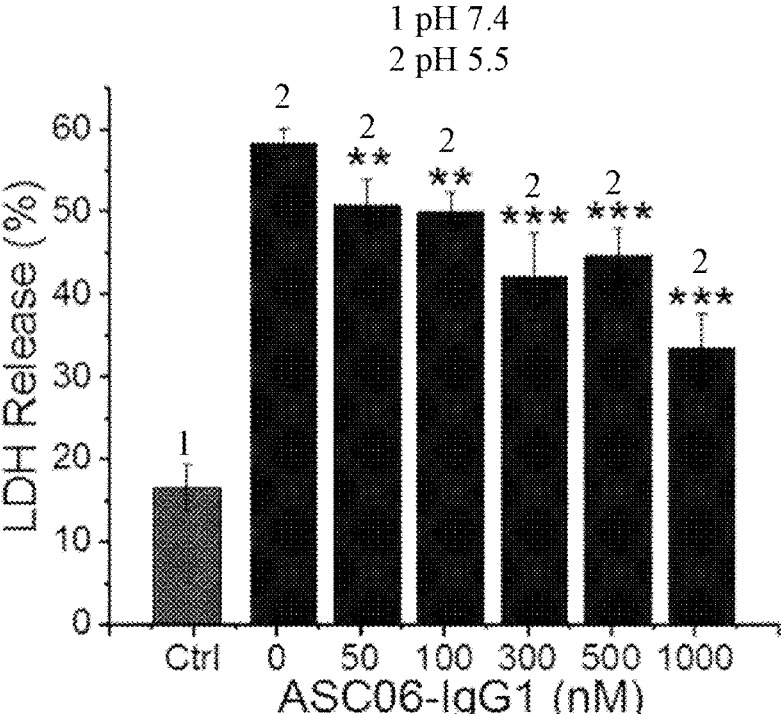
FIG. 7D shows the dose-dependent protection of acidosis-induced cell death by ASC06-IgG1 as measured by LDH release by the hASIC1a-eYFP stable cells in the presence of increasing concentrations of ASC06-IgG1. Data are shown as mean±standard deviation of three to five repeats (N=3-5).

53 survival of hASIC1a overexpressing stable cells was assessed by measuring the enzymatic activities of cytoplasmic dehydrogenases (CCK8 assay) and the concentrations of lactate dehydrogenase (LDH) secreted into the cell media, which reflect the cell viability and cytotoxicity, respectively. As shown in FIGS. 7A and 7B, the ASIC1a stable cell line (right panel) showed a higher degree of pH sensitivity than the control CHO-K1 cell especially at pH 5.5, suggesting the observed enhanced response to acid was mediated through the hASIC1a channel on the membrane. Under the same experimental conditions and at pH 5.5, ASC06-IgG1 showed a significant dose-dependent protective effect (FIGS. 7C and 7D). In the presence of 1 M ASC06-IgG1, approximately 45% of the ASIC1a expressing stable cells survived at pH 5.5 comparing to about a 5% survival rate in the absence of the antibody. Consistent with CCK8 result, the concentration of LDH released into cell media decreased after the addition of ASC06-IgG1 is also in a dose-dependent manner (FIG. 7D).

These results demonstrate that anti-ASIC1a antibodies of the present technology are useful in methods for preventing acidosis-induced cell death.

Example 12: ASC06-IgG1 Prevents Acidosis-Induced Cell Death In Vivo

Figure 8A:
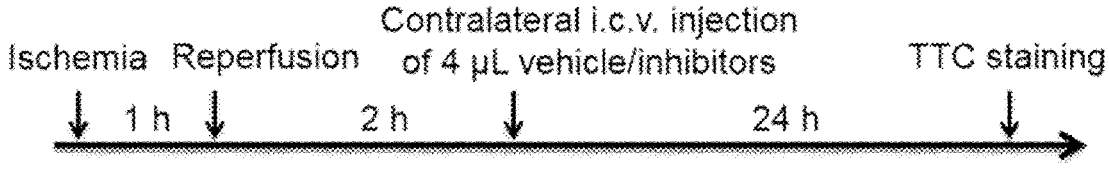
FIG. 8A shows a schematic diagram representing the experimental design for the in vivo studies in the mouse middle cerebral artery occlusion (MCAO)-induced ischemic stroke model.
Figure 8B:
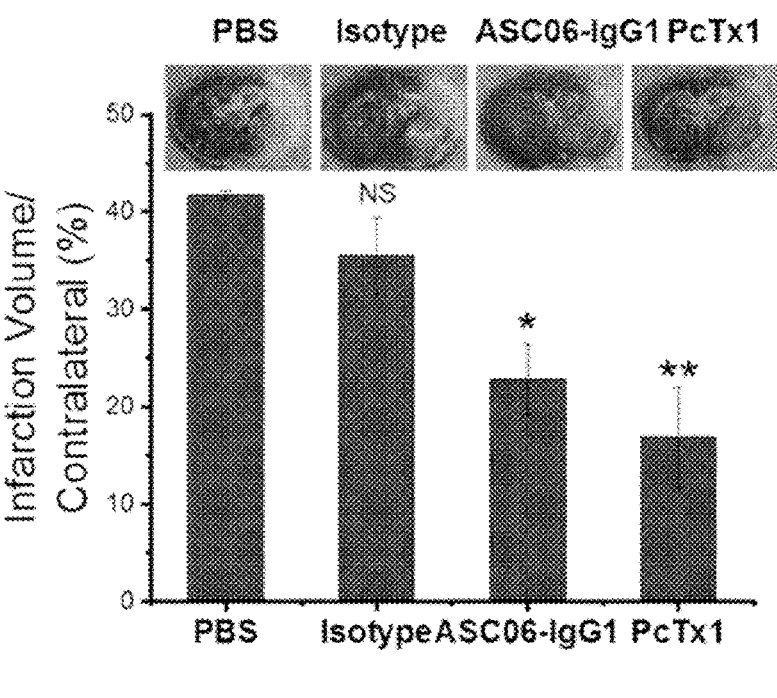
FIG. 8B (top panel) shows the images of the sections of brain illustrating the infarct area as detected by staining with the vital dye 2,3,5-triphenyltetrazolium hydrochloride (TTC) following the treatment with PBS (sham-control, N=6), Isotype control (N=6), ASC06-IgG1 (N=6) and PcTx1 (N=6) in MCAO-induced ischemic stroke model mice.

To determine if the protective effect of antibody ASC06-IgG1 in vitro could be extended to pathologies in vivo, the middle cerebral artery occlusion (MCAO) model was used to study the antibody's neuroprotective effect. Ischemia was induced by MCAO on the left brain hemisphere of the mice for 60 minutes before reperfusion. As shown in FIG. 8A, three hours after the induction of ischemia, a total of 4 μL of the vehicle solution (PBS) containing 100 nM PcTx1 or 3.0 μg/μL ASC06-IgG1 was injected intra-cerebroventricularly (i.c.v.) into the contralateral hemisphere of the mice. An irrelevant antibody (Isotype) with the same concentration as ASC06-IgG1 was administrated as a negative control. The infarct volume of the cortex and striatum were calculated 24 hours after the injection. As shown in FIG. 8B, ischemia induced a marked infarct in brain (approximately 42% volume when compared with the contralateral brain region) in the PBS group. PcTx1 decreased the infarct volume to about 17% (FIG. 8B). Isotype antibody did not show any protection effect. On the other hand, like PcTx1, the group treated with ASC06-IgG1 showed a significantly reduced infarct volume (decrease to about 23%), indicating a potent neuroprotection effect of the antibody against stroke (FIG. 8B).

These results demonstrate that anti-ASIC1a antibodies of the present technology are useful in methods for preventing acidosis-induced cell death and for treating ischemic stroke.

Example 13: ASC06-IgG1 Bound to a Conformational Epitope of hASIC1a

Figure 13A:
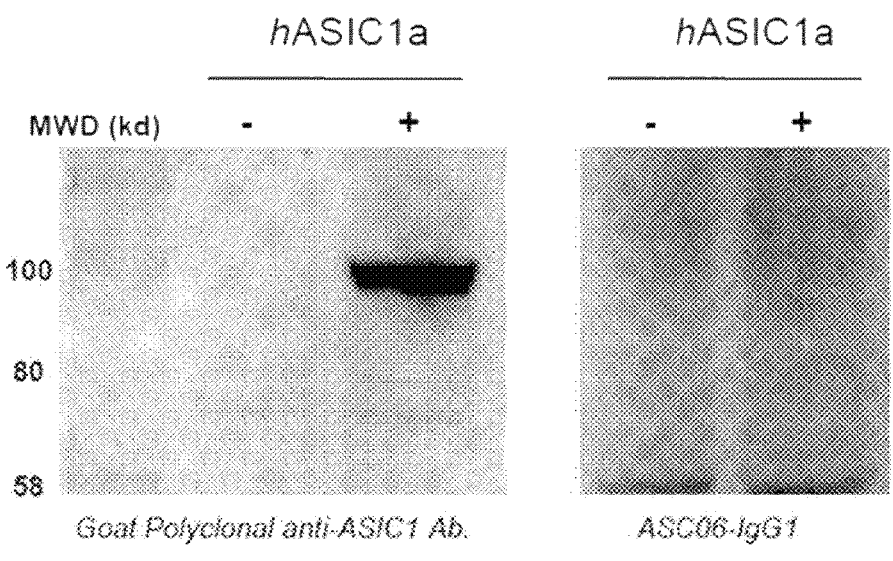
FIG. 13A shows the Western-blot analysis of the cell lysates from CHO-K1 cells ("-"), or the CHO-K1 stable cell line expressing hASIC1a-eYFP ("+") using a commercial goat polyconal anti-ASIC1a antibody or ASC06-IgG1.

As demonstrated herein, the antibody ASC06-IgG1 was shown to be able to recognize and bind to purified ASIC1a protein and ASIC1a protein expressed on the cell surface. To characterize the interaction between ASC06-IgG1 and hASIC1a, the 6H7 stable line expressing the hASIC1a-eYFP fusion protein was used in a Western blot analysis. As shown in FIG. 13A, ASC06-IgG1 could not recognize the hASIC1a in cell lysate of cells overexpressing ASIC1a in Western blot assays. In contrast, both the commercial goat polyclonal anti-ASIC1 antibody and the anti-eYFP antibody were able to detect the hASIC1a-eYFP protein in the 6H7 lysate at molecular mass around 100 kDa (FIG. 13A and data not shown). This observation indicated that the antibody recognized ASIC1a in a conformation-dependent manner.

Figure 13B:
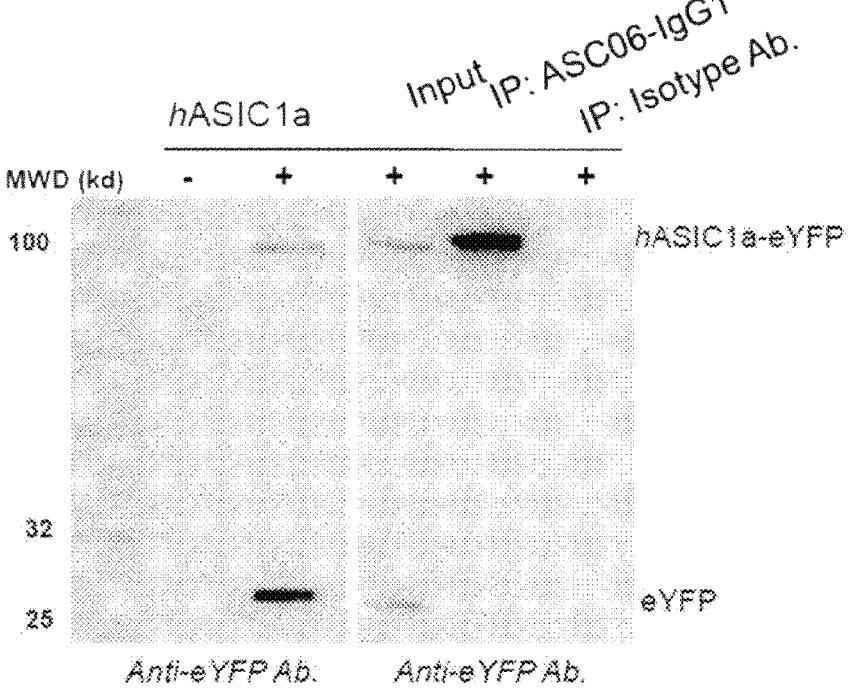
FIG. 13B shows Western-blots of the cell lysates of CHO-K1 cells ("-"), or the CHO-K1 stable cell line expressing hASIC1a-eYFP ("+") that were immunoprecipitated with ASC06-IgG1 and analyzed by a commercial anti-eYFP antibody.

ASC06-IgG1 was used to pull down native hASIC1a-YFP in cell lysate followed by anti-eYFP Western blot for hASIC1a-YFP detection. As shown in FIG. 13B, a clear band of ~100 kDa representing the hASIC1a-eYFP was observed, indicating that ASC06-IgG1 recognized hASIC1a in a conformation-dependent manner.

To understand the nature of binding of ASC06 to hASIC1a, a complex was formed by mixing hASIC1a-ECD and ASC06-Fab. The complex, hASIC1a-ECD and ASC06-Fab were resolved using gel filtration. As shown in FIG. 14, hASIC1a-ECD existed as homotrimer in solution and formed a stable complexes with three ASC06-Fabs.

To further understand the nature of the antibody binding, negative staining EM studies was carried out with the complex of ectodomain of hASIC1a (hASIC1a-ECD) and ASC06 in Fab format (ASC06-Fab). As shown in FIG. 9A, the unprocessed negative staining EM image revealed that most of the particles showed a triangular arrangement for the formed complex; meanwhile, particles of boomerang shape and other shapes were also observed, which likely represent complexes with one or two ASC06-Fabs missing. As shown in FIG. 9A, the EM result showed that each ASC06-Fab bound to in the hASIC1a-ECD-ASC06-Fab complex. As shown in FIG. 9D, several amino acids of ASIC1a were predicted to be important for the binding of ASC06-IgG1 to hASIC1a based on the molecular dynamic simulation model. As shown in FIG. 9C, the 2D averages analyses results, triangular-shaped complexes with clear domain divisions were shown, showing the interactions of ASC06-Fab onto a trimer configuration of hASIC1a-ECD. Combining molecular docking and molecular dynamics simulation, a model that coarsely reproduces the apparent experimental geometry was obtained (FIG. 9D). As shown in FIGS. 9A-9C, the epitope was located on a surface formed by two hASIC1a-ECD subunits.

To confirm the role of these amino acids, alanine mutagenesis was performed and four amino acids are very important for antibody binding were identified. Plasmid encoding single amino acid mutation of hASIC1a-eYFP was constructed and transient transfected into CHO-K1 cells. FACS binding assay was then performed to test whether the ASC06-IgG1 still binds to cell surface expressing mutated hASIC1a. As shown in FIG. 9E, unlike WT hASIC1a, which can bind to ASC06-IgG1, either hASIC1a Y360A mutation or hASIC1a N322A mutation decrease the ASC06-IgG1's binding ability; hASIC1a Y318A mutation abolished the ASC06-IgG1's binding, so does hASIC1a F252A mutation.

EQUIVALENTS

The present technology is not to be limited in terms of the particular embodiments described in this application, which are intended as single illustrations of individual aspects of the present technology. Many modifications and variations of this present technology can be made without departing from its spirit and scope, as were apparent to those skilled in the art. Functionally equivalent methods and apparatuses within the scope of the present technology, in addition to those enumerated herein, were apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As were understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as were understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

---

What is claimed is:

1. A method for treating ischemic stroke in a subject in need thereof, comprising administering to the subject a therapeutically effective amount of an antibody or antigen binding fragment thereof comprising a heavy chain immunoglobulin variable domain (VH) and a light chain immunoglobulin variable domain (VL), (a) wherein the $V_H$ comprises a $V_H$-CDR1 sequence of SEQ ID NO: 3, a VH-CDR2 sequence of SEQ ID NO: 4, and a VH-CDR3 sequence of SEQ ID NO: 5 and the VL comprises a VL-CDR1 sequence of SEQ ID NO: 8, a VL-CDR2 sequence of SEQ ID NO: 9, and a VH-CDR3 sequence of SEQ ID NO: 10; or (b) wherein the VH comprises a VH-CDR1 sequence of SEQ ID NO: 13, a VH-CDR2 sequence of SEQ ID NO: 14, and a VH-CDR3 sequence of SEQ ID NO: 15 and the VL comprises a VL-CDR1 sequence of SEQ ID NO: 18, a VL-CDR2 sequence of SEQ ID NO: 19, and a VH-CDR3 sequence of SEQ ID NO: 20; or (c) wherein the VH comprises a VH-CDR1 sequence of SEQ ID NO: 23, a VH-CDR2 sequence of SEQ ID NO: 24, and a VH-CDR3 sequence of SEQ ID NO: 25 and the VL comprises a VL-CDR1 sequence of SEQ ID NO: 28, a VL-CDR2 sequence of SEQ ID NO: 29, and a VH-CDR3 sequence of SEQ ID NO: 30; or (d) wherein the VH comprises a VH-CDR1 sequence of SEQ ID NO: 33, a VH-CDR2 sequence of SEQ ID NO: 34, and a VH-CDR3 sequence of SEQ ID NO: 35 and the VL comprises a VL-CDR1 sequence of SEQ ID NO: 38, a VL-CDR2 sequence of SEQ ID NO: 39, and a VH-CDR3 sequence of SEQ ID NO: 40; or (e) wherein the VH comprises a VH-CDR1 sequence of SEQ ID NO: 43, a VH-CDR2 sequence of SEQ ID NO: 44, and a VH-CDR3 sequence of SEQ ID NO: 45 and the VL comprises a VL-CDR1 sequence of SEQ ID NO: 48, a VL-CDR2 sequence of SEQ ID NO: 49, and a VH-CDR3 sequence of SEQ ID NO: 50, wherein the antibody or antigen binding fragment thereof binds to the ASIC1a protein.

2. The method of claim 1, (a) wherein the antibody or antigen binding fragment thereof further comprises a Fc domain of an isotype selected from the group consisting of IgG1, IgG2, IgG3, IgG4, IgA1, IgA2, IgM, IgD, and IgE; or (b) wherein the antibody or antigen binding fragment thereof is selected from the group consisting of Fab, F(ab')$_2$, Fab', scF$_v$, and F$_v$; or (c) wherein the antibody or antigen binding fragment thereof is a monoclonal antibody, a chimeric antibody, a humanized antibody, or a bispecific antibody.

3. The method of claim 1, wherein the antibody or antigen binding fragment thereof (a) binds an extracellular domain of ASIC1a;

(b) binds an epitope that spans two ASIC1a subunits; and/or (c) inhibits proton-induced ASIC1a currents.

4. The method of claim 1, wherein the V$_H$ comprises an amino acid sequence selected from the group consisting of SEQ ID NOs: 2, 12, 22, 32, and 42, and/or the V$_L$ comprises an amino acid sequence selected from the group consisting of SEQ ID NOs: 7, 17, 27, 37, and 47.

5. The method of claim 1, wherein the antibody or antigen binding fragment thereof comprises a HC amino acid sequence and a LC amino acid sequence that comprises the amino acid sequences selected from the group consisting of:

SEQ ID NO: 2 and SEQ ID NO: 7 (ASC01);

SEQ ID NO: 12 and SEQ ID NO: 17 (ASC02);

SEQ ID NO: 22 and SEQ ID NO: 27 (ASC03);

SEQ ID NO: 32 and SEQ ID NO: 37 (ASC04); and

SEQ ID NO: 42 and SEQ ID NO: 47 (ASC05), respectively.

6. A method for alleviating one or more symptoms of ischemic stroke in a subject in need thereof, the method comprising: administering to the subject a therapeutically effective amount of an antibody or antigen binding fragment thereof comprising a heavy chain immunoglobulin variable domain (V$_H$) and a light chain immunoglobulin variable domain (V$_L$), (a) wherein the V$_H$ comprises a V$_H$-CDR1 sequence of SEQ ID NO: 3, a VH-CDR2 sequence of SEQ ID NO: 4, and a VH-CDR3 sequence of SEQ ID NO: 5 and the VL comprises a VL-CDR1 sequence of SEQ ID NO: 8, a VL-CDR2 sequence of SEQ ID NO: 9, and a VH-CDR3 sequence of SEQ ID NO: 10; or (b) wherein the VH comprises a VH-CDR1 sequence of SEQ ID NO: 13, a VH-CDR2 sequence of SEQ ID NO: 14, and a VH-CDR3 sequence of SEQ ID NO: 15 and the VL comprises a VL-CDR1 sequence of SEQ ID NO: 18, a VL-CDR2 sequence of SEQ ID NO: 19, and a VH-CDR3 sequence of SEQ ID NO: 20; or (c) wherein the VH comprises a VH-CDR1 sequence of SEQ ID NO: 23, a VH-CDR2 sequence of SEQ ID NO: 24, and a VH-CDR3 sequence of SEQ ID NO: 25 and the VL comprises a VL-CDR1 sequence of SEQ ID NO: 28, a VL-CDR2 sequence of SEQ ID NO: 29, and a VH-CDR3 sequence of SEQ ID NO: 30; or (d) wherein the VH comprises a VH-CDR1 sequence of SEQ ID NO: 33, a VH-CDR2 sequence of SEQ ID NO: 34, and a VH-CDR3 sequence of SEQ ID NO: 35 and the VL comprises a VL-CDR1 sequence of SEQ ID NO: 38, a VL-CDR2 sequence of SEQ ID NO: 39, and a VH-CDR3 sequence of SEQ ID NO: 40; or (e) wherein the VH comprises a VH-CDR1 sequence of SEQ ID NO: 43, a VH-CDR2 sequence of SEQ ID NO: 44, and a VH-CDR3 sequence of SEQ ID NO: 45 and the VL comprises a VL-CDR1 sequence of SEQ ID NO: 48, a VL-CDR2 sequence of SEQ ID NO: 49, and a VH-CDR3 sequence of SEQ ID NO: 50, wherein the antibody or antigen binding fragment thereof binds to the ASIC1a protein.

7. The method of claim 6, wherein the antibody or antigen binding fragment thereof comprises a HC amino acid sequence and a LC amino acid sequence that comprises the amino acid sequences selected from the group consisting of:

SEQ ID NO: 2 and SEQ ID NO: 7 (ASC01);

SEQ ID NO: 12 and SEQ ID NO: 17 (ASC02);

SEQ ID NO: 22 and SEQ ID NO: 27 (ASC03);

SEQ ID NO: 32 and SEQ ID NO: 37 (ASC04); and

SEQ ID NO: 42 and SEQ ID NO: 47 (ASC05), respectively.

8. The method of claim 6, (a) wherein the antibody or antigen binding fragment thereof further comprises a Fc domain of an isotype selected from the group consisting of IgG1, IgG2, IgG3, IgG4, IgA1, IgA2, IgM, IgD, and IgE; or (b) wherein the antibody or antigen binding fragment thereof is selected from the group consisting of Fab, F(ab')$_2$, Fab', scF$_v$, and F$_v$; or (c) wherein the antibody or antigen binding fragment thereof is a monoclonal antibody, a chimeric antibody, a humanized antibody, or a bispecific antibody.

9. The method of claim 6, wherein the antibody or antigen binding fragment thereof (a) binds an extracellular domain of ASIC1a;

(b) binds an epitope that spans two ASIC1a subunits; and/or (c) inhibits proton-induced ASIC1a currents.

10. The method of claim 6, wherein the one or more symptoms of ischemic stroke is sudden weakness, paralysis or numbness of the face, arms, or legs, drooping of one side of the face, confusion, difficulty with speaking, difficulty with understanding speech, trouble seeing in one or both eyes, blurred vision, blackened vision, double vision, difficulty with breathing, dizziness, difficulty with walking, loss of balance, loss of coordination, unexplained falls, loss of consciousness, sudden headache or severe headache.

11. The method of claim 6, wherein the one or more symptoms of ischemic stroke is sudden-onset face weakness, drooping of one side of the face, arm drift or abnormal speech.

12. An antibody or antigen binding fragment thereof comprising a heavy chain immunoglobulin variable domain (V$_H$) and a light chain immunoglobulin variable domain (V$_L$), (a) wherein the V$_H$ comprises a V$_H$-CDR1 sequence of SEQ ID NO: 3, a VH-CDR2 sequence of SEQ ID NO: 4, and a VH-CDR3 sequence of SEQ ID NO: 5 and the VL comprises a VL-CDR1 sequence of SEQ ID NO: 8, a VL-CDR2 sequence of SEQ ID NO: 9, and a VH-CDR3 sequence of SEQ ID NO: 10; or (b) wherein the VH comprises a VH-CDR1 sequence of SEQ ID NO: 13, a VH-CDR2 sequence of SEQ ID NO: 14, and a VH-CDR3 sequence of SEQ ID NO: 15 and the VL comprises a VL-CDR1 sequence of SEQ ID NO: 18, a VL-CDR2 sequence of SEQ ID NO: 19, and a VH-CDR3 sequence of SEQ ID NO: 20; or

(c) wherein the VH comprises a VH-CDR1 sequence of SEQ ID NO: 23, a VH-CDR2 sequence of SEQ ID NO: 24, and a VH-CDR3 sequence of SEQ ID NO: 25 and the VL comprises a VL-CDR1 sequence of SEQ ID NO: 28, a VL-CDR2 sequence of SEQ ID NO: 29, and a VH-CDR3 sequence of SEQ ID NO: 30; or (d) wherein the VH comprises a VH-CDR1 sequence of SEQ ID NO: 33, a VH-CDR2 sequence of SEQ ID NO: 34, and a VH-CDR3 sequence of SEQ ID NO: 35 and the VL comprises a VL-CDR1 sequence of SEQ ID NO: 38, a VL-CDR2 sequence of SEQ ID NO: 39, and a VH-CDR3 sequence of SEQ ID NO: 40; or (e) wherein the VH comprises a VH-CDR1 sequence of SEQ ID NO: 43, a VH-CDR2 sequence of SEQ ID NO: 44, and a VH-CDR3 sequence of SEQ ID NO: 45 and the VL comprises a VL-CDR1 sequence of SEQ ID NO: 48, a VL-CDR2 sequence of SEQ ID NO: 49, and a VH-CDR3 sequence of SEQ ID NO: 50, wherein the antibody or antigen binding fragment thereof binds to the ASIC1a protein.

13. The antibody, or antigen binding fragment thereof of claim 12, (a) wherein the antibody or antigen binding fragment thereof further comprises a Fc domain of an isotype selected from the group consisting of IgG1, IgG2, IgG3, IgG4, IgA1, IgA2, IgM, IgD, and IgE; or (b) wherein the antigen binding fragment is selected from the group consisting of Fab, F(ab')$_2$, Fab', scF$_v$, and F$_v$; or

(c) wherein antibody, or antigen binding fragment thereof is a monoclonal antibody, a chimeric antibody, a humanized antibody, or a bispecific antibody.

14. The antibody, or antigen binding fragment thereof of claim 12, wherein the antibody, or antigen binding fragment thereof (a) binds an extracellular domain of ASIC1a;

(b) binds an epitope that spans two ASIC1a subunits; and/or (c) inhibits ASIC1a currents.

15. A nucleic acid sequence encoding the antibody or antigen binding fragment of claim 12, wherein the nucleic acid sequence is selected from the group consisting of SEQ ID NOs: 1, 6, 11, 16, 21, 26, 31, 36, 41, and 46.

16. A host cell comprising a vector, wherein the vector comprises the nucleic acid of claim 15.

17. A kit comprising the antibody, or antigen binding fragment thereof of claim 12 and instructions for use.

18. The kit of claim 17, wherein the antibody, or antigen binding fragment is coupled to at least one detectable label selected from the group consisting of a radioactive label, a fluorescent label, and a chromogenic label.

19. The kit of claim 17, further comprising a secondary antibody that specifically binds to the antibody, or antigen binding fragment.

20. A method for detecting ASIC1a protein in a biological sample comprising contacting the biological sample with the antibody, or antigen binding fragment thereof of claim 12 conjugated to a detectable label; and detecting the presence and the level of the detectable label in the biological sample.

* * * * *

SEQUENCE LISTING

```
<160> NUMBER OF SEQ ID NOS: 60

<210> SEQ ID NO 1
<211> LENGTH: 357
<212> TYPE: DNA
<213> ORGANISM: Artificial Sequence
<220> FEATURE:
<223> OTHER INFORMATION: Nucleotide sequence of ASC01 VH

<400> SEQUENCE: 1
caggtgcagc tggtggagac tggcccccga ctggtgaagc cttcacagac cctgtccctc      60
acctgcactg tctccggtgg ctccatcaat agtggcggtt actactgggg ctggatccgc     120
cagcattccg ggaagggcct ggagtggatt ggctacatct atcccagggg gagcagctac     180
tacaacccgt ccctcaggag tcgagttacc atatcagcag acacgtctag gaataacttc     240
tccctgaagt tgacctctgt gactgccgcg gacacggccg tgtattactg tgcgagagtc     300
ggttatacgg gtgcttttga tatctggggc caaggcaccc tggtcaccgt ctcctca        357

<210> SEQ ID NO 2
<211> LENGTH: 119
<212> TYPE: PRT
<213> ORGANISM: Artificial Sequence
<220> FEATURE:
<223> OTHER INFORMATION: Amino acid sequence of ASC01 VH

<400> SEQUENCE: 2

Gln Val Gln Leu Val Glu Thr Gly Pro Arg Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Gly Trp Ile Arg Gln His Ser Gly Lys Gly Leu Glu
        35                  40                  45

Trp Ile Gly Tyr Ile Tyr Pro Arg Gly Ser Ser Tyr Tyr Asn Pro Ser
    50                  55                  60

Leu Arg Ser Arg Val Thr Ile Ser Ala Asp Thr Ser Arg Asn Asn Phe
65                  70                  75                  80

Ser Leu Lys Leu Thr Ser Val Thr Ala Ala Asp Thr Ala Val Tyr Tyr
                85                  90                  95

Cys Ala Arg Val Gly Tyr Thr Gly Ala Phe Asp Ile Trp Gly Gln Gly
            100                 105                 110
```

```
Thr Leu Val Thr Val Ser Ser
        115
```

```
<210> SEQ ID NO 3
<211> LENGTH: 12
<212> TYPE: PRT
<213> ORGANISM: Artificial Sequence
<220> FEATURE:
<223> OTHER INFORMATION: Amino acid sequence of ASC01 VH CDR1

<400> SEQUENCE: 3

Gly Gly Ser Ile Asn Ser Gly Gly Tyr Tyr Trp Gly
1               5               10
```

```
<210> SEQ ID NO 4
<211> LENGTH: 16
<212> TYPE: PRT
<213> ORGANISM: Artificial Sequence
<220> FEATURE:
<223> OTHER INFORMATION: Amino acid sequence of ASC01 VH CDR2

<400> SEQUENCE: 4

Tyr Ile Tyr Pro Arg Gly Ser Ser Tyr Tyr Asn Pro Ser Leu Arg Ser
1               5               10              15
```

```
<210> SEQ ID NO 5
<211> LENGTH: 9
<212> TYPE: PRT
<213> ORGANISM: Artificial Sequence
<220> FEATURE:
<223> OTHER INFORMATION: Amino acid sequence of ASC01 VH CDR3

<400> SEQUENCE: 5

Val Gly Tyr Thr Gly Ala Phe Asp Ile
1               5
```

```
<210> SEQ ID NO 6
<211> LENGTH: 333
<212> TYPE: DNA
<213> ORGANISM: Artificial Sequence
<220> FEATURE:
<223> OTHER INFORMATION: Nucleotide sequence of ASC01 VL

<400> SEQUENCE: 6
caggctgtgc tcactcagcc gtcctcagtg tctgcggccc caggacagaa ggtcaccatc      60
tcctgctctg gaggcaactc caacattggg aataattatg tatcttggta ccagcagctc     120
ccaggaacag cccccaaact cctcatttat gacaataata agcgaccctc agggattcct     180
gaccgattct ctggctccaa gtctggcacg gcagccaccc tgggcatcac cggactccag     240
actggggacg aggccgatta ttactgcgga acatgggata gcagtctgag tgctggggtg     300
ttcggcgaag ggacccagct caccgtttta ggt                                 333
```

```
<210> SEQ ID NO 7
<211> LENGTH: 111
<212> TYPE: PRT
<213> ORGANISM: Artificial Sequence
<220> FEATURE:
<223> OTHER INFORMATION: Amino acid sequence of ASC01 VL

<400> SEQUENCE: 7

Gln Ala Val Leu Thr Gln Pro Ser Ser Val Ser Ala Ala Pro Gly Gln
1               5               10              15

Lys Val Thr Ile Ser Cys Ser Gly Gly Asn Ser Asn Ile Gly Asn Asn
            20              25              30
```

-continued

```
Tyr Val Ser Trp Tyr Gln Gln Leu Pro Gly Thr Ala Pro Lys Leu Leu
    35                  40                  45

Ile Tyr Asp Asn Asn Lys Arg Pro Ser Gly Ile Pro Asp Arg Phe Ser
    50                  55                  60

Gly Ser Lys Ser Gly Thr Ala Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Glu Gly Thr Gln Leu Thr Val Leu Gly
                100                 105                 110

<210> SEQ ID NO 8
<211> LENGTH: 13
<212> TYPE: PRT
<213> ORGANISM: Artificial Sequence
<220> FEATURE:
<223> OTHER INFORMATION: Amino acid sequence of ASC01 VL CDR1

<400> SEQUENCE: 8

Ser Gly Gly Asn Ser Asn Ile Gly Asn Asn Tyr Val Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence of ASC01 VL CDR2

<400> SEQUENCE: 9

Asp Asn Asn Lys Arg Pro Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Amino acid sequence of ASC01 VL CDR3

<400> SEQUENCE: 10

Gly Thr Trp Asp Ser Ser Leu Ser Ala Gly Val
1               5                   10

<210> SEQ ID NO 11
<211> LENGTH: 357
<212> TYPE: DNA
<213> ORGANISM: Artificial Sequence
<220> FEATURE:
<223> OTHER INFORMATION: Nucleotide sequence of ASC02 VH

<400> SEQUENCE: 11
caggtccagc tggtacagtc tggggctgag gtgaagaagc ctggggcctc aatgaaggtc        60
tcctgcacga cttctggata caccgtcacc ggctactaca tccactggct gcggcaggcc       120
cctggacaag ggtttgagtg gatgggatgg atcaacccta tcttggtgt cacaaattat        180 gctcagaagt tcagggcag ggtctccatg accaggacc cgtccatcaa gacagcctac        240
ctggaactga gcgggctgag atctgacgac acggccatgt attactgtgc gagagcatct       300
actggtggta tcttctatga ctattggggc cagggcaccc tggtcaccgt ctcctca          357

<210> SEQ ID NO 12
```

-continued

```
<211> LENGTH: 119
<212> TYPE: PRT
<213> ORGANISM: Artificial Sequence
<220> FEATURE:
<223> OTHER INFORMATION: Amino acid sequence of ASC02 VH

<400> SEQUENCE: 12

Gln Val Gln Leu Val Gln Ser Gly Ala Glu Val Lys Lys Pro Gly Ala
1               5                   10                  15

Ser Met Lys Val Ser Cys Thr Thr Ser Gly Tyr Thr Val Thr Gly Tyr
            20                  25                  30

Tyr Ile His Trp Leu Arg Gln Ala Pro Gly Gln Gly Phe Glu Trp Met
        35                  40                  45

Gly Trp Ile Asn Pro Asn Leu Gly Val Thr Asn Tyr Ala Gln Lys Phe
    50                  55                  60

Gln Gly Arg Val Ser Met Thr Arg Asp Pro Ser Ile Lys Thr Ala Tyr
65                  70                  75                  80

Leu Glu Leu Ser Gly Leu Arg Ser Asp Asp Thr Ala Met Tyr Tyr Cys
                85                  90                  95

Ala Arg Ala Ser Thr Gly Gly Ile Phe Tyr Asp Tyr Trp Gly Gln Gly
            100                 105                 110

Thr Leu Val Thr Val Ser Ser
        115

<210> SEQ ID NO 13
<211> LENGTH: 10
<212> TYPE: PRT
<213> ORGANISM: Artificial Sequence
<220> FEATURE:
<223> OTHER INFORMATION: Amino acid sequence of ASC02 VH CDR1

<400> SEQUENCE: 13

Gly Tyr Thr Val Thr Gly Tyr Tyr Ile His
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence of ASC02 VH CDR2

<400> SEQUENCE: 14

Trp Ile Asn Pro Asn Leu Gly Val Thr Asn Tyr Ala Gln Lys Phe Gln
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: Amino acid sequence of ASC02 VH CDR3

<400> SEQUENCE: 15

Ala Ser Thr Gly Gly Ile Phe Tyr Asp Tyr
1               5                   10

<210> SEQ ID NO 16
<211> LENGTH: 333
<212> TYPE: DNA
<213> ORGANISM: Artificial Sequence
<220> FEATURE:
```

-continued

<223> OTHER INFORMATION: Nucleotide sequence of ASC02 VL

<400> SEQUENCE: 16

```
aattttatgc tgactcagcc ccactctatg tcggagtctc cggggaagac ggttaccatc      60
tcctgcaccc gcagcagtgg caatattgcc agcaactatg tgcagtggta ccagcagcgc     120
ccgggcagtt cccccaccac tgtgatttat gacgataacc aaagaccctc tggggtccct     180
gatcggttct ctggctccat cgacagcatc tccaactctg cctccctcac catctctgga     240
ctgaagactg aggacgaggc tgactactat tgtcagtctt atgatagcag cagtgtgata     300
ttcggcggag ggaccaagct gaccgtccta ggt                                 333
```

<210> SEQ ID NO 17
<211> LENGTH: 111
<212> TYPE: PRT
<213> ORGANISM: Artificial Sequence
<220> FEATURE:
<223> OTHER INFORMATION: Amino acid sequence of ASC02 VL

<400> SEQUENCE: 17

```
Asn Phe Met Leu Thr Gln Pro His Ser Met Ser Glu Ser Pro Gly Lys
1               5                   10                  15

Thr Val Thr Ile Ser Cys Thr Arg Ser Ser Gly Asn Ile Ala Ser Asn
            20                  25                  30

Tyr Val Gln Trp Tyr Gln Gln Arg Pro Gly Ser Ser Pro Thr Thr Val
        35                  40                  45

Ile Tyr Asp Asp Asn Gln Arg Pro Ser Gly Val Pro Asp Arg Phe Ser
    50                  55                  60

Gly Ser Ile Asp Ser Ile Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Ser Val Ile Phe Gly Gly Gly Thr Lys Leu Thr Val Leu Gly
                100                 105                 110
```

<210> SEQ ID NO 18
<211> LENGTH: 13
<212> TYPE: PRT
<213> ORGANISM: Artificial Sequence
<220> FEATURE:
<223> OTHER INFORMATION: Amino acid sequence of ASC02 VL CDR1

<400> SEQUENCE: 18

```
Thr Arg Ser Ser Gly Asn Ile Ala Ser Asn Tyr Val Gln
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: Amino acid sequence of ASC02 VL CDR2

<400> SEQUENCE: 19

```
Asp Asp Asn Gln Arg Pro Ser
1               5
```

<210> SEQ ID NO 20
<211> LENGTH: 9
<212> TYPE: PRT
<213> ORGANISM: Artificial Sequence
<220> FEATURE:

-continued

<223> OTHER INFORMATION: Amino acid sequence of ASC02 VL CDR3

<400> SEQUENCE: 20

Gln Ser Tyr Asp Ser Ser Ser Val Ile
1               5

<210> SEQ ID NO 21
<211> LENGTH: 360
<212> TYPE: DNA
<213> ORGANISM: Artificial Sequence
<220> FEATURE:
<223> OTHER INFORMATION: Nucleotide sequence of ASC03 VH

<400> SEQUENCE: 21
caggtgcagc tggtggagtc cggggctgag gtgaagaagc ctgggtcctc ggtgaaggtc        60
tcctgcaagg cttctggagg caacttcagg aagtattcta tcagctgggt gcgacaggcc       120
cctggacaag ggcttgagtg gatgggatgg atcagcgctt acaatggtaa cacaaactat       180
gcacagaagc tccagggcag agtcaccatg accacagaca catccacgag cacagcctac       240
atggagctga ggagcctgag atctgacgac acggccgtgt attactgtgc gagagatttc       300
gacccttact atgatgcttt tgatatctgg ggccaaggga ccacggtcac cgtctcctca       360

<210> SEQ ID NO 22
<211> LENGTH: 120
<212> TYPE: PRT
<213> ORGANISM: Artificial Sequence
<220> FEATURE:
<223> OTHER INFORMATION: Amino acid sequence of ASC03 VH

<400> SEQUENCE: 22

Gln Val Gln Leu Val Glu Ser Gly Ala Glu Val Lys Lys Pro Gly Ser
1               5                   10                  15

Ser Val Lys Val Ser Cys Lys Ala Ser Gly Gly Asn Phe Arg Lys Tyr
            20                  25                  30

Ser Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Phe Asp Pro Tyr Tyr Asp Ala Phe Asp Ile Trp Gly Gln
            100                 105                 110

Gly Thr Thr Val Thr Val Ser Ser
        115                 120

<210> SEQ ID NO 23
<211> LENGTH: 10
<212> TYPE: PRT
<213> ORGANISM: Artificial Sequence
<220> FEATURE:
<223> OTHER INFORMATION: Amino acid sequence of ASC03 VH CDR1

<400> SEQUENCE: 23

Gly Gly Asn Phe Arg Lys Tyr Ser Ile Ser
1               5                   10

<210> SEQ ID NO 24
<211> LENGTH: 17

```
<212> TYPE: PRT
<213> ORGANISM: Artificial Sequence
<220> FEATURE:
<223> OTHER INFORMATION: Amino acid sequence of ASC03 VH CDR2

<400> SEQUENCE: 24

Trp Ile Ser Ala Tyr Asn Gly Asn Thr Asn Tyr Ala Gln Lys Leu Gln
1               5                   10                  15

Gly

<210> SEQ ID NO 25
<211> LENGTH: 11
<212> TYPE: PRT
<213> ORGANISM: Artificial Sequence
<220> FEATURE:
<223> OTHER INFORMATION: Amino acid sequence of ASC03 VH CDR3

<400> SEQUENCE: 25

Asp Phe Asp Pro Tyr Tyr Asp Ala Phe Asp Ile
1               5                   10

<210> SEQ ID NO 26
<211> LENGTH: 333
<212> TYPE: DNA
<213> ORGANISM: Artificial Sequence
<220> FEATURE:
<223> OTHER INFORMATION: Nucleotide sequence of ASC03 VL

<400> SEQUENCE: 26
cagtctgccc tgactcagcc tgcctccgtg tctgggtctc ctggacagtc gatcaccatc      60
tcctgcactg ggaccagcag tgacgttggt gcttataatt atgtctcctg gtaccaacaa     120
cacccaggca aagcccccaa actcatgatt tatgatgtca gtaatcggct ctcagggggtt    180 tctaatcgct tctctggctc caagtctggc aacagggcct ccctgaccat ctctgggctc     240
caggctgagg acgaggctga ttattactgc agctcatata aagcggcaa cagtctggcg      300 ttcggcggag ggaccaagct gaccgtccta ggt                                  333

<210> SEQ ID NO 27
<211> LENGTH: 111
<212> TYPE: PRT
<213> ORGANISM: Artificial Sequence
<220> FEATURE:
<223> OTHER INFORMATION: Amino acid sequence of ASC03 VL

<400> SEQUENCE: 27

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Leu Ser Gly Val Ser Asn Arg Phe
        50                  55                  60

Ser Gly Ser Lys Ser Gly Asn Arg Ala Ser Leu Thr Ile Ser Gly Leu
65                  70                  75                  80

Gln Ala Glu Asp Glu Ala Asp Tyr Tyr Cys Ser Ser Tyr Arg Ser Gly
                85                  90                  95

Asn Ser Leu Ala Phe Gly Gly Gly Thr Lys Leu Thr Val Leu Gly
            100                 105                 110
```

<210> SEQ ID NO 28
<211> LENGTH: 14
<212> TYPE: PRT
<213> ORGANISM: Artificial Sequence
<220> FEATURE:
<223> OTHER INFORMATION: Amino acid sequence of ASC03 VL CDR1

<400> SEQUENCE: 28

Thr Gly Thr Ser Ser Asp Val Gly Ala Tyr Asn Tyr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Amino acid sequence of ASC03 VL CDR2

<400> SEQUENCE: 29

Asp Val Ser Asn Arg Leu Ser
1               5

<210> SEQ ID NO 30
<211> LENGTH: 10
<212> TYPE: PRT
<213> ORGANISM: Artificial Sequence
<220> FEATURE:
<223> OTHER INFORMATION: Amino acid sequence of ASC03 VL CDR3

<400> SEQUENCE: 30

Ser Ser Tyr Arg Ser Gly Asn Ser Leu Ala
1               5                   10

<210> SEQ ID NO 31
<211> LENGTH: 348
<212> TYPE: DNA
<213> ORGANISM: Artificial Sequence
<220> FEATURE:
<223> OTHER INFORMATION: Nucleotide sequence of ASC04 VH

<400> SEQUENCE: 31
caggtccagc tggtgcagtc tgggggctgag gtgaagaagc ctgggtcctc ggtgaaggtc      60
tcctgcaagg cttctggggg caccttcagc acctacgcta tcaactgggt gcgacaggcc     120
cctggacaag ggcttgagtg gatgggatgg atgaacccta acagtggtaa cacaggctat     180
gcacagaagt tccagggcag agtcaccatg accaggaaca cctccataag cacagcctac     240
atggagctga gcagcctgag atctgaggac acggccgtgt attactgtgc gagatatagc     300
tacggtatgg acgtctgggg ccaagggact acggtcaccg tctcctca               348

<210> SEQ ID NO 32
<211> LENGTH: 116
<212> TYPE: PRT
<213> ORGANISM: Artificial Sequence
<220> FEATURE:
<223> OTHER INFORMATION: Amino acid sequence of ASC04 VH

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Asn Trp Val Arg Gln Ala Pro Gly Gln Gly Leu Glu Trp Met
        35                  40                  45

```
Gly Trp Met Asn Pro Asn Ser Gly Asn Thr Gly Tyr Ala Gln Lys Phe
    50              55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ser Tyr Gly Met Asp Val Trp Gly Gln Gly Thr Thr Val
            100                 105                 110

Thr Val Ser Ser
        115

<210> SEQ ID NO 33
<211> LENGTH: 10
<212> TYPE: PRT
<213> ORGANISM: Artificial Sequence
<220> FEATURE:
<223> OTHER INFORMATION: Amino acid sequence of ASC04 VH CDR1

<400> SEQUENCE: 33

Gly Gly Thr Phe Ser Thr Tyr Ala Ile Asn
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Amino acid sequence of ASC04 VH CDR2

<400> SEQUENCE: 34

Trp Met Asn Pro Asn Ser Gly Asn Thr Gly Tyr Ala Gln Lys Phe Gln
1               5                   10                  15

Gly

<210> SEQ ID NO 35
<211> LENGTH: 7
<212> TYPE: PRT
<213> ORGANISM: Artificial Sequence
<220> FEATURE:
<223> OTHER INFORMATION: Amino acid sequence of ASC04 VH CDR3

<400> SEQUENCE: 35

Tyr Ser Tyr Gly Met Asp Val
1               5

<210> SEQ ID NO 36
<211> LENGTH: 348
<212> TYPE: DNA
<213> ORGANISM: Artificial Sequence
<220> FEATURE:
<223> OTHER INFORMATION: Nucleotide sequence of ASC04 VL

<400> SEQUENCE: 36
caggctgtgc tcactcagcc gtcttccctc tctgcatctc ctggagcatc agtcagtctc      60
acctgcactt tacgcagtgg catcaatgtt ggtgcctaca ggatatactg gtaccagcag     120
aagccaggga gtcctcccca gtttctcctg aggtacaaat cagactcaga taagcagcag     180
ggctctggag tccccagccg cttctctgga tccagagatg cttcggccaa tgcaggaatt     240
ttactcatct ctgggctccg gtctgaggat gaggctgact attactgtgc gatttggcac     300
agcagcgctt gggtgttcgg cggagggacc aagctgaccg tcctaggt                  348
```

-continued

```
<210> SEQ ID NO 37
<211> LENGTH: 116
<212> TYPE: PRT
<213> ORGANISM: Artificial Sequence
<220> FEATURE:
<223> OTHER INFORMATION: Amino acid sequence of ASC04 VL

<400> SEQUENCE: 37

Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
            20                  25                  30

Tyr Arg Ile Tyr Trp Tyr Gln Gln Lys Pro Gly Ser Pro Pro Gln Phe
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Arg Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Lys Leu
            100                 105                 110

Thr Val Leu Gly
        115

<210> SEQ ID NO 38
<211> LENGTH: 14
<212> TYPE: PRT
<213> ORGANISM: Artificial Sequence
<220> FEATURE:
<223> OTHER INFORMATION: Amino acid sequence of ASC04 VL CDR1

<400> SEQUENCE: 38

Thr Leu Arg Ser Gly Ile Asn Val Gly Ala Tyr Arg Ile Tyr
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Amino acid sequence of ASC04 VL CDR2

<400> SEQUENCE: 39

Lys Ser Asp Ser Asp Lys Gln
1               5

<210> SEQ ID NO 40
<211> LENGTH: 9
<212> TYPE: PRT
<213> ORGANISM: Artificial Sequence
<220> FEATURE:
<223> OTHER INFORMATION: Amino acid sequence of ASC04 VL CDR3

<400> SEQUENCE: 40

Ala Ile Trp His Ser Ser Ala Trp Val
1               5

<210> SEQ ID NO 41
<211> LENGTH: 357
<212> TYPE: DNA
<213> ORGANISM: Artificial Sequence
<220> FEATURE:
<223> OTHER INFORMATION: Nucleotide sequence of ASC05 VH
```

-continued

<400> SEQUENCE: 41

```
caggtgcagc tggtggagtc cgggggctgag gtgaagaagc ctgggggcctc agtgagggtt        60 tcctgcaagg catctggata cagtttcacc aactactata tgcactgggt gcgacaggcc       120
cctggacaag ggcttgagtg gatgggaatt atcagcccta gtggtcgtag cacaagcttc       180
gcacagaagt tccagggcag agtcaccatg accagggaca cgtccacgag cacagtctac       240
atgcatttga gcagcctgag atctgacgac acggccgtgt attactgtgc gagaggggcg       300
tggtccactg atgcttttga tatctggggc caagggacca cggtcaccgt ctcctca         357
```

<210> SEQ ID NO 42
<211> LENGTH: 119
<212> TYPE: PRT
<213> ORGANISM: Artificial Sequence
<220> FEATURE:
<223> OTHER INFORMATION: Amino acid sequence of ASC05 VH

<400> SEQUENCE: 42

```
Gln Val Gln Leu Val Glu Ser Gly Ala Glu Val Lys Lys Pro Gly Ala
1               5                   10                  15

Ser Val Arg Val Ser Cys Lys Ala Ser Gly Tyr Ser Phe Thr Asn Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Arg Ser Thr Ser Phe Ala Gln Lys Phe
    50                  55                  60

Gln Gly Arg Val Thr Met Thr Arg Asp Thr Ser Thr Ser Thr Val Tyr
65                  70                  75                  80

Met His Leu Ser Ser Leu Arg Ser Asp Asp Thr Ala Val Tyr Tyr Cys
                85                  90                  95

Ala Arg Gly Ala Trp Ser Thr Asp Ala Phe Asp Ile Trp Gly Gln Gly
            100                 105                 110

Thr Thr Val Thr Val Ser Ser
        115
```

<210> SEQ ID NO 43
<211> LENGTH: 10
<212> TYPE: PRT
<213> ORGANISM: Artificial Sequence
<220> FEATURE:
<223> OTHER INFORMATION: Amino acid sequence of ASC05 VH CDR1

<400> SEQUENCE: 43

```
Gly Tyr Ser Phe Thr Asn Tyr Tyr Met His
1               5                   10
```

<210> SEQ ID NO 44
<211> LENGTH: 17
<212> TYPE: PRT
<213> ORGANISM: Artificial Sequence
<220> FEATURE:
<223> OTHER INFORMATION: Amino acid sequence of ASC05 VH CDR2

<400> SEQUENCE: 44

```
Ile Ile Ser Pro Ser Gly Arg Ser Thr Ser Phe Ala Gln Lys Phe Gln
1               5                   10                  15

Gly
```

<210> SEQ ID NO 45

```
<211> LENGTH: 10
<212> TYPE: PRT
<213> ORGANISM: Artificial Sequence
<220> FEATURE:
<223> OTHER INFORMATION: Amino acid sequence of ASC05 VH CDR3

<400> SEQUENCE: 45

Gly Ala Trp Ser Thr Asp Ala Phe Asp Ile
1               5                   10

<210> SEQ ID NO 46
<211> LENGTH: 339
<212> TYPE: DNA
<213> ORGANISM: Artificial Sequence
<220> FEATURE:
<223> OTHER INFORMATION: Nucleotide sequence of ASC05 VL

<400> SEQUENCE: 46
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca aagcccccaa actcatgatt tatgagggca gtaagcggcc ctcagggggtt    180 tctaatcgct ctctctggctc caagtctggc aacacggcct ccctgacaat ctctgggctc    240
caggctgagg atgaggctga gtatcactgc agctcattta caggcaaggg ttatgtcttc     300
ggaactggga ccaagctgac cgtcctaggt ggcctcgggg                          339

<210> SEQ ID NO 47
<211> LENGTH: 113
<212> TYPE: PRT
<213> ORGANISM: Artificial Sequence
<220> FEATURE:
<223> OTHER INFORMATION: Amino acid sequence of ASC05 VL

<400> SEQUENCE: 47

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Glu Tyr His Cys Ser Ser Phe Thr Gly Lys
                85                  90                  95

Gly Tyr Val Phe Gly Thr Gly Thr Lys Leu Thr Val Leu Gly Gly Leu
            100                 105                 110

Gly

<210> SEQ ID NO 48
<211> LENGTH: 14
<212> TYPE: PRT
<213> ORGANISM: Artificial Sequence
<220> FEATURE:
<223> OTHER INFORMATION: Amino acid sequence of ASC05 VL CDR1

<400> SEQUENCE: 48

Thr Gly Thr Ser Ser Asp Val Gly Ser Tyr Asn Leu Val Ser
1               5                   10
```

-continued

<210> SEQ ID NO 49
<211> LENGTH: 7
<212> TYPE: PRT
<213> ORGANISM: Artificial Sequence
<220> FEATURE:
<223> OTHER INFORMATION: Amino acid sequence of ASC05 VL CDR2

<400> SEQUENCE: 49

Glu Gly Ser Lys Arg Pro Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Amino acid sequence of ASC05 VL CDR3

<400> SEQUENCE: 50

Ser Ser Phe Thr Gly Lys Gly Tyr Val
1               5

<210> SEQ ID NO 51
<211> LENGTH: 357
<212> TYPE: DNA
<213> ORGANISM: Artificial Sequence
<220> FEATURE:
<223> OTHER INFORMATION: Nucleotide sequence of ASC06 VH

<400> SEQUENCE: 51
caggtacagc tgcagcagtc aggggggaggc ttggtacagc ctggggggtc cctgagactc      60
tcctgtgcag cctctggatt caccttttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatagt     300
ttctatgggt atagcaaggg ggactggggc cagggcaccc tggtcaccgt ctcctca        357

<210> SEQ ID NO 52
<211> LENGTH: 119
<212> TYPE: PRT
<213> ORGANISM: Artificial Sequence
<220> FEATURE:
<223> OTHER INFORMATION: Amino acid sequence of ASC06 VH

<400> SEQUENCE: 52

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Phe Tyr Gly Tyr Ser Lys Gly Asp Trp Gly Gln Gly
            100                 105                 110

-continued

```
Thr Leu Val Thr Val Ser Ser
        115

<210> SEQ ID NO 53
<211> LENGTH: 10
<212> TYPE: PRT
<213> ORGANISM: Artificial Sequence
<220> FEATURE:
<223> OTHER INFORMATION: Amino acid sequence of ASC06 VH CDR1

<400> SEQUENCE: 53

Gly Phe Thr Phe Ser Ser Tyr Ala Met Ser
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Amino acid sequence of ASC06 VH CDR2

<400> SEQUENCE: 54

Ala Ile Ser Gly Ser Gly Gly Ser Thr Tyr Tyr Ala Asp Ser Val Lys
1               5                   10                  15

Gly

<210> SEQ ID NO 55
<211> LENGTH: 10
<212> TYPE: PRT
<213> ORGANISM: Artificial Sequence
<220> FEATURE:
<223> OTHER INFORMATION: Amino acid sequence of ASC06 VH CDR3

<400> SEQUENCE: 55

Asp Ser Phe Tyr Gly Tyr Ser Lys Gly Asp
1               5                   10

<210> SEQ ID NO 56
<211> LENGTH: 333
<212> TYPE: DNA
<213> ORGANISM: Artificial Sequence
<220> FEATURE:
<223> OTHER INFORMATION: Nucleotide sequence of ASC06 VL

<400> SEQUENCE: 56
cagtctgccc tgactcagcc tgcctccgtg tctgggtctc ctggacagtc gatcaccatc      60
tcctgcactg gaaccagcag tgacgttggt gcttataact atgtctcctg gtaccaacaa     120
cagccaggca aagcccccaa actcatgatt tatggggtca gtaatcggcc ctcagggggtt     180 tctaatcgct tctctggctc caagtctggc aacgcggcct ccctgaccat ctctgggctc     240
caggctgagg acgaggctga ttattactgc agctcatata caagcagcag cacttatgtc     300
ttcggaactg ggaccaagct gaccgtccta ggt                                  333

<210> SEQ ID NO 57
<211> LENGTH: 111
<212> TYPE: PRT
<213> ORGANISM: Artificial Sequence
<220> FEATURE:
<223> OTHER INFORMATION: Amino acid sequence of ASC06 VL

<400> SEQUENCE: 57

Gln Ser Ala Leu Thr Gln Pro Ala Ser Val Ser Gly Ser Pro Gly Gln
1               5                   10                  15
```

-continued

```
Ser Ile Thr Ile Ser Cys Thr Gly Thr Ser Ser Asp Val Gly Ala Tyr
        20              25              30

Asn Tyr Val Ser Trp Tyr Gln Gln Gln Pro Gly Lys Ala Pro Lys Leu
        35              40              45

Met Ile Tyr Gly Val Ser Asn Arg Pro Ser Gly Val Ser Asn Arg Phe
    50              55              60

Ser Gly Ser Lys Ser Gly Asn Ala Ala Ser Leu Thr Ile Ser Gly Leu
65              70              75              80

Gln Ala Glu Asp Glu Ala Asp Tyr Tyr Cys Ser Ser Tyr Thr Ser Ser
                85              90              95

Ser Thr Tyr Val Phe Gly Thr Gly Thr Lys Leu Thr Val Leu Gly
            100             105             110

<210> SEQ ID NO 58
<211> LENGTH: 15
<212> TYPE: PRT
<213> ORGANISM: Artificial Sequence
<220> FEATURE:
<223> OTHER INFORMATION: Amino acid sequence of ASC06 VL CDR1

<400> SEQUENCE: 58

Thr Gly Thr Ser Ser Asp Val Gly Ala Tyr Asn Tyr Val Ser Trp
1               5               10              15

<210> SEQ ID NO 59
<211> LENGTH: 7
<212> TYPE: PRT
<213> ORGANISM: Artificial Sequence
<220> FEATURE:
<223> OTHER INFORMATION: Amino acid sequence of ASC06 VL CDR2

<400> SEQUENCE: 59

Gly Val Ser Asn Arg Pro Ser
1               5

<210> SEQ ID NO 60
<211> LENGTH: 10
<212> TYPE: PRT
<213> ORGANISM: Artificial Sequence
<220> FEATURE:
<223> OTHER INFORMATION: Amino acid sequence of ASC06 VL CDR3

<400> SEQUENCE: 60

Ser Ser Tyr Thr Ser Ser Ser Thr Tyr Val
1               5               10
```